United States Patent
Ho et al.

(10) Patent No.: US 10,799,593 B2
(45) Date of Patent: Oct. 13, 2020

(54) NANODIAMOND PARTICLE COMPLEXES

(71) Applicant: Northwestern University, Evanston, IL (US)

(72) Inventors: Dean Ho, Los Angeles, CA (US); Mark Chen, Chicago, IL (US); Erik Pierstorff, Falls Church, VA (US); Erik Robinson, Chicago, IL (US); Robert Lam, Evanston, IL (US); Rafael Shimkunas, Palo Alto, CA (US); Xueqing Zhang, Evanston, IL (US); Houjin Huang, Evanston, IL (US)

(73) Assignee: Northwestern University, Evansont, IL (US)

( * ) Notice: Subject to any disclaimer, the term of this patent is extended or adjusted under 35 U.S.C. 154(b) by 0 days.

(21) Appl. No.: 14/797,722

(22) Filed: Jul. 13, 2015

(65) Prior Publication Data

US 2016/0058887 A1    Mar. 3, 2016

Related U.S. Application Data

(63) Continuation-in-part of application No. 12/789,966, filed on May 28, 2010, now abandoned, and a continuation-in-part of application No. 12/481,400, filed on Jun. 9, 2009, now abandoned.

(60) Provisional application No. 61/181,993, filed on May 28, 2009, provisional application No. 61/059,979, filed on Jun. 9, 2008, provisional application No. 61/059,976, filed on Jun. 9, 2008.

(51) Int. Cl.
| | | |
|---|---|---|
| *A61K 47/69* | (2017.01) | |
| *A61K 31/704* | (2006.01) | |
| *A61K 47/02* | (2006.01) | |
| *B82Y 5/00* | (2011.01) | |
| *C07K 17/14* | (2006.01) | |
| *A61K 47/48* | (2006.01) | |

(52) U.S. Cl.
CPC ...... *A61K 47/48861* (2013.01); *A61K 31/704* (2013.01); *A61K 47/02* (2013.01); *A61K 47/6921* (2017.08); *A61K 47/6923* (2017.08); *A61K 47/6929* (2017.08); *B82Y 5/00* (2013.01); *C07K 17/14* (2013.01)

(58) Field of Classification Search
None
See application file for complete search history.

(56) References Cited

U.S. PATENT DOCUMENTS

| | | |
|---|---|---|
| 3,640,741 A | 2/1972 | Etes |
| 3,865,108 A | 2/1975 | Hartop |
| 3,992,562 A | 11/1976 | Denzinger et al. |
| 4,002,173 A | 1/1977 | Manning |
| 4,014,335 A | 3/1977 | Arnold |
| 4,207,893 A | 6/1980 | Michaels |
| 6,723,814 B2 | 4/2004 | Meier et al. |
| 7,211,108 B2 | 5/2007 | Furst et al. |
| 7,294,340 B2 | 11/2007 | Sung et al. |
| 7,312,301 B2 | 12/2007 | Fang |
| 7,329,414 B2 | 2/2008 | Fisher et al. |
| 7,407,912 B2 | 8/2008 | Mertens |
| 7,413,752 B2 | 8/2008 | Sawhney |
| 7,419,709 B2 | 9/2008 | Rypacek et al. |
| 7,459,169 B2 | 12/2008 | Nilsson et al. |
| 7,511,083 B2 | 3/2009 | Madsen |
| 7,820,130 B2 | 10/2010 | Khabashesku et al. |
| 7,828,728 B2 | 11/2010 | Boock et al. |
| 2003/0228681 A1 | 12/2003 | Ritts et al. |
| 2005/0281858 A1 | 12/2005 | Kloke et al. |
| 2006/0088571 A1 | 4/2006 | Chen et al. |
| 2006/0195176 A1 | 8/2006 | Bates et al. |
| 2006/0222756 A1 | 10/2006 | Davila et al. |
| 2007/0259101 A1 | 11/2007 | Kleiner et al. |
| 2008/0075753 A1 | 3/2008 | Chappa |
| 2010/0040672 A1 | 2/2010 | Ho et al. |
| 2010/0305309 A1 | 12/2010 | Ho et al. |

FOREIGN PATENT DOCUMENTS

| | | |
|---|---|---|
| WO | 2008022258 | 2/2008 |
| WO | 2009152167 | 12/2009 |
| WO | 2010138837 | 12/2010 |

OTHER PUBLICATIONS

Alexanian et al, "Primary Dexamethasone Treatment of Multiple Myeloma," Blood, vol. 80, No. 4, Aug. 15, 1992, pp. 887-890.*
Adochio et al., "Rescuing 3T3-L1 Adipocytes from Insulin Resistance Induced by Stimulation of Akt-Mammalian Target of Rapamycin/p70 S6 Kinase (S6K1) Pathway and Serine Phosphorylation of Insulin Receptor Substrate-1: Effect of Reduced Expression of p. 85_ Subunit of Phosphatidylinositol 3-Kinase and S6K1 Kinase." Endocrinology, 2009, 150(3):1165-73.
Ajima et al., "Carbon Nanohorns as Anticancer Drug Carriers." Mol Pharm, 2005, 2(6):475-80.
Allen and Cullis, "Drug Delivery Systems: Entering the Mainstream." Science, 2004, 303(5665): 1818-22.
Andreopoulos et al., "Photoimmobilization of organophosphorus hydrolase within a PEG-based hydrogel," Biotechnology and Bioengineering, 2009, 65:579-588.

(Continued)

*Primary Examiner* — Rachael E Bredefeld
(74) *Attorney, Agent, or Firm* — Casimir Jones, S.C.; Jason R. Bond

(57) ABSTRACT

The present invention provides various functionalized nanodiamond particles. In particular, the present invention provides soluble complexes of nanodiamond particles and therapeutic agents, for example insoluble therapeutics, anthracycline and/or tetracycline compounds, nucleic acids, proteins, etc. The present invention also provides materials and devices for the controlled release of therapeutics, and methods for uses thereof.

1 Claim, 57 Drawing Sheets

Specification includes a Sequence Listing.

(56) References Cited

OTHER PUBLICATIONS

Anseth et al., "In situ forming degradable networks and their application in tissue engineering and drug delivery," Journal of Controlled Release, 2002, 78:199-209.
Auguste et al., "Triggered release of siRNA from poly(ethylene glycol)-protected, pHdependent liposomes." J Control Release, 2008, 130(3):266-74.
Bakowicz et al., Biocompatibility of NCD, Journal of Wide Bandgap Materials, 2002, 9:261-272.
Behler et al., 2009, "Nanodiamond-Polymer Composite Fibers and Coatings." ACS Nano 3(2):363-9.
Bettinger et al., 1999, "Size Reduction of Galactosylated PEI/DNA Complexes Improves Lectin-Mediated Gene Transfer into Hepatocytes." Bioconjugate Chem. 10, 558-561.
Bhattacharjee et al. "Luminescent CdS Nanoparticles Embedded in Polyethylene Glycol (PEG 300) Matrix Thin Film," Journal of Nanoparticle Research, 2002, 4:225-230.
Bondar and Puzyr, "Nanodiamonds for Biological Investigations." Phys. Solid State, 2004, 46:716-719.
Bondar et al., "Applications of nanodiamonds for separation and purification of proteins," Physics of the Solid State, 2004, 46:758-760.
Bruck. Blood Compatible Synthetic Polymers, CC Thomas publisher, Springfield, IL, 1974, TOC only, will provide specific citations upon Examiner request.
Bryant & Anseth, Controlling the spatial distribution of ECM components in degradable PEG hydrogels for tissue engineering cartilage, Journal of Biomedical Materials Research Part A, 2003, 64:70-79.
Bryant et al., "Cytocompatibility of UV and visible light photoinitiating systems on cultured NIH/3T3 fibroblasts in vitro," Journal of Biomaterials Science—Polymer Edition, 2000, 11:439-457.
Burt et al., "Drug-eluting stents: A multidisciplinary success Story," Advanced Drug Delivery Reviews, 2006, 58:350-357.
Burt etal., "Drug-eluting stents: an innovative multidisciplinary drug delivery platform," Advanced Drug Delivery Reviews, 2006, 58:345-346.
Cao et al., 2008, "Insulin Increases Tristetraprolin and Decreases VEGF Gene Expression in Mouse 3T3-L1 Adipocytes." Obesity 16(6):1208-18.
Catellani et al., "Modified Release Tablet Formulation," Progress in Biomedical Engineering, 5, Polymers in Medicine III, Migliaresi eds., Elsevier Science Publishers B.V., Amsterdam, 1988, pp. 169-174.
CEVC and Richardsen. "Lipid vesicles and membrane fusion." Adv Drug Deliv Rev, 1999, 38(3):207-32.
Chang et al., "Cell and Protein Compatibility of Parylene-C Surfaces," Langmuir, 2007, 23:11718-11725.
Chang et al., Mass production and dynamic imaging of fluorescent nanodiamonds, Nature Nanotechnology, 2008, 3:284-288.
Chao et al., "Nanometer-Sized Diamond Particle as a Probe for Biolabeling," Biophysical Journal, 2007, 93:2199-2208.
Cheong et al., 2009. "Superparamagnetic iron oxide nanoparticles-loaded chitosan-linoleic acid nanoparticles as an effective hepatocyte-targeted gene delivery system." Int J Pharm 372(1-2):169-76.
Chow et al. "Copolymeric nanofilm platform for controlled and localized therapeutic delivery" ASC Nano, 2008, 2:33-40.
Chow et al., "Attenuation of Cellular Inflammation Using Glucocorticoid-Functionalized Copolymers," Proceedings of the 2nd IEEE International Conference on Nano/Micro Engineereed and Molecular Systems, Jan. 16-19, 2007, Bangkok, Thailand, pp. 1039-1043.
De Bartolo et al., "Novel membranes and surface modification able to activate specific cellular responses," Biomolecular Engineering 2007, 24:23-26.
Deming, "Methodologies for preparation of synthetic block copolypeptides: materials with future promise in drug delivery," Advanced Drug Delivery Reviews, 2002, 54:1145-1155.

Dobson. 2006. "Gene therapy progress and prospects: magnetic nanoparticle-based gene delivery." Gene Ther 13(4):283-7.
Dolbier & Beach, "Parylene-AF4: a polymer with exceptional dielectric and thermal properties," Journal of Fluorine Chemistry 2003, 122:97-104.
Dolmatov, "Detonation syntheis ultradispersed diamonds: properties and applications," Russian Chemical Reviews, 2001, 70:607-626.
Eskin et al., "Growth of cultured calf aortic smooth muscle cells on cardiovascular prosthetic materials," Journal of Biomedical Materials Research, 1976, 10:113-122.
Farías et al., 1989. "Relationship between isoelectric point of native and chemically modified insulin and liposomal fusion." Biochem J; 264(1):285-7.
Farokhzad and Langer. 2009. "Impact of Nanotechnology on Drug Delivery." ACS Nano 3(1):16-20.
Feng and Andrade. 1994. "Protein adsorption of low-temperature isotropic carbon: I. Protein conformational change probed by differential scanning calorimetry." J Biomed Mater Res 28(6):735-43.
Fisher et al., "Tamoxifen for Prevention of Breast Cancer: Report of the National Surgical Adjuvant Breast and Bowel Project P-1 Study." J. Natl. Cancer Inst., 1998, 9:1371-1388.
Fisher et al., "Tamoxifen in Treatment of Intraductal Breast Cancer: National Surgical Adjuvant Breast and Bowel Project B-24 Randomised Controlled Trial." Lancet, 1999, 353:1993-2000.
Fontaine & Lu. Chemical Vapor Deposition Polymerization The Growth and Properties of Parylene Thin Films, Kluwear Academic Publishers, Norwell, MA, 2004, TOC only, 5 pages.
Fontaine et al., "Polymeric surface modifications of tantalum stents," J Endovasc Surg., 1996, 3:276-283.
Fu et al. 2007. "Characterization and application of single fluorescent nanodiamonds as cellular biomarkers." Proc Nat Acad Sci USA 104(3):727-32.
Fuertges & Abuchowski, "The Clinical Efficacy of Poly(Ethylene Glycol)-Modified Proteins," Journal of Controlled Release, 1990, 11:139-148.
Gauduchon et al., "4-Hydroxytamoxifen Inhibits Proliferation of Multiple Myeloma Cells In vitro through Down-Regulation of c-Myc, Up-Regulation of p27Kip1, and Modulation of Bcl-2 Family Members." Clin. Canc. Res., 2005, 11:2345-2354.
Gayet & Fortier., "High water content BSA-PEG hydrogel for controlled release device: Evaluation of the drug release properties," Journal of Controlled Release, 1996, 38:177-184.
Gelperina et al., "The Potential Advantages of Nanoparticle Drug Delivery Systems in Chemotherapy of Tuberculosis." Am J Resp Crit Care, 2005, 172(12):1487-90.
Ghannam et al., "Interaction of type-I collagen with phospholipid monolayer" Biophys. Chem., 1999, 80:31-40.
Goga et al., "Inhibition of Cdk1 as a Potential Therapy for Tumors Over-Expressing MYC." Nat. Med., 2007, 13:820-827.
Gorham, "A New, General Synthetic Method for the Preparation of Linear Poly-p-xylylenes," Journal of Polymer Science, 1966, 4:3027-3039.
Graff et al., "Virus-Assisted Loading of Polymeric Nanocontainers" Proc Nat Acad. Sci., 2002, 99:5064-5068.
Grant et al, "Layer-By-Layer Assembly of Collagen Thin Films: Controlled Thickness and Biocompatibility" Biomed Microdevices, 2001, 3:301-306.
Grattan et al., "The thermal aging of parylene and the effect of antioxidant," Studies in Conservation, 1991, 36:44-52.
Greenway et al., "Topical insulin in wound healing: a randomised, double-blind, placebo-controlled trial." J Wound Care, 1999, 8(10):526-8.
Grube et al, "Six-month clinical and angiograplric results of a dedicated drug-eluting stent for the treatment of coronary bifurcation narrowings," The American Journal of Cardiology, 2007, 99:1691-1697.
Gruen, "Nanocrystalline Diamond Films." Annu. Rev. Mater. Sci., 1999, 29:211-259.
Gwinn and Vallyathan, "Nanoparticles: Health Effects—Pros and Cons." Environ Health Perspect, 2006,114(12):1818-25.
Handbook of Common Polymers, Roff et al. eds., The Chemical Rubber Co. pub., Cleveland, OH, 1971, TOC only, 3 pages.

(56) References Cited

OTHER PUBLICATIONS

Hanson et al., "Nanoscale double emulsions by single-component block copolypeptides." Nature, 2008, 455(7209):85-8.
Hartl et al., "Protein-modified nanocrystalline diamond thin films for biosensor applications," Nature Materials, 2004, 3:736-742.
Härtl et al., "Protein-Modified Nanocrystalline Diamond Thin Films for Biosensor Applications." Nat. Mater . . . 2004, 3:736-742.
Hilder and Hill, "Carbon nanotubes as drug delivery nanocapsules." Curr Appl Phys, 2007, 8(3-4):258-61.
Ho et al., "Fabrication of biofunctional nanomaterials via *Eschericlria coli* OmpF protein air water interface insertion/integration with copolymeric amphiphiles" Nanomedicine,2006, 2: 103-112.
Ho et al., "Fabrication of biomolecule-copolymer hybrid nanovesicles as energy conversion systems" Nanotechnology, 2005, 16:3120-3132.
Ho et al., "Functionalizing Biomimetic Membranes with Energy Transducing Proteins" 2004 Proc. of the Mat. Res. Soc. 823:W11.8.1-W11.8.6.
Ho et al., "Hybrid Protein/Polymer Biomimetic Membranes" 2004 IEEE Trans. Nanotechnology, 3:256-263.
Ho et al., "Protein-driven energy transduction across polymeric biomembranes" Nanotechnology, 2004, 15:1084-1094.
Hoffman, "Bioconjugates of intelligent polymers and recognition proteins for use in diagnostics and affinity separations," Clinical Chemistry 2000, 46:1478-1486.
Huang & Brazel, "On the importance and mechanisms of burst release in matrix-controlled drug delivery systems," Journal of Controlled Release, 2007, 73:121-136.
Huang & Chang, "Adsorption and Immobilization of Cytochrome c on Nanodiamonds," Langmuir, 2004, 20:5879-5884.
Huang et al. "Ultrananocrystalline Diamond Thin Films Functionalized with Therapeutically Active Collagen Networks." J Phys Chem B, 2009, 113(10):2966-71.
Huang et al., "Active Nanodiamond Hydrogels for Chemotherapeutic Delivery," Nano Letters, 2007, 7:3305-3314.
Huang et al., "Controlled drug release from hydrogel nanoparticle networks," Journal of Controlled Release, 2004, 94:303-311.
Huang et al., "Protein-Mediated Assembly of Nanodiamond Hydrogels into a Biocompatible and Biofunctional Multilayer," NanofilmACS Nano, 2008, 2:203-212.
Huang et al., "Active Nanodiamond Hydrogels for Chemotherapeutic Delivery." Nano Lett, 2007, 7(11):3305-14.
Huang et al., "Protein-Mediated Assembly of Nanodiamond Hydrogels into a Biocompatible and Biofunctional Multilayer Nanofilm." ACS Nano, 2008, 2(2):203-12.
Iida et al. 2002. "Insulin Inhibits Apoptosis of Macrophage Cell Like, THP-1 Cells, via Phosphatidylinositol-3-Kinas-Dependent Pathway." Arterioscler Thromb Vasc Biol 22(3):380-6.
Jain, "Delivery of molecular and cellular medicine to solid tumors," Advanced Drug Delivery Reviews, 2001, 46:149-168.
Jeong et al., "Inhibition of the Stem Cell Factor-Induced Migration of Mast Cells by Dexamethasone," 2003, 144:4080-4086.
Jurisicova et al., "Molecular requirements for doxorubicin-mediated death in murine oocytes," Cell Death Differ, 2006, 13:1466-1474.
Kam et al. 2005. "Carbon Nanotubes as Multifunctional Biological Transporters and Near-Infrared Agents for Selective Cancer Cell Destruction." Proc. Nat. Acad. Sci.—USA 102, 11600-11605.
Kim et al. 2005. "Polymeric Worm Micelles as Nano-Carriers for Drug Delivery." Nanotechnology 16, S484-S491.
Kim et al., "Hydrogels: Swelling, Drug Loading, and Release," Pharmaceutical Research, 1992, 9:283-290.
Kircheis et al., "Design and Gene Delivery Activity of Modified Polyethylenimines." Advanced Drug Delivery Reviews, 2001, 53:341-358.
Kossovsky et al., "Surface-Modified Diamond Nanoparticles as Antigen Delivery Vehicles," Bioconjugate Chemistry, 1995, 6:507-511.
Kramer et al., "Polymerization of Para-Xylylene Derivatives (Parylene Polymerization). I. Deposition Kinetics for Parylene N and Parylene C," 1984, 22:475-490.

Krucoff et al., "Drug-eluting stents 'deliver heartburn'—How do we spell relief going forward," Circulation, 2007, 115:2990-2994.
Kruger et al., "Unusually tight aggregation in detonation nanodiamond: Identification and disintegration," Carbon, 2005, 43:1722-1730.
Kruger, "Hard and Soft: Biofunctionalized Diamond," Angewandte Chemie-International Edition, 2006, 45:6426-6427.
Lacerda et al., "Carbon nanotubes as nanomedicines: From toxicology to pharmacology," Advanced Drug Delivery Reviews, 2006, 58:1460-1470.
Lam et al. 2008. "Nanodiamond-Embedded Microfilm Devices for Localized Chemotherapeutic Elution." ACS Nano 2(10):2095-102.
Langer, New Methods of Drug Delivery, Science, 1990, 249:1527-1533.
Lankelma et al., "Doxorubicin Gradients in Human Breast Cancer," Clinical Cancer Research, 1999, 5:1703-1707.
Lee et al., "E ect of Oxygen Plasma Treatment on Adhesion Improvement of Au Deposited on Pa-c Substrates," Journal of the Korean Physical Society, 2004, 44:1177-1181.
Lee et al., "Reconstitution of energy convering proteins in biocompatible materials" IEEE 2003 Proceedings on Nanotechnology, 2:733-736.
Lee et al., "Vectorial insertion of bacteriorhodopsin for directed orientation assays in various polymeric biomembranes," Polymer, 2006, 47:2935-2941.
Lee, "Effect of non-univorm initial drug concentration distribution on the kinetics of drug release from glassy hydrogel matrices," Polymer Science, 1984, 25:973-978.
Legha et al., "Adriamycin Therapy by Continuous Intra venous Infusion in Patients with Metastatic Breast Cancer," Cancer, 1982, 49:1762-1766.
Legha et al., "Reduction of Doxorubicin Cardiotoxicity by Prolonged Continuous Intravenous Infusion," Annals of Internal Medicine, 1982, 96:133-139.
Liu et al., "Cell and molecular mechanisms of keratinocyte function stimulated by insulin during wound healing." BMC Cell Biol, 2009, 10:1, 15 pages.
Liu et al., Biocompatible and detectable carboxylated nanodiamond on human cell, Nanotechnology, 2007, 18:325102, 10 pages.
Liu et al., "Biocompatible and Detectable Carboxylated Nanodiamond on Human Cell." Nanotechnology, 2007, 18:325102.
Liu et al., "Effects of topical application of insulin on the wound healing in scalded rats." Chinese J Burns [Zhonghua Shao Shang Za Zhi.] 2004, 20(2):98-101.
Liu et al., "PEGylated Nanographene Oxide for Delivery of Water-Insoluble Cancer Drugs." J. Am. Chem. Soc., 2009, 130:10876-10877.
Lopez et al., "Immobilization of RGD peptides on stable plasma-deposited acrylic acid coatings for biomedical devices," Surface and Coatings Technology 2005, 200:1000-1004.
Lu et al., Modeling and Optimization of Drug Release from Laminated Polymer Matrix Devices, AIChE Journal, 1998, 44:1689-1696.
Luecke et al., "The glucocorticoid receptor blocks P-TEFb recruitment by NFkappaB to effect promoter-specific transcriptional repression" Genes Dev., 2005, 19:1116-1127.
Maeda et al., "Dexamethasone inhibits tumor necrosis factor-alpha-induced cytokine secretion from spiral ligament fibrocytes," Hearing Research 2005, 202:154:160.
Malafaya et al., "Natural-origin polymers as carriers and scaffolds for biomolecules and cell delivery in tissue engineering application," Advanced Drug Delivery Reviews, 2007, 59:207-233.
May and Westley, "Effects of Tamoxifen and 4-hydroxytamoxifen on the pNR-1 and pNR-2 Estrogen-Regulated RNAs in Human Breast Cancer Cells." J. Biol. Chem., 1987, 262:15894-15899.
MDDIadmin, MDDI Medical Device and Diagnostic Industry News Products and Suppliers, 2005, pp. 7.
Meier et al., "Reconstitution of Channel Proteins in (polymerized) ABA Tri-block Copolymer Membranes" Angew Chim Int Ed, 2000, 39:4599-4602.
Misra, "Magnetic nanoparticle carrier for targeted drug delivery: perspective, outlook and design." J Materials Science & Technology, 2008, 24(9):1011-9.

(56) References Cited

OTHER PUBLICATIONS

Mochalin and Gogotsi, "Wet Chemistry Route to Hydrophobic Blue Fluorescent Nanodiamond." J Am Chem Soc, 2009, 131(13):4594-5.
Nardin et al., "Giant Free-Standing ABA Triblock Copolymer Membranes" Langmuir, 2000, 16:7708-7712.
Nardin et al., "Polymerized ABA-tri-block copolymer vesicles" Langmuir, 2000, 16:1035-1041.
Neugart et al. 2007. "Dynamics of Diamond Nanoparticles in Solution and Cells." Nano Lett. 7, 3588-3591.
Neugart et al., "Dynamics of Diamond Nanoparticles in Solution and Cells," Nano Letters, 2007, 7:3588-3591.
Niemeyer, "Nanoparticles, proteins, and nucleic acids: biotechnology meets material science." Angew Chem Int Ed, 2001, 40(22):4128-58.
Osti, "Skin pH variations from the acute phase to re-epithelialization in burn patients treated with new materials (Burnshield, semipermeable adhesive film, Dermasilk, and Hyalomatrix). Non-invasive preliminary experimental clinical trial." Ann Burns and Fire Disasters, 2007, 21(2):73-7.
Ozawa et al., "Preparation and Behavior of Brownish, Clear Nanodiamond Colloids," Advanced Materials, 2007, 19:1201-1206.
Ozawa et al., "Preparation and Behavior of Brownish, Clear Nanodiamond Colloids." Adv. Mater., 2007, 19:1201-1206.
Panessa-Warren et al., "Biological cellular response to carbon nanoparticle toxicity." J Phys: Condens Matter, 2006, 18(33):S2185-S201.
Pantazis, "Preclinical Studies of Water-Insoluble Camptothecin Congeners: Cytotoxicity, Development of Resistance, and Combination Treatments." Clin. Canc. Res., 1995, 1:1235-1244.
Panyam and Labhasetwar, "Biodegradable nanoparticles for drug and gene delivery to cells and tissue." Adv Drug Deliv Rev., 2003, 55(3):329-47.
Pathak et al., "Nanosizing drug particles in supercritical fluid processing." J Am Chem Soc, 2004, 126(35):10842-3.
Pathak et al., "Supercritical fluid processing of drug nanoparticles in stable suspension." J Nanosci Nanotechnol, 2007, 7(7):2542-5.
Peer et al., "Nanocarriers as an emerging platform for cancer therapy," Nature Nanotechnology, 2007, 18:751-760.
Petrov and Shenderova, "Ultra Nanocrystalline Diamond: Synthesis, Properties and Applications" Shenderova, O.A.; Gruen, D.M., Eds.; William Andrew Publishing: New York; 2006, pp. 529-550.
Pierre et al., "Effects of insulin on wound healing." J Trauma, 1998, 44(2):342-5.
Pierstorff et al., "Nanoscale architectural tuning of parylene patch devices to control therapeutic release rates," Nanotechnology, 2008, 19:445104, 8 pages.
Priola et al., "Properties of polymeric films obtained from u.v. cured poly(ethylene glycol) diacrylates," Polymer, 1993, 34:3653-3657.
Puzyr et al., "Destruction of human blood cells in interaction with detonation nanodiamonds in experiments in vitro," Diamond and Related Materials, 2004, 13:2020-2023.
Puzyr et al., "Nanodiamonds with novel properties: A biological study." Diamond Relat Mater, 2007, 16(12):2124-8.
Rathman et al., "Biocomposite films synthesized at a fluid/fluid interface" Faraday Disc, 2005, 129:193-203.
Revzin et al., "Fabrication of Poly(ethylene glycol) Hydrogel Microstructures Using Photolithography," Langmuir, 2001, 17:5440-5447.
Rouanet et al., "Neoadjuvant Percutaneous 4-Hydroxytamoxifen Decreases Breast Tumoral Cell Proliferation: A Prospective Controlled Randomized Study Comparing Three Doses of 4-Hydroxytamoxifen Gel to Oral Tamoxifen." J. Clin. Onco., 2005, 23:2980-2987.
Sawhney et al., "Bioerodible Hydrogels Based on Photopolymerized Poly(ethylene glycol)-co-poly(alpha-hydroxy acid) Diacrylate Macromers," Macromolecules, 1993, 26:581-587.
Schneider et al., "Influence of pH on wound-healing: a new perspective for wound-therapy?" Arch Dermatol Res, 2007, 298(9):413-20.
Schrand et al., "Are Diamond Nanoparticles Cytotoxic?" J Phys Chem B, 2007, 111(1):2-7.
Scott & Peppas, "Highly crosslinked, PEG-containing copolymers for sustained solute delivery," Biomaterials, 1999, 20:1371-1380.
Sharma et al., "Optimizing Poly(cholor-p-Xylylene) or Parylene C Synthesis," Journal of Applied Polymer Science, 1988, 36:1555-1565.
Sheihet et al., "Hydrophobic Drug Delivery by Self-Assembling Triblock Copolymer-Derived Nanospheres." Biomacromol., 2005, 6:2726-2731.
Shu et al., "In situ crosslinkable hyaluronan hydrogels for tissue engineering," Biomaterials, 2004, 25:1339-1348.
Sokolsky-Papkov et al., "Polymer carriers for drug delivery in tissue engineering," 2007 Advanced Drug Delivery Reviews, 2007, 59:187-206.
Speller and Meot-Ner. 1985. "The ionic hydrogen bond and ion solvation. 3. Bonds involving cyanides. Correlations with proton affinities." J Phys Chem 89(24):5217-22.
Spellman et al., "Vacuum Deposition of Parylene Films: Influence of Process Factors and Baffling on Film-Thickness Distribution," Journal of Plastic Film and Sheeting, 1999, 15:308-328.
Stark, "Literature review: Biological safety of parylene C," 1996 Medical Plastics and Biomaterials, p. 30.
Stoeckenius et al., "Structure of biological membranes" Biochem. Biophys Acta, 1979, 505:215-278.
Subramani & Birch, "Fabrication of poly(ethylene glycol) hydrogel micropatterns with osteoinductive growth factors and evaluation of the effects on osteoblast activity and function," Biomedical Materials, 2006, 1:144-154.
Szucs et al., "Stable and Reversible Electrochemistry of Cytochrome-C on Bare Electrodes 0.2. Effects of Experimental Conditions" Journal of Electroanalytical Chemistry, 1995, 383:75-84.
Tannock et al., "Limited Penetration of Anticancer Drugs through Tumor Tissue: A Potential Cause of Resistance of Solid Tumors to Chemotherapy," Clinical Cancer Research, 2002, 8:878-884.
Tannock, "Tumor physiology and drug resistance," Cancer and Metastasis, 2001, 20:123-132.
Taylor et al., "Estrogen Receptor-mediated and Cytotoxic Effects of the Antiestrogens Tamoxifen and 4-Hydroxytamoxifen." Cancer Res., 1984, 44:1409-1414.
Terrettaz et al., "Kinetic Parameters for Cytochromec via Insulated Electrode Voltammetry" Journal of the American Chemical Society, 1996, 118:7857-7858.
Unger et al., "Poly(ethylene carbonate): A thermoelastic and biodegradable biomaterial fordrug eluting stent coatings?," Journal of Controlled Release 2007, 117:312-321.
Ushizawa et al., "Covalent immobilization of DNA on diamond and its verification by diffuse reflectance infrared spectroscopy," Chemical Physics Letters, 2002, 351:105-108.
Villerbu et al., "Cellular effects of purvalanol A: A specific inhibitor of cyclin-dependent kinase activities." Int. J.Canc., 2002, 97:761-769.
Volodkin et al., "Composite multilayered biocompatible polyelectrolyte films with intact liposomes: stability and temperature triggered dye release," Soft Matter, 2008, 4:122-130.
Wang et al., "Activation of nuclear factor-jB during doxorubicin-induced apoptosis in endothelial cells and myocytes is pro-apoptotic : the role of hydrogen peroxide," Biochemical Journal 2002, 367:729-740.
West & Hubbell, "Photopolymerized hydrogel materials for drug delivery applications," Reactive Polymers, 1995, 25:139-147.
Westedt et al., "Paclitaxel releasing films consisting of poly(vinyl alcohol)-graft-poly(lactide-co-glycolide) and their potential as biodegradable stent coatings," Journal of Controlled Release 2006, 111:235-246.
Wheatley et al., "Coated Alginate Microspheres: Factors Influencing the Controlled Delivery of Macromolecuels," Journal of Applied Polymer Science, 1991 43:2123-2135.
Williams et al., "Variable cytocompatibility of six cell lines with photoinitiators used for polymerizing hydrogels and cell encapsulation," Biomaterials, 2005, 26:1211-1218.
Wolgemuth, "Assessing the performance and suitability of parylene coating," 2000 Medical Device and Diagnostic Industry, Published

(56) References Cited

OTHER PUBLICATIONS

Aug. 1, 2000, retrieved from http://www.mddionline.com/article/assessing-performance-and-suitability-parylene-coating, Nov. 24, 2014, 7 pages.

Wong et al., "Chemotherapy with anticancer drugs encapsulated in solid lipid nanoparticles," Advanced Drug Delivery Reviews, 2007, 59:491-504.

Wood et al., "Controlling interlayer diffusion to achieve sustained, multiagent delivery from layer-by-layer thin films," Proceedings National Academy of Sciences, 2006, 103:10207-10212.

Wood et al., "Tunable Drug Release from Hydrolytically DegradableLayer-by-Layer Thin Films," Langmuir, 2005, 21:1603-1609.

Xi et al., "Lessons Learned From Engineering Biologically-Active Hybrid Nano/Micro-devices" Advanced Functional Materials, 2005, 15:1233-1240.

Xin et al., "A Segmentation Scheme Based on Rayleigh Distribution Model for Extracting Glottal Waveform from High-speed Laryngeal Images," Proceedings of the 2005 IEEE Engineering in Medicine and Biology Society, Sep. 1-4, 2005, pp. 6269-6272.

Xu et al., "Intracellular drug delivery by poly(lactic-co-glycolic acid) nanoparticles, revisited." Mol Pharm, 2009, 6(1):190-201.

Yamagishi, "Investigation of Plasma-Polymerized Films as Primers for Parylene-C Coatngs on Neural Prosthesis Materials," Thin Solid Films (Switzerland), 1991, 202:39-50.

Yang et al. 2002. "DNA-Modified Nanocrystalline Diamond Thin-Films as Stable, Biologically Active Substrates." Nat. Mater., 1, 253-257.

Yang et al., "DNA-modified nanocrystalline diamond thinfilms as stable, biologically active substrates," Nature Materials, 2002, 1:253-257.

Yang et al., "High deposition rate parylene films," Journal of Crystal Growth 1998, 183:385-390.

Yeap et al. "Using Detonation Nanodiamond for the Specific Capture of Glycoproteins," Analytical Chemistry, 2008, 80:4659-4665.

Yeap et al., "Detonation Nanodiamond: An Organic Platform for the Suzuki Coupling of Organic Molecules." Langmuir, 2009, 25(1):185-91.

Yeo et al., "In Situ Cross-linkable Hyaluronan Hydrogels Containing Polymeric Nanoparticles for Preventing Postsurgical Adhesions." Ann Surg, 2007, 245(5):819-24.

Yu et al., "Bright Fluorescent Nanodiamonds: No Photobleaching and Low Cytotoxicity," Journal of American Chemical Society, 2005, 127:17604-17605.

Zeng et al., "Poly(vinyl alcohol) Nanofibers by Electrospinning as a Protein Delivery System and the Retardation of Enzyme Release by Additional Polymer Coatings," Biomacromolecules 2005, 6:1484-1488.

Zhang et al., "Co-Delivery of Hydrophobic and Hydrophilic Drugs from Nanoparticle-Aptamer Bioconjugates." Chem Med Chem, 2007, 2:1268-1271.

Zhang et al., "Local insulin-zinc injection accelerates skin donor site wound healing." J Surg Res, 2007, 142(1):90-6.

Zhang et al., "Self-Assembled Lipid-Polymer Hybrid Nanoparticles: A Robust Drug Delivery Platform." ACS Nano, 2008, 2(8):1696-702.

Zhao et al., "Nanocrystalline diamond modified gold electrode for glucose biosensing." Biosens Bioelectron, 2006, 22(5):649-55.

Zheng et al., "A Novel Photoscissle Poly(ethylene glycol)-Based Hydrogel," Adv. Funct. Mater., 2001, 11:37-40.

Zheng et al., "Design of a Membrane Fluorescent Sensor Based on Photo-Cross-Linked PEG Hydrogel," Journal of Physical Chemistry B, 2003, 107:483-488.

\* cited by examiner

Nanodiamond     PEI800     Plasmid DNA

NANODIAMOND PARTICLE COMPLEXES

CROSS-REFERENCE TO RELATED APPLICATION

The present application is a Continuation-in-part of U.S. application Ser. No. 12/789,966, filed May 28, 2010, now abandoned, which claims priority to U.S. Provisional Patent Application Ser. No. 61/181,993 filed May 28, 2009, both of which are hereby incorporated by reference in their entireties.

The present application is also a Continuation-in-part of U.S. application Ser. No. 12/481,400 filed Jun. 9, 2009, which claims priority to U.S. Provisional Applications 61/059,976 and 61/059,979, both of which were filed Jun. 9, 2008; all of which are herein incorporated by reference in their entireties.

STATEMENT REGARDING FEDERALLY SPONSORED RESEARCH OR DEVELOPMENT

This invention was made with government support under Grant Nos. CMMI-0846323, CMMI-0856492, and DMI-0327077 (Subcontract from the University of California-Berkeley, Subcontract Number SA5880-21593) from the National Science Foundation, and Grant No. U54 AI065359 from the National Institutes of Health. The government has certain rights in the invention.

FIELD OF THE INVENTION

The present invention provides various functionalized nanodiamond particles. In some embodiments, the present invention provides complexes composed of nanodiamond particles and therapeutic agents. In certain embodiments, the present invention provides soluble complexes composed of nanodiamond particles and therapeutic agents that are water-insoluble or poorly water soluble. In some embodiments, the present invention provides complexes comprising nanodiamond particles and anthracycline and/or tetracycline compounds. In other embodiments, the present invention provides nanodiamond-nucleic complexes composed of polyethyleneimine surface functionalized nanodiamond particles and nucleic acid molecules. In further embodiments, the present invention provides alkaline-sensitive nanodiamond-protein complexes composed of nanodiamond particles and a protein adsorbed to the nanodiamond particles, where the protein is configured to desorb from the nanodiamond particles under sufficiently alkaline conditions. The present invention also provides materials and devices for the controlled release of therapeutics, and methods for uses thereof.

BACKGROUND

The application of nanoparticles as effective drug delivery vehicles, as well as in mechanical, electrical and MEMS applications has been demonstrated with carbon nanotubes, nanodiamonds, nanoparticle-embedded films, natural and synthetic polymers, lipid vesicles and a host of other nanoscale species [8, 9, 17-27]. Of these, detonated nanodiamonds are of interest primarily due to their small molecule loading capabilities [9, 28], functionalized surface [29] and biocompatibility [15, 30-32]. These attributes create a dynamic interface where the interactions between NDs and other particles or molecules can be defined by ND surface characteristics. An example of such an interaction is given by the supplied NDs possessing hydrophilic hydroxyl and carboxylic functional groups owing to characteristic surface charges and allowing for dispersion in water [8, 28, 29]. The future prospects of NDs in biomedical applications and their suggested biocompatibility manifests NDs as a favorable carbon-based biomaterial.

SUMMARY OF THE INVENTION

The present invention provides various functionalized nanodiamond particles. In some embodiments, the present invention provides complexes composed of nanodiamond particles and therapeutic agents. In certain embodiments, the present invention provides complexes composed of nanodiamond particles and therapeutic agents that are water-soluble, water-insoluble, or poorly water soluble. In certain embodiments, the present invention provides soluble complexes composed of nanodiamond particles and therapeutic agents that are water-insoluble or poorly water soluble. In some embodiments, nanodiamond particles exhibit high binding capacity for one or more therapeutic agents. In other embodiments, the present invention provides nanodiamond-nucleic complexes composed of polyethyleneimine surface functionalized nanodiamond particles and nucleic acid molecules. In further embodiments, the present invention provides alkaline-sensitive nanodiamond-protein complexes composed of nanodiamond particles and a protein adsorbed to the nanodiamond particles, where the protein is configured to desorb from the nanodiamond particles under sufficiently alkaline conditions. The present invention also provides materials and devices for the controlled release of therapeutics, and methods for uses thereof. In some embodiments, the present invention provides nanofilms, functionalized nanodiamonds, nanodiamond clusters, bilayer carrier/delivery elements, hydrogel delivery/carrier elements, and/or combinations thereof for the controlled release for the controlled release of therapeutics.

In some embodiments, the present invention provides compositions comprising a soluble complex, wherein the soluble complex comprises: a) a nanodiamond particle comprising one or more surface carboxyl groups; and b) a therapeutic agent, wherein the therapeutic agent is inherently water-insoluble or poorly water soluble (e.g., hydrophobic), wherein the therapeutic agent is adsorbed to the nanodiamond particle to form the soluble complex, and wherein the soluble complex is soluble in water (e.g., soluble in biological fluids, such as inside the human body) and suitable for in vivo administration to a human. In certain embodiments, the present invention provides compositions comprising a therapeutic agent adsorbed to a nanodiamond particle, wherein the nanodiamond particle comprises one or more surface carboxyl groups, wherein the therapeutic agent is water-insoluble or poorly water soluble when not adsorbed to the nanodiamond particle, and wherein the therapeutic agent is water soluble when adsorbed to the nanodiamond particle.

In some embodiments, the present invention provides compositions comprising a complex, wherein the complex comprises: a) a nanodiamond particle; and b) a therapeutic agent. In some embodiments, a therapeutic agent comprises a tetracycline class therapeutic. In some embodiments, a therapeutic agent comprises an anthracycline class therapeutic. In some embodiments, a therapeutic agent comprises one or more of daunorubicin, epirubicin, idarubicin, minocycline, tetracycline, oxytetracycline. In some embodiments, a therapeutic agent comprises one or more of daunorubicin, doxorubicin, epirubicin, idarubicin, valrubicin, mitoxantrone, tetracycline, chlortetracycline, oxytetracycline, demeclocycline, doxycycline, lymecycline, meclocycline, methacycline, minocycline, and/or rolitetracycline.

In other embodiments, the present invention provides methods of making a soluble complex comprising: mixing a nanodiamond particle with a therapeutic agent in the presence of an acid solution such that the therapeutic agent adsorbs to the nanodiamond particle thereby forming a soluble complex, wherein the therapeutic agent is inherently water-insoluble or poorly water soluble. In particular embodiments, the acid solution comprises acetic acid.

In some embodiments, the present invention provides compositions comprising a nanodiamond-nucleic acid complex, wherein the complex comprises: a) functionalized nanodiamond particles comprising one or more surface polyethyleneimine molecules; and b) nucleic acid molecules, wherein the nucleic acid molecules and the functionalized nanodiamond particles form a nanodiamond-nucleic acid complex.

In certain embodiments, the present invention provides methods of making a nanodiamond-nucleic acid complex comprising: a) mixing nanodiamond particles with polyethyleneimine molecules to generate functionalized nanodiamond particles; and b) mixing the functionalized nanodiamond particles with nucleic acid to generate a nanodiamond-nucleic acid complex.

In particular embodiments, the functionalized nanodiamond particles and the nucleic acid molecules form the nanodaimond-nucleic acid complex via attraction of positive charges on the functionalized nanodiamond particles and negative charges on the nucleic acid molecules. In other embodiments, the nucleic acid comprises DNA, RNA, a gene of interest, a microRNA, siRNA, or a plasmid. In particular embodiments, the nucleic acid molecules in the nanodiamond-nucleic acid complex are attached to the nanodiamond particles such that they are released upon cellular introduction. In certain embodiments, polyethyleneimine molecules are low molecular weight polyethyleneimine molecules.

In some embodiments, the present invention provides compositions comprising an alkaline-sensitive nanodiamond-protein complex, wherein the alkaline-sensitive nanodiamond complex comprises: a) a nanodiamond particle comprising one or more surface carboxyl or hydroxyl groups; and b) a protein (e.g., human insulin or other therapeutic protein), wherein the protein is adsorbed to the nanodiamond particle to form the alkaline-sensitive nanodiamond-protein complex, and wherein the protein is configured to desorb from the nanodiamond particle only under sufficiently alkaline conditions. In particular embodiments, the alkaline conditions are a pH of at least 8.0 . . . 8.5 . . . 9.0 . . . 9.5 . . . 10.0 . . . 10.5 . . . 11.0 . . . 12.0 . . . 13.0 . . . or 14.0.

In additional embodiments, the present invention provides methods of treating a subject comprising; a) providing: i) a subject comprising a treatment site that has an alkaline pH; and ii) a composition comprising an alkaline-sensitive nanodiamond complex, wherein the alkaline-sensitive nanodiamond complex comprises: A) a nanodiamond particle comprising one or more surface carboxyl or hydroxyl groups; and B) a protein, wherein the protein is adsorbed to the nanodiamond particle to form the alkaline-sensitive nanodiamond-protein complex; and b) administering (e.g., systemically, topically, orally, etc.) the composition to a subject under conditions such that: i) the alkaline-sensitive nanodiamond complex reaches the treatment site, and ii) the protein desorbs from the alkaline-sensitive nanodiamond complex in response to the alkaline pH at the treatment site. In particular embodiments, the alkaline conditions are a pH of at least 8.0 . . . 8.5 . . . 9.0 . . . 9.5 . . . 10.0 . . . 10.5 . . . 11.0 . . . 12.0 . . . 13.0 . . . or 14.0. In other embodiments, the treatment site is a wound and the administering is topical. In some embodiments, the protein comprises insulin (e.g., human insulin).

The present invention provides several classes of therapeutic delivery systems, devices, methods, materials, and compositions: (1) a nanofilm comprising: a base layer, wherein the base layer is composed of Parylene A, an elution layer, wherein, the elution layer is composed of Parylene A, and a therapeutic layer, wherein the therapeutic layer is composed of at least one therapeutic agent, and wherein the therapeutic layer is between the base layer and the elution layer; (2) a nanofilm comprising: a nanodiamond layer, wherein the nanodiamond layer is comprised of nanodiamonds functionalized with at least one therapeutic agent, a base layer, and an elution layer, wherein, the nanodiamond layer is between the base layer and the elution layer; (3) a composition comprising: a nanodiamond element, wherein the nanodiamond element comprises nanodiamonds functionalized with at least one therapeutic agent, and a carrier element, wherein the nanodiamond element is contained within the carrier element; (4) devices, methods, materials, and compositions comprising combinations, alterations, and/or modifications of all or portions (1)-(3) with elements disclosed herein or known to those of skill in the art.

In some embodiments, the present invention relates to localized nanodiamond elution through a nanofilm device. In some embodiments, the present invention provides nanodiamond-embedded nanofilm devices and methods for therapeutic uses thereof. In some embodiments, nanodiamonds functionalized with at least one therapeutic agent are embedded between two or more polymer layers, such as a base layer and a semi-permeable layer (e.g. elution layer). In some embodiments the base layer is thick (e.g. thicker than the semipermeable layer), rough, and impermeable. In some embodiments, the semi-permeable layer is thin (e.g. ultra-thin, nanometer scale, etc.). In some embodiments, the semi-permeable layer comprises nanopores through which the functionalized nanodiamonds are capable of eluting. In some embodiments, a nanofilm device can be used to deliver therapeutics to a subject through the elution of the therapeutic-functionalized nanodiamonds from the nanofilm (e.g. onto a surface of the subject (e.g. skin, mucous membrane, etc.) into a subject (e.g. body cavity, blood, etc.)).

Nanodiamonds (NDs) possess several characteristics that make them suitable for advanced drug delivery. Due to their high surface area to volume ratio and non-invasive dimensions, extremely high loading capacities of therapeutic are achievable. In addition, NDs are capable of interfacing with virtually any therapeutic molecule via physical interactions due to tailorable surface properties and compositions.

Embodiments of the present invention provide a nanofilm composition comprised of a nanodiamond layer, a base layer, and a semi-permeable layer. In some embodiments, the nanodiamond layer lies between the base layer and the semi-permeable layer, and is comprised of nanodiamonds functionalized with at least one therapeutic agent.

In some embodiments of the present invention, a therapeutic agent functionalized with nanodiamonds comprises, but is not limited to: sirtuin activators, cytokines (e.g. interferons of all kinds, e.g. alpha, beta, gamma, etc.), thrombin inhibitors, antithrombogenic agents, thrombolytic agents, fibrinolytic agents, vasospasm inhibitors, calcium channel blockers, vasodilators, antihypertensive agents, antimicrobial agents, antibiotics, inhibitors of surface glycoprotein receptors, antiplatelet agents, antimitotics, microtubule inhibitors, anti secretory agents, actin inhibitors, remodeling inhibitors, antisense nucleotides, anti metabolites, antiproliferatives, anticancer chemotherapeutic agents, anti-inflammatory steroid or non-steroidal anti-inflammatory agents, immunosuppressive agents, growth hormone antagonists, growth factors, dopamine agonists, radiotherapeutic agents, extracellular matrix components, inhibitors, free radical scavengers, chelators, antioxidants, anti polymerases, antiviral agents, photodynamic therapy agents, and gene therapy agents. In some embodiments where the therapeutic agent is an anti-inflammatory compound, the therapeutic agent can be dexamethasone, glucocorticoid, or an LXR agonist. In some embodiments where the therapeutic agent is an anticancer chemotherapeutic agent, the therapeutic agent can be doxorubicin (DOX).

In some embodiments of the present invention, the base layer may comprise Parylene (e.g. Parylene A or Parylene C), and more particularly may comprise Parylene C. Likewise, the semi-permeable layer may comprise Parylene (e.g. Parylene A or Parylene C), and more particularly may comprise Parylene C. In embodiments in which the base and/or semi-permeable layers are comprised of Parylene, the Parylene may be treated with oxygen plasma. In some embodiments, the base and/or semi-permeable layers may contain added $CO_3^-$ and carbonyl (C=O) groups. Other treatments understood by one in the art may also be made to the Parylene material.

Parylene refers to a variety of polyxylene polymers marketed by several providers, including Para Tech Coating, Inc., Specialty Coating Systems, Inc., and others. Parylene N is a polymer manufactured from di-p-xylylene, a dimer synthesized from p-xylene. Di-p-xylylene, more properly known as (2.2)paracyclophane, is made from p-xylene in several steps involving bromination, amination and elimination. There are a number of derivatives and isomers of Parylene, but only a few are typically used commercially, e.g. Parylene C and Parylene D.

In some embodiments, a single layer of the nanofilm may be designed to have a thickness from about 1 nm to about 10 nm, desirably less than about 4 nm, although dimensions outside this range are contemplated. However, the nanofilm may include multiple layers (e.g., from about 2 to about 10 layers) of the therapeutic agent complexes, wherein each layer has a thickness from about 1 to about 10 nm (e.g., about 4 nm or less). The functionalized nanodiamonds may be approximately 2-8 nm in diameter, although other dimensions are contemplated.

In some embodiments of the present invention, the semi-permeable layer contains nanopores. The nanodiamond layer is configured to elute through the nanopores in the semi-permeable layer. In some embodiments, nanodiamonds functionalized with at least one therapeutic agent are configured to elute through nanopores in the semi-permeable layer, but the nanodiamod layer is incapable of elution through the base layer.

In some embodiments of the present invention, the nanoflim composition, comprised of a nanodiamond layer, a base layer and a semi-permeable layer, is flexible. In some embodiments, the nanofilm composition is fashioned as a transdermal patch.

In some embodiments, the present invention provides a medical device with one or more of its surfaces coated with any of the nanofilm compositions described herein. The medical device may be implantable. In some embodiments the medical device contains an electrode. The nanofilm coatings of the present invention may be used on a variety of medical substrates, including an implantable medical device. Such medical devices may be made of a variety of biocompatible materials including, but not limited to, polymers and metals. Medical substrates onto which the nanofilms may be coated include, neural/cardiovascular/retinal implants, leads and stents, and dental implants (e.g., nanofilms to seed bone growth). In some embodiments, the nanofilm may be coated onto the electrode of an implantable medical device. In fact, coating the present nanofilms onto an electrode is contemplated to provide important medical advantage because the nanofilm is contemplated to prevent or minimize bio-fouling which often begins at the site of a metal electrode. In addition, unlike more conventional implant coatings, the present nanofilms may be made thin enough that they do not interfere with electrode function (e.g., electrical conductivity or redox reactions at electrodes). Other medical device uses and configurations will be understood by one skilled in the art using the principles described herein.

In some embodiments, the present invention provides a method of delivering a therapeutic agent to a target site in a subject, in which any nanofilm composition described herein, is administered to the subject near a target site. Elution of the therapeutic agent from the nanofilm device delivers the therapeutic agent to the target site. The nanofilm composition may comprise a transdermal patch or coat a medical device, or other desired application. In embodiments where the nanofilm coats a medical device, that medical device may be implantable within a subject. The therapeutic agent delivered by the method of the present invention includes, but is not limited to: thrombin inhibitors, antithrombogenic agents, thrombolytic agents, fibrinolytic agents, vasospasm inhibitors, calcium channel blockers, vasodilators, antihypertensive agents, antimicrobial agents, antibiotics, inhibitors of surface glycoprotein receptors, antiplatelet agents, antimitotics, microtubule inhibitors, anti secretory agents, actin inhibitors, remodeling inhibitors, antisense nucleotides, anti metabolites, antiproliferatives, anticancer chemotherapeutic agents, anti-inflammatory steroid or non-steroidal anti-inflammatory agents, immunosuppressive agents, growth hormone antagonists, growth factors, dopamine agonists, radiotherapeutic agents, extracellular matrix components, inhibitors, free radical scavengers, chelators, antioxidants, anti polymerases, antiviral agents, photodynamic therapy agents, and gene therapy agents.

A semi-permeable layer of a device of the present invention may be selected to optimize drug elution rates, so as to provide optimal drug delivery for a particular drug type and therapy type. Selection of the size and shape of the nanopores and the nature of the polymer material may be tailored to optimize drug release characteristics.

In some embodiments of the present invention, the devices are used to harness intelligent drug release activity by releasing algorithmically/search scheme derived optimum concentrations of drugs for any medical or cosmetic to deliver a personalized medical treatment strategy. In some embodiments, this device is used to harness any search algorithm, including but not limited to simulated annealing, genetic algorithms, ant colony optimization, and the Gur Game including all other algorithms. In some embodiments the devices are functionalized with any therapeutically relevant molecule as well as sequestering matrix to enable slow and targeted release based upon a broad range of stimuli including but not limited to temperature, pH, light, salt concentrations, chemical stimuli, etc.

In some embodiments therapeutics that are released include but are not limited to conventional chemically synthesized drugs for anti-inflammation, chemotherapy, anti-angiogenesis, wound/burn healing, pain management, membrane repair, anti-coagulation, anti-infection/anti-bacterial/anti-viral applications, etc. In some embodiments a device of the present invention carries RNAi-based therapeutics and stabilizes RNAi molecules to enable sustained/long-term release with enhanced efficacy, as well as protein, small molecule, and antibody-based therapies, etc. In some embodiments the present invention also has applicability towards cosmetic applications by delivering anti-wrinkle, anti-acne, acid treatment, collagen, micro/nanobead, moisturizing, traditional eastern medicine ingredients as well as virtually any other cosmetic agent that can be employed. In some embodiments sequestering matrices that can be carried include nanodiamonds, block copolymers, polymer matrices, crosslinked networks, hydrogels, polymer amphiphiles, peptide amphiphiles, nanotubes made of carbon or polymers, carbon nanohorns, as well as the entire spectrum of carbon-based nanomaterials, metallic nanoparticles, silica nanoparticles, protein-based nanoparticles, nucleic acid-based nanoparticles, etc.

In some embodiments, the present invention relates to delivery of therapeutics through a functionalized nanofilm device. In some embodiments, the present invention provides an amine functionalized poly-p-xylene (Parylene) nanofilm device and methods for localized delivery of therapeutics thereof. In some embodiments, a layer comprised of at least one therapeutic agent is embedded between two or more Parylene A layers, such as a base layer and an elution layer. In some embodiments, the base layer is thick (e.g. thicker than an elution layer) and/or impermeable. In some embodiments, the elution layer (e.g. semi-permeable layer, permeable layer, etc.) is thin and/or contains openings (e.g., pores, pinholes, etc.) through which the therapeutic agent or agents are capable of eluting. In some embodiments, a Parylene A nanofilm device can be used to deliver therapeutics to a subject through the elution of the therapeutic agent from the nanofilm. In some embodiments, the amine functionalized Parylene A provides reactive groups on the surface of a Parylene A nanofilm. It is contemplated that the availability of free amine groups on the Parylene A surface provides a range of modifications which can be incorporated into the nanofilm, for example, through the conjugation of other molecules to the amine groups.

In some embodiments, the present invention provides a nanofilm composition comprised of a Parylene A base layer, a Parylene A elution layer, and a therapeutic layer. The therapeutic layer lies between the base layer and the elution layer, and is comprised of at least one therapeutic agent. In some embodiments of the present invention, the therapeutic agent within the therapeutic layer comprises, but is not limited to: thrombin inhibitors, antithrombogenic agents, thrombolytic agents, fibrinolytic agents, vasospasm inhibitors, calcium channel blockers, vasodilators, antihypertensive agents, antimicrobial agents, antibiotics, inhibitors of surface glycoprotein receptors, antiplatelet agents, antimitotics, microtubule inhibitors, anti secretory agents, actin inhibitors, remodeling inhibitors, antisense nucleotides, anti metabolites, antiproliferatives, anticancer chemotherapeutic agents, anti-inflammatory steroid or non-steroidal anti-inflammatory agents, immunosuppressive agents, growth hormone antagonists, growth factors, dopamine agonists, radiotherapeutic agents, extracellular matrix components, inhibitors, free radical scavengers, chelators, antioxidants, anti polymerases, antiviral agents, photodynamic therapy agents, and gene therapy agents. In some embodiments where the therapeutic agent is an anti-inflammatory compound, the therapeutic agent can be dexamethasone, glucocorticoid, or an LXR agonist. In some embodiments where the therapeutic agent is an anticancer chemotherapeutic agent, the therapeutic agent can be doxorubicin (DOX).

In some embodiments, a single layer of the nanofilm may be designed to have a thickness from about 1 nm to about 10 nm, desirably less than about 4 nm, although dimensions outside this range are contemplated (e.g. 15 nm, 25 nm, 50 nm, 100 nm, etc.). However, the nanofilm may include multiple layers (e.g., from about 2 to about 10 layers, 5 to 15 layers, 10 to 50 layers, etc.) of the therapeutic agent complexes, wherein each layer has a thickness from about 1 to about 10 nm (e.g., about 4 nm or less), although dimensions outside this range are contemplated.

In some embodiments of the present invention, the elution layer contains openings (e.g., pinholes, pores, etc.). In embodiments where the elution layer contains pinholes, the elution layer may exhibit some degree of permeability (e.g. semi-permeable, permeable, etc.). The therapeutic layer can be provided with a therapeutic agent or agents that elute through pinholes in the elution layer. In some embodiments, at least one therapeutic agent is configured to elute through pinholes in the elution layer. In some embodiments, the therapeutic layer, and any therapeutic agent or agents therein, are incapable of elution through the base layer. An elution layer of a device of the present invention may be selected to optimize drug elution rates, so as to provide optimal drug delivery for a particular drug type and therapy type. Selection of the size and shape of the pinholes and the nature of the polymer material may be tailored to optimize drug release characteristics.

In some embodiments, the present invention provides a nanofilm composition comprising: (a) a base layer, wherein the base layer is composed of Parylene A, (b) an elution layer, wherein, the elution layer is composed of Parylene A, and (c) a therapeutic layer, wherein the therapeutic layer is composed of at least one therapeutic agent, and wherein the therapeutic layer is between the base layer and the elution layer. In some embodiments, at least one therapeutic agent is selected from the group consisting of: thrombin inhibitors, antithrombogenic agents, thrombolytic agents, fibrinolytic agents, vasospasm inhibitors, calcium channel blockers, vasodilators, antihypertensive agents, antimicrobial agents, antibiotics, inhibitors of surface glycoprotein receptors, antiplatelet agents, antimitotics, microtubule inhibitors, anti secretory agents, actin inhibitors, remodeling inhibitors, antisense nucleotides, anti metabolites, antiproliferatives, anticancer chemotherapeutic agents, anti-inflammatory steroid or non-steroidal anti-inflammatory agents, immunosuppressive agents, growth hormone antagonists, growth factors, dopamine agonists, radiotherapeutic agents, extracellular matrix components, inhibitors, free radical scavengers, chelators, antioxidants, anti polymerases, antiviral agents, photodynamic therapy agents, and gene therapy agents. In some embodiments, the anti-inflammatory compound is dexamethasone (DEX), glucocorticoid, or an LXR agonist. In some embodiments, the anticancer chemotherapeutic agent is doxorubicin (DOX). In some embodiments, the elution layer is semi-permeable. In some embodiments, the therapeutic layer is configured to elute through said elution layer.

In some embodiments, the present invention provides a nanofilm composition comprising: (a) a nanodiamond layer, wherein the nanodiamond layer is comprised of nanodiamonds functionalized with at least one therapeutic agent, (b)

a base layer, and (c) an elution layer, wherein, the nanodiamond layer is between the base layer and the elution layer. In some embodiments, the said at least one therapeutic agent is selected from the group consisting of: thrombin inhibitors, antithrombogenic agents, thrombolytic agents, fibrinolytic agents, vasospasm inhibitors, calcium channel blockers, vasodilators, antihypertensive agents, antimicrobial agents, antibiotics, inhibitors of surface glycoprotein receptors, antiplatelet agents, antimitotics, microtubule inhibitors, anti secretory agents, actin inhibitors, remodeling inhibitors, antisense nucleotides, anti metabolites, antiproliferatives, anticancer chemotherapeutic agents, anti-inflammatory steroid or non-steroidal anti-inflammatory agents, immunosuppressive agents, growth hormone antagonists, growth factors, dopamine agonists, radiotherapeutic agents, extracellular matrix components, inhibitors, free radical scavengers, chelators, antioxidants, anti polymerases, antiviral agents, photodynamic therapy agents, and gene therapy agents. In some embodiments, the anti-inflammatory compound is dexamethasone, glucocorticoid, or an LXR agonist. In some embodiments, the anticancer chemotherapeutic agent is doxorubicin (DOX). In some embodiments, the base layer comprises a Parylene compound. In some embodiments, the elution layer comprises a Parylene compound. In some embodiments, the nanodiamond layer is configured to elute through the elution layer.

In some embodiments, the present invention provides a composition comprising: (a) a nanodiamond element, wherein the nanodiamond element is comprised of nanodiamonds functionalized with at least one therapeutic agent; and (b) a carrier element, wherein the nanodiamond element is contained within the carrier element. In some embodiments, the at least one therapeutic agent is selected from the group consisting of: thrombin inhibitors, antithrombogenic agents, thrombolytic agents, fibrinolytic agents, vasospasm inhibitors, calcium channel blockers, vasodilators, antihypertensive agents, antimicrobial agents, antibiotics, inhibitors of surface glycoprotein receptors, antiplatelet agents, antimitotics, microtubule inhibitors, anti secretory agents, actin inhibitors, remodeling inhibitors, antisense nucleotides, anti metabolites, antiproliferatives, anticancer chemotherapeutic agents, anti-inflammatory steroid or non-steroidal anti-inflammatory agents, immunosuppressive agents, growth hormone antagonists, growth factors, dopamine agonists, radiotherapeutic agents, extracellular matrix components, inhibitors, free radical scavengers, chelators, antioxidants, anti polymerases, antiviral agents, photodynamic therapy agents, and gene therapy agents. In some embodiments, the anti-inflammatory compound is dexamethasone, glucocorticoid, or an LXR agonist. In some embodiments, the anticancer chemotherapeutic agent is doxorubicin (DOX). In some embodiments, the carrier element comprises a PEG hydrogel. In some embodiments, the carrier element is semi-permeable. In some embodiments, the therapeutic element is configured to elute through the carrier element.

DESCRIPTION OF THE DRAWINGS

(FIGS. 3A-3C): Average particle size of all drugs decreased upon physisorption to NDs. (FIGS. 3D-3F): The zeta potential of all samples became more positive upon complexing with NDs.

DETAILED DESCRIPTION

Figure 1:
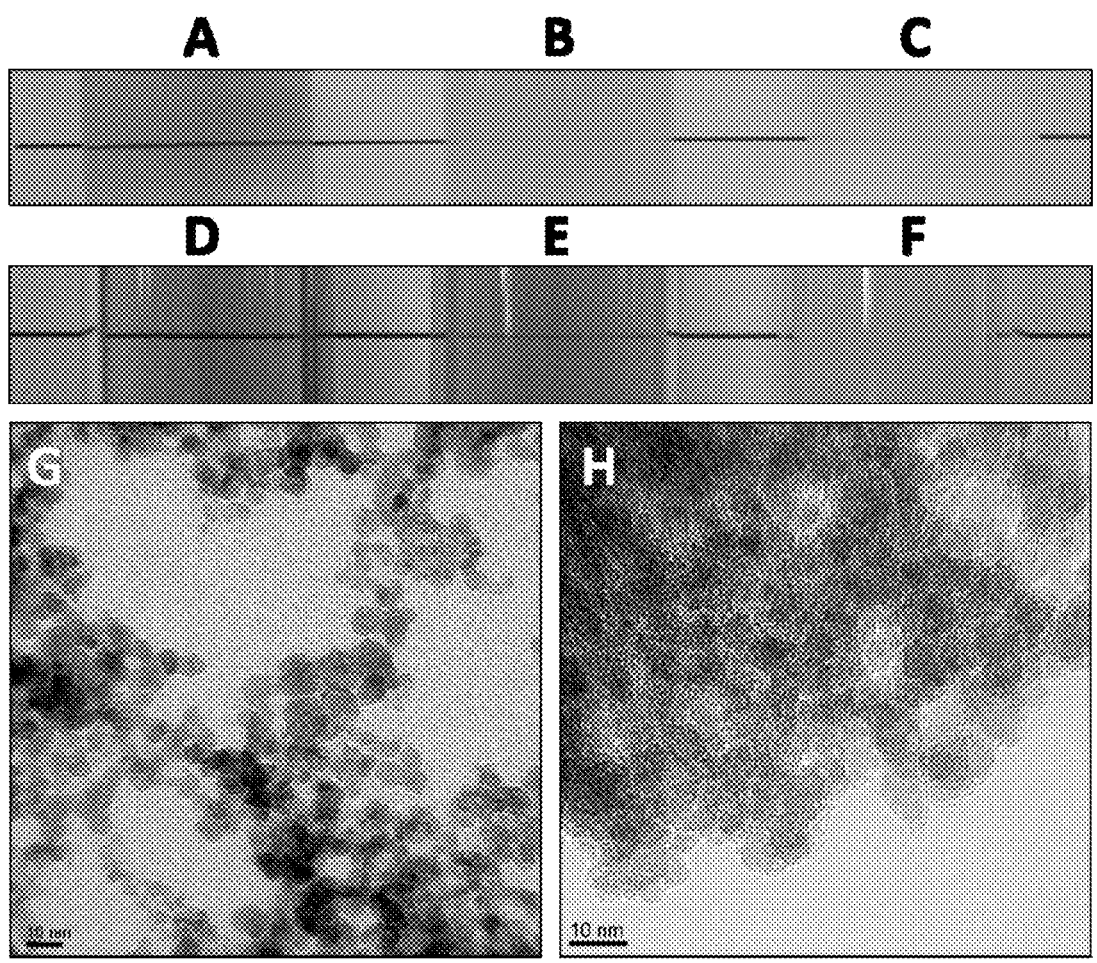
FIG. 1. NDs enhance the ability to disperse Purvalanol A and 4-OHT in water. Vials were prepared against background and the reduction in turbidity mediated by the NDs was confirmed under the following conditions: A) 1 mg/ml ND in 5% DMSO in water; B) 1 mg/ml ND, 0.1 mg/ml Purvalanol A in 5% DMSO in water; C) 0.1 mg/ml Purvalanol A in 5% DMSO in water; D) 1 mg/mL ND in 25% DMSO in water; E) 1 mg/mL ND, 0.1 mg/mL 4-OHT in 25% DMSO in water; F) 0.1 mg/mL 4-OHT in 25% DMSO in water. G) TEM image of pristine NDs. H) 4-OHT residue can be observed on the ND surface to confirm ND-drug interactions. Scale bars represent 10 nm.

The present invention provides various functionalized nanodiamond particles. In certain embodiments, the present invention provides soluble complexes composed of nanodiamond particles and therapeutic agents that are water-insoluble or poorly water soluble. In some embodiments, the present invention provides complexes comprising nanodiamond particles and anthracycline and/or tetracycline compounds. In other embodiments, the present invention provides nanodiamond-nucleic complexes composed of polyethyleneimine surface functionalized nanodiamond particles and nucleic acid molecules. In further embodiments, the present invention provides alkaline-sensitive nanodiamond-protein complexes composed of nanodiamond particles and a protein adsorbed to the nanodiamond particles, where the protein is configured to desorb from the nanodiamond particles under sufficiently alkaline conditions.

The present invention also provides compositions, materials, and devices for the controlled release of therapeutics, and methods for uses thereof. In particular, the present invention provides a therapeutic element and a carrier and/or delivery element. In some embodiments, a carrier/delivery element provides a means for applying one or more therapeutic elements to a device, surface, material, composition, tissue, or subject. In some embodiments, a carrier/delivery element provides the controlled release of one or more therapeutic elements onto, into, or from the surface of a device, surface, material, composition, tissue, or subject upon which it is applied.

I. Nano Diamond-Drug Complexes

In some embodiments, the present invention provides complexes composed of nanodiamond particles and therapeutic agents. In certain embodiments, the present invention provides complexes of nanodiamond particles with therapeutic agents that are water-soluble, water-insoluble, or poorly water soluble. In certain embodiments, the present invention provides soluble complexes of nanodiamond particles with therapeutic agents that are water-insoluble or poorly water soluble. In some embodiments, the present invention provides complexes of nanodiamond particles with anthracycline- and/or tetracycline-class therapeutics (e.g. anthracycline, tetracycline, daunorubicin, epirubicin, idarubicin, minocycline, tetracycline, oxytetracycline, etc.). In some embodiments, nanodiamond particles exhibit high binding capacity for one or more therapeutic agents.

A broad array of water insoluble compounds have displayed therapeutically-relevant properties towards a spectrum of medical and physiological disorders including cancer and inflammation. However, the continued search for scalable, facile, and biocompatible routes toward mediating the dispersal of these compounds in water has limited their widespread application in medicine. Experiments performed during development of the present invention demonstrate a platform approach of water-dispersible, nanodiamond cluster-mediated interactions with several exemplary therapeutics to enhance their suspension in water with preserved functionality, thereby enabling novel treatment paradigms that were previously unrealized. These therapeutics include Purvalanol A, a highly promising compound for hepatocarcinoma (liver cancer) treatment; 4-Hydroxytamoxifen (4-OHT), an emerging drug for the treatment of breast cancer; and Dexamethasone, a clinically relevant anti-inflammatory that has addressed an entire spectrum of diseases that span complications from blood and brain cancers to rheumatic and renal disorders. Any water-insoluble or poorly water soluble therapeutic may be employed. Exemplary water insoluble agents include: for example: allopurinol, acetohexamide, benzthiazide, chlorpromazine, chlordiazepoxide, haloperidol, indomethacine, lorazepam, methoxsalen, methylprednisone, nifedipine, oxazepam, oxyphenbutazone, prednisone, prednisolone, pyrimethamine, phenindione, sulfisoxazole, sulfadiazine, temazepam, sulfamerazine, and/or trioxsalen. Water-insoluble, poorly water soluble, or lipid soluble therapeutics which find use in embodiments of the present invention include central nervous system drugs, peripheral nervous system drugs, sensory organ drugs, cardiovascular system drugs, respiratory system drugs, hormones, urogenital system drugs, drugs for anal diseases, vitamins, drugs for liver diseases, antigout drugs, enzymes, antidiabetics, immunosuppressants, cytoactivators, antitumoral drugs, radioactive drugs, antiallergic drugs, antibiotics, chemotherapeutic agents, biological drugs, and extracorporeal diagnostic agents. More particularly, water-insoluble, poorly water soluble, and/or lipid soluble therapeutics that find use in ND-complexes of the present invention include steroidal drugs (e.g. dexamethasone, prednisolone, betamethasone, beclomethasone propionate, triamcinolone, hydrocortisone, fludrocortisone and prasterone, salts thereof, and their lipid-soluble derivatives), β-adrenergic agonists (e.g. procaterol, orciprenaline, isoproterenol hydrochloride, pirbuterol, terbutaline, hexoprenaline, fenoterol hydrobromide, hexoprenaline sulfate, terbutaline sulfate, salbutamol sulfate, oxyprenaline sulfate, formoterol fumarate, isoprenaline hydrochloride, pirbuterol hydrochloride, procaterol hydrochloride, mabuterol hydrochloride, and tulobuterol, salts thereof, and their lipid-soluble derivatives), xanthine derivatives (e.g. diprophylline, proxyphylline, aminophylline and theophylline, salts thereof, and their lipid-soluble derivatives), antibiotics (e.g. pentamidine isethionate, cefmenoxime, kanamycin, fradiomycin, erythromycin, josamycin, tetracycline, minocycline, chloramphenicol, streptomycin, midecamycin, amphotericin B, itraconazole and nystatin, salts thereof, and their lipid-soluble derivatives), and therapeutics of other classes (e.g. ipratropium bromide, methylephedrine hydrochloride, trimethoquinol hydrochloride, clenbuterol hydrochloride, oxitropium bromide, fultropium bromide, methoxyphenamine hydrochloride, clorprenaline hydrochloride sodium cromoglycate, etc.). In some embodiments, a complex is based upon NDs and a combination of two or more of the above listed agents or other agents understood by those in the art (e.g. 2 therapeutic agents, 3 therapeutic agents, 4 therapeutic agents, 5 therapeutic agents . . . 10 therapeutic agents . . . 20 therapeutic agents, etc.). Given the scalability of nanodiamond processing and functionalization, this approach serves as a facile, broadly impacting and significant route to translate water-insoluble compounds towards treatment-relevant scenarios.

Many biomedically-relevant compounds are difficult to solubilize in water, thus limiting their therapeutic potential [1-5]. These compounds have displayed remarkable therapeutic properties in vitro towards diseases such as liver and breast cancer [1-2]. However, since these therapeutics are soluble primarily in solvents generally regarded as unsuitable for injection, the realization of new routes to patient treatment enabled by these drugs has been hindered. As there remains a widespread need to package these compounds for facile delivery, a spectrum of polymeric and carbon-based nanomaterials have been explored [6-15]. For example, block copolymer-stabilized nanoemulsions have recently been explored as vehicles for polar and nonpolar agents [6]. Furthermore, lipid-polymer hybrid nanoparticles comprised of lipid-PEG shells and a poly(lactic-co-glycolic acid) (PLGA) hydrophobic core have been developed for the release of drugs that are poorly water soluble [7]. With regards to carbon-based strategies for the dispersal of poorly water-soluble drugs, PEGylated nano-graphene oxides have recently been explored for the delivery of an aromatic camptothecin (CPT) analog [15].

Nanodiamonds (NDs) represent an important, emerging class of materials that possess several medically-significant properties [16-36]. To produce highly uniform particle diameters of 4-6 nm, NDs can be inexpensively processed via ultrasonication, centrifugation, and milling methodologies [22,26]. Furthermore, acid treatment to remove impurities can simultaneously result in carboxyl group surface functionalization which can be harnessed towards subsequent drug interfacing. In addition, surface-bound carboxyl groups enable stable ND suspension in water. Therefore, these streamlined processes provide a rapid, inexpensive, and highly efficient approach towards making NDs scalable materials for medicine. Previous studies of NDs have demonstrated their carrier capabilities with Doxorubicin, cellular internalization without the need to coat the NDs with biocompatible or lipophilic agents, and preservation of drug efficacy upon murine macrophage and human colon cancer cell lines. Furthermore, comprehensive biocompatibility assays using quantitative real-time polymerase chain reaction (RT-PCR) interrogation of inflammatory cytokines have revealed their biocompatible properties.[26] During development of embodiments of the present invention is has been shown that ND clusters are additionally capable of complexing with poorly water-soluble drugs to enhance their dispersive properties in water. To demonstrate the platform capabilities of the NDs, three drugs with important implications (Purvalanol A, 4-hydroxytamoxifen), or demonstrated relevance (Dexamethasone) served as model systems.

Nanodiamonds provide a platform for the facile solubilization of a broad range of small molecule, protein, antibody, and RNA/DNA therapies. The present invention is not limited by the therapeutic agent that is employed. Work conducted during development of embodiments of the present invention has shown that nanodiamond powder platforms can be applied towards the rapid water solubilization of a broad range of therapeutic compounds that are currently translationally challenged because of their insolubility in water alone (e.g. currently soluble in DMSO, Ethanol, all solvents which preclude human use). By adding a small amount of acid (e.g., 1% or less) during the functionalization/drug-linking process, which we have demonstrated the linking of compounds such as 4-hydroxytamoxifen (4-OHT, a Breast Cancer therapeutic soluble in Ethanol), Purvalanol A (Liver cancer therapeutic soluble in DMSO), and Dexamethasone (Anti-inflammatory soluble in ethanol/methanol). The acid functionalization process is not toxic to cells as shown by proliferation assays, and there is a very minute and brief change in pH that is rapidly restored to normal levels within a few hours. This is a highly scalable process given the very economical characteristics of nanodiamond production, purification, and functionalization. Furthermore, in certain embodiments, this is a one step process and can be completed in minutes, making this perhaps among the most scalable processes for the solubilization of water insoluble drugs. Given the vast array of already known and undiscovered compounds with transformative treatment potential, but prohibitive water insolubility, the present invention meets the goals of optimized drug solubilization by being biocompatible, economical/scalable, and very rapid in terms of processing speed.

Many potentially useful pharmaceuticals cannot be used for clinical application due to toxicity. In some embodiments, the present invention provides complexes composed of nanodiamond particles and toxic or potentially toxic therapeutic agents. In some embodiments, complexing the therapeutic agent to the nanodiamond particles reduces drug toxicity and renders the drug safe for clinical application.

In some embodiments, the present invention provides complexes of nanodiamond particles and vaccines. In some embodiments, the present invention provides delivery and sustained release of one or more vaccines into a subject. In some embodiments, release of vaccine from complexes of the present invention reduces side effects from vaccine delivery, and enhances efficiency of vaccine delivery. In some embodiments, vaccines which find use with the present invention include, but are not limited to: influenza vaccine, cholera vaccine, bubonic plague vaccine, polio vaccine, hepatitis A vaccine, rabies vaccine, yellow fever, measles/mumps/rubella, typhoid vaccine, tetanus vaccine, diphtheria vaccine, *Mycobacterium tuberculosis* vaccine, etc.

In some embodiments, the present invention provides complexes of nanodiamond particles and one or more antimicrobial agents. In some embodiments, the present invention provides delivery and sustained release of one or more antimicrobial agents into a subject. In some embodiments, release of antimicrobial agent from complexes of the present invention reduces side effects and enhances efficiency of antimicrobial delivery. In some embodiments, antimicrobial agents which find use with the present invention include, but are not limited to: antibiotics, antivirals, antifungals, and antiparasitics.

In some embodiments, the present invention provides complexes of nanodiamond particles and anthracycline- and/or tetracycline-class therapeutics (e.g. anthracycline, tetracycline, daunorubicin, epirubicin, idarubicin, minocycline, tetracycline, oxytetracycline, etc.). In some embodiments, anthracycline- and/or tetracycline-class therapeutics, or derivatives thereof, are water-insoluble or have poor solubility in water. In some embodiments, anthracycline- and/or tetracycline-class therapeutics, or depravities thereof, are water soluble. In some embodiments ND-anthracycline complexes and/or ND-tetracycline complexes exhibit remarkable binding capacity between the ND surface and therapeutic compounds. Experiments conducted during development of embodiments of the present invention demonstrate exceptional binding between the ND surface and therapeutic compounds in ND complexes with therapeutics including daunorubicin, epirubicin, idarubicin, minocycline, tetracycline, oxytetracycline. In some embodiments, complexes between NDs and one or more any suitable anthracycline- and/or tetracycline class therapeutic exhibit high binding capacity. In some embodiments, complexes are based upon NDs and one, or any combination, of anthracyclines (e.g. daunorubicin, doxorubicin, epirubicin, idarubicin, valrubicin, mitoxantrone, etc.) and tetracyclines (e.g. tetracycline, chlortetracycline, oxytetracycline, demeclocycline, doxycycline, lymecycline, meclocycline, methacycline, minocycline, rolitetracycline). Experiments conducted during development of embodiments of the present invention have demonstrated that ND/anthracycline-class complexes and/or ND/tetracycline-class complexes bind in a very tight fashion while remaining dispersed in water. Although the present invention is not limited to any particular mechanism of action and an understanding of the mechanism of action is not necessary to practice the present invention, it is contemplated that opposite charges between the surface of acid washed NDs and the therapeutic compounds result in high potency binding following NaOH or KOH treatment. In some embodiments, drug release from ND/anthracycline-class complexes and/or ND/tetracycline-class complexes occurs in a sustained fashion. Experiments conducted during development of embodiments of the present invention have demonstrated that for drug-resistant disease models (e.g. cancer), the very tight ND-drug binding allows the drug to be ferried into the cell, and resistance can be counter-acted as the NDs maintain intracellular drug presence. As such, drug ejection/efflux is prevented. In some embodiments, ND/anthracycline-class complexes and/or ND/tetracycline-class complexes provide effective treatment of multi-drug resistant diseases such (e.g. cancer, tuberculosis, bacterial infections, etc.). In some embodiments, ND/anthracycline-class complexes and/or ND/tetracycline-class complexes provide effective treatment of multi-drug resistant diseases such (e.g. cancer, tuberculosis, bacterial infections, etc.) because drug ejection/efflux from cells is prevented.

The present invention is generally applicable to an extremely broad spectrum of treatment strategies, from cancer, to inflammation, to regenerative medicine, etc. In some embodiments, the compositions and methods of the present invention provide treatment, symptom reduction and/or prevention of one or more diseases, indications, conditions, and disorders including, but not limited to: acute myeloid leukemia, drug-resistant leukemias, breast cancer, lymphomas, uterine cancers, lung cancer, ovarian cancer, malaria, veterinary applications, vancomycin-resistant enterococcus (VRE), Parkinsons (e.g. as a neuroprotective agent), fibromyalgia, infected animal bite wounds (e.g. *pasteurella multocida, pasteurella pneumotropica*, etc.), rheumatoid arthritis, reactive arthritis, chronic inflammatory lung diseases (e.g. panbronchiolitis, asthma, cystic fibrosis, bronchitis, etc.), sarcoidosis, prevention of aortic aneurysm in patients with Marfan Syndrome, multiple sclerosis, meibomian gland dysfunction, acne, amoebic dysentery, anthrax, cholera, gonorrhea (e.g. when penicillin cannot be given), Gougerot-Carteaud Syndrome, lyme disease, bubonic plague, periodontal disease, respiratory infections (e.g. pneumonia), HIV (e.g. as an adjuvant to HAART), Rocky Mountain spotted fever, syphilis (e.g. when penicillin cannot be given), urinary tract infections, rectal infections, infections of the cervix, upper respiratory tract infections (e.g. caused by *Streptococcus pyogenes, Streptococcus pneumoniae* and *Hemophilus influenza*), lower respiratory tract infections (e.g. caused by *Streptococcus pyogenes, Streptococcus pneumoniae, Mycoplasma pneumonia*, skin and soft tissue infections (e.g. caused by *Streptococcus pyogenes, Staphylococcus aureaus*), infections caused by *rickettsia* (e.g. Rocky Mountain spotted fever, typhus group infections, Q fever, rickettsialpox), Psittacosis of ornithosis (e.g. caused by *Chlamydia psittaci*), infections caused by *Chlamydia trachomatis* (e.g. uncomplicated urethral, endocervical, or rectal infections; inclusion conjunctivitis; trachoma; lymphogranuloma venereum, etc.), granuloma inquinale (e.g. caused by *Calymmatobacterium granulomatis*), relapsing fever (e.g. caused by *Borrelia* sp.), bartonellosis (e.g. caused by *Bartonella bacilli-formis*), chancroid (e.g. caused by *Hemophilus ducreyi*), tularemia (e.g. caused by *Francisella tularensis*), plaque (e.g. caused by *Yersinia pestis*), cholera (e.g. caused by *Vibrio cholera*), *Campylobacter* fetus infections, intestinal amebiasis (e.g. caused by *Entamoeba histolytica*), urinary tract infections (e.g. caused by susceptible strains of *Escherichia coli, Klebsiella*, etc.), infections caused by susceptible gram-negative organisms (e.g. *E. coli, Enterobacter aerogenes, Shigella* sp., *Acinetobacter* sp., *Klebsiella* sp., and *Bacteroides* sp.), severe acne, etc. In some embodiments, compositions and methods of the present invention are also relevant towards nonbiological processes that require the water solubilization of insoluble agents, especially when they can be rapidly coupled to an inert substance such as nanodiamonds that are very stable, and can be easily removed, if necessary, via simple centrifugation processes. For biological applications, it has been shown that nanodiamonds can be removed in vivo via the urinary system, confirming their bio-amenability.

II. Nanodiamond-Nucleic Acid Complexes

The present invention provides nanodiamond-nucleic acid complexes that are capable of nucleic acid release with preserved function. In certain embodiments, such complexes serve as non-viral gene delivery vectors. Such ND-nucleic acid complexes may be employed, for example, in a broad array of medical disorders including cancer, inflammation, autoimmune diseases, wound healing, pain, neurological disorders, and other types of disorders. By functionalizing the ND surface with low molecular weight polyethyleneimine (e.g., PEI800), it was shown that DNA plasmids were capable of being released upon cellular introduction whereas without the functionalization step, the DNA could be bound (via physisorption) to the NDs, but not released. ND-nucleic acid complexes may be used, for example, in the treatment for cancer, inflammation, pain, scarring/wound healing, infection, and diabetes insulin delivery, and other disorders capable of treatment with gene therapy type approaches.

III. Alkaline-Sensitive Nanodiamond-Protein Complexes

The present invention provides nanodiamond-protein complexes that allow, for example, desorption of the protein in alkaline environments. Work conducted during the development of embodiments of the present invention exemplified this invention with the development of a Nanodiamond (ND)-Insulin complex that is capable of pH-dependent protein release (e.g., for applications in diabetes treatment as well as wound healing). This is important as it has been shown that following skin burns, insulin is immediately administered to prevent infection, a major complication. Furthermore, it has been shown that skin pH levels following burns can reach basic levels (e.g. 10-11). Work conducted during the development of embodiments of the present invention has shown that such complexes can selectively release insulin at that pH level while unreleased insulin function is sequestered until it is delivered. In certain embodiments, such as those where the protein is insulin, the ND-protein complexes are use for the treatment of wound healing, infection, and diabetes insulin delivery, among others.

There remains a significant need for enhanced methods of drug delivery to maximize therapeutic effects while decreasing associated complications. Systemic treatments pose various problems concerning the pervasiveness of drug exposure to the body and can lead to harmful side effects outweighing treatment benefits. Effectively targeting and controlling drug delivery as to limit drug-tissue interaction is a desired outcome. In this regard, site-specific drug delivery is highly advantageous for a host of ailments ranging from cancer to cardiovascular treatments. Recent advances in nanomedicine (e.g., imaging and diagnosis [1-3], drug delivery [4-10] and gene therapy [11-13]) have demonstrated the benefits of nanoparticle therapeutics, including reduction of drug concentration, targeted delivery, diminished complications and biocompatibility [3, 14-16].

Numerous studies have shown the efficacy of transiently linking or conjugating drugs and therapeutic molecules to NDs, including chemotherapy agents, organic molecules and proteins [29, 33, 34]. There has been recent work concerning the drug release profiles of NDs [8, 9], yet there is little scientific inquiry relating to the release of protein-based drugs. Examples of protein-based drugs include cytokines, monoclonal antibodies, hormones and clotting factors, all of which hold great promise or have been substantiated for targeted drug delivery.

Enhanced specificity in drug delivery aims to improve upon systemic elution methods by locally concentrating therapeutic agents and reducing negative side effects. As described in Example 2 below, bovine insulin was non-covalently bound to detonated nanodiamonds via physical adsorption in an aqueous solution and demonstrated pH-dependent desorption in alkaline environments of sodium hydroxide. Insulin adsorption to NDs was confirmed by FT-IR spectroscopy and zeta potential measurements, while both adsorption and desorption were visualized with TEM imaging, quantified using protein detection assays and protein function demonstrated by MTT and RT-PCR. NDs combined with insulin at a 4:1 ratio showed 79.8±4.3% adsorption and 31.3±1.6% desorption in pH-neutral and alkaline solutions, respectively. Additionally, a 5-day desorption assay in NaOH (pH 10.5) and neutral solution resulted in 45.8±3.8% and 2.2±1.2% desorption, respectively. MTT viability assays and quantitative RT-PCR (expression of Ins1 and Csf3/G-csf genes) reveal bound insulin remains inactive until alkaline-mediated desorption. Thus, the present invention provides for applications in sustained drug release, wound therapy and imaging employing a therapeutic protein-ND complex with demonstrated tunable release and preserved activity.

IV. Carrier/Delivery Element

In some embodiments, the present invention provides a carrier/delivery element. In some embodiments, a carrier/delivery element provides a barrier, surface, or material to contain, encapsulate, sequester, or confine a therapeutic element. In some embodiments, a carrier/delivery element is configured to allow the controlled release of a therapeutic element. In some embodiments, a carrier/delivery element comprises a layer above and/or adjacent to a therapeutic layer. In some embodiments, a carrier/delivery element comprises a bilayer above and below to a therapeutic layer. In some embodiments, a carrier/delivery element comprises a bilayer which surrounds a therapeutic layer. In some embodiments, a therapeutic layer resides between the individual layers of a bilayer of a carrier/delivery element. In some embodiments, a bilayer comprises a base layer and an elution or semi-permeable layer. In some embodiments, a carrier/delivery element comprises a matrix or material within which a therapeutic element is contained. In some embodiments, a carrier/delivery element is porous, permeable, and/or semi-permeable. In some embodiments, a carrier/delivery element is configured to provide controlled release of a therapeutic element from the carrier/delivery element. In some embodiments, a carrier/delivery element comprises one or more matrix elements and one or more bilayer elements. In some embodiments, a matrix element resides between the individual layers of a bilayer. In some embodiments, a matrix element embedded with a therapeutic element resides between a base layer and elution layer of a bilayer element.

In some embodiments, a carrier/delivery element comprises a film, thin-layer film, or nanofilm. In some embodiments, a carrier/delivery element or elements may be of any desired thickness (e.g. 0.1 nm . . . 0.2 nm . . . 0.5 nm . . . 1.0 nm . . . 2.0 nm . . . 5.0 nm . . . 10 nm . . . 20 nm . . . 50 nm . . . 100 nm . . . 200 nm . . . 500 nm . . . 1 mm . . . 2 mm 5 mm 1 cm, and thicknesses therein, etc.). In some embodiments, a carrier/delivery element can be configured in any shape, dimensions, etc.

Bilayer Carrier/Delivery Element

In some embodiments, the present invention provides a bilayer carrier/delivery element. In some embodiments, a carrier/delivery element comprises a base layer and a top layer (e.g. elution layer, semi-permeable layer, release layer, degradable layer, etc.). In some embodiments, the present invention provides a therapeutic layer. In some embodiments, a therapeutic layer resides between a base layer and a top layer. In some embodiments, one or both of a base layer and a top layer are porous, permeable, and/or semi-permeable (e.g. permeable to one or more therapeutics of a therapeutic layer). In some embodiments, one or both of a base layer and a top layer are impermeable (e.g. impermeable to one or more therapeutics of a therapeutic layer). In some embodiments, the present invention provides an impermeable base layer and a permeable or semi-permeable elution layer. In some embodiments, a therapeutic element (e.g. therapeutic layer) resides between an impermeable base layer and a top elution layer (e.g. permeable layer or semi-permeable layer). In some embodiments, a top elution layer is configured to allow the controlled elution of a therapeutic. In some embodiments, a top elution layer is configured to allow the controlled elution of a therapeutic from the therapeutic layer through the elution layer. In some embodiments, a base layer is configured to allow elution. In some embodiments, a base layer is configured to resist elution.

In some embodiments, one or more layers (e.g. top layer, base layer, elution layer, etc.) of the present invention comprise one or more polymers including, but not limited to polyacrylates, polyamides, polyesters, polycarbonates, polyimides, polystyrenes, acrylonitrile butadiene styrene (ABS), polyacrylonitrile (PAN) or Acrylic, polybutadiene, poly(butylene terephthalate) (PBT), poly(ether sulfone) (PES, PES/PEES), poly(ether ether ketone)s (PEEK, PES/PEEK), polyethylene (PE), poly(ethylene glycol) (PEG), poly(ethylene terephthalate) (PET), polypropylene (PP), polytetrafluoroethylene (PTFE), styrene-acrylonitrile resin (SAN), poly(trimethylene terephthalate) (PTT), polyurethane (PU), polyvinyl butyral (PVB), polyvinylchloride (PVC), polyvinylidenedifluoride (PVDF), poly(vinyl pyrrolidone) (PVP), poly-p-xylenes, derivatives thereof, substituents thereof, combinations thereof, similar polymers, etc.

In some embodiments, one or more layers (e.g. top layer, base layer, elution layer, etc.) of the present invention comprise a nanofilm. In some embodiments, the thickness of a nanofilm is less than about 100 nanometers (e.g. <100 nm, <50 nm, <20 nm, <10 nm, <5.0 nm, <2.0 nm, <1.0 nm, <0.5 nm, <0.2 nm, <0.1 nm, etc.). In some embodiments, the thickness of a nanofilm is greater than about 0.1 nanometers (e.g. >0.1 nm, >0.2 nm, >0.5 nm, >1.0 nm, >2.0 nm, >5.0 nm, >10 nm, >20 nm, >50 nm, etc.). In some embodiments, a nanofilm may be permeable, semi-permeable, or impermeable. In some embodiments, a nanofilm has a filtration function, allowing certain species to pass through the nanofilm. In some embodiments, a nanofilm has a controlled filtration function, allowing species to pass through the nanofilm at a defined rate (e.g. based on pore size, pore frequency, etc.). In some embodiments, a nanofilm is permeable only to particular species in particular fluid and/or species smaller than the particular species. In some embodiments, a nanofilm has a molecular weight cut-off. In some embodiments, a nanofilm has a high permeability for certain species in a certain solvent. In some embodiments, a nanofilm has a low permeability for certain species in a certain solvent. In some embodiments, a nanofilm has a high permeability for certain species and low permeability for other species in a certain solvent. In some embodiments, a nanofilm composition, material, and/or device is a made up of two or more layers of nanofilm. In some embodiments, a spacing layer may be used between any two nanofilm layers. In some embodiments, spacing layers may include a polymer layer, gel layer, hydrogel layer, therapeutic layer, void layer, etc. In some embodiments, a nanofilm, or other material of the present invention, is deposited on a substrate (e.g. surface, material, composition, device, etc.), which may be porous or non-porous. In some embodiments, a nanofilm, or other material of the present invention, has surface attachment groups, and may be covalently bonded to a substrate through surface attachment groups, or bonded to a substrate through ionic interactions. In some embodiments, surface attachment groups provide contact or links between multiple layers of nanofilm, or between nanofilm layers and other layers (e.g. polymer layer, gel layer, hydrogel layer, therapeutic layer, etc.).

In some embodiments, a layer or layers of the present invention provide nanopores which allow controlled elution of a therapeutic. In some embodiments, nanopores of the present invention are greater than 0.1 nm in diameter (e.g. >0.1 nm, >0.2 nm, >0.5 nm, >1.0 nm, >2.0 nm, >5.0 nm, >10 nm, >20 nm, >50 nm, >100 nm, >200 nm, >500 nm, >1 mm, etc.). In some embodiments, nanopores of the present invention are less than 2 mm in diameter (e.g. <2 mm, <1 mm, <500 nm, <200 nm, <100 nm, <50 nm, <20 nm, <10 nm, <5.0 nm, <2.0 nm, <1.0 nm, <0.5 nm, <0.2 nm, <0.1 nm, etc.). In some embodiments, nanopores of the present invention have diameters between 0.1 nm and 1 mm (e.g. 0.1 nm, 0.2 nm, 0.3 nm, 0.4 nm, 0.5 nm, 0.6 nm, 0.7 nm, 0.8 nm, 0.9 nm, 1.0 nm, 1.1 nm, 1.2 nm, 1.3 nm, 1.4 nm, 1.5 nm, 1.6 nm, 1.7 nm, 1.8 nm, 1.9 nm, 2.0 nm, 3.0 nm, 4.0 nm, 5.0 nm, 6.0 nm, 7.0 nm, 8.0 nm, 9.0 nm, 10 nm, 20 nm, 30 nm, 40 nm, 50, nm, 100, nm, 200, nm, 500, nm, 1 mm, and diameters therein). In some embodiments, an elution layer, top layer, base layer, permeable layer, porous layer, and/or semi-permeable layer of the present invention comprises nanopores.

In some embodiments, a carrier/delivery element is a nanofilm composition comprising a base layer, therapeutic layer, and an elution layer, wherein the therapeutic layer resides between the base layer and the elution layer. In some embodiments, the base layer is permeable, semi-permeable, or impermeable. In some embodiments, the base layer is comprised of any materials disclosed herein or any other suitable materials. In some embodiments, the base layer is configured for interaction with a substrate (e.g. surface, material, composition, device, etc.). In some embodiments, a base layer provides functional groups or other characteristics (e.g. adhesive) known to those in the art for interaction with a substrate. In some embodiments, the base layer provides stable interaction with a substrate. In some embodiments, the base layer interacts with a substrate to modify the surface of the substrate. In some embodiments, the present invention provides a permeable or semi-permeable elution layer. In some embodiments, the elution layer is comprised of any materials disclosed herein or any other suitable materials. In some embodiments, the elution layer is permeable or semi-permeable to one or more molecules, macromolecules (e.g. peptides, lipids, nucleic acids, etc.), compositions, therapeutics, drugs, small molecules, etc. contained within an underlying layer (e.g. therapeutic layer). In some embodiments, the elution layer provides release (e.g. controlled release) of one or more contents of the underlying layer (e.g. therapeutic layer). In some embodiments, the elution layer provides release (e.g. controlled release) of one or more contents of the underlying layer (e.g. therapeutic layer) through pores in the elution layer. In some embodiments, degradation of the elution layer by environmental factors (e.g. dissolving into solvent, hydrolysis, etc.) provides release (e.g. controlled release of one or more contents of the underlying layer (e.g. therapeutic layer). In some embodiments, the base layer provides positioning of the nanofilm composition on a substrate (e.g. device, surface, composition, etc.), the substrate is then positioned in a desired environment (e.g. on a subject, within a subjects body, etc.), and the elution layer provides release (e.g. controlled release) of one or more compositions from within the intervening layer (e.g. layer between the base layer and elution layer (e.g. therapeutic layer)).

Matrix Carrier/Delivery Element

In some embodiments, a carrier/delivery element is a matrix (e.g. a substantially crosslinked system). In some embodiments, a matrix is a three-dimensional crosslinked network. In some embodiments, an internal network structure within the matrix results from physical bonds, chemical bonds, crystallites, and/or other junctions. In some embodiments, a matrix is a substantially dilute crosslinked system. In some embodiments, a matrix comprises fluid within a three-dimensional crosslinked network. In some embodiments, a matrix comprises greater than 50% (e.g. >50%, >60%, >70%, >80%, >90%, >95%, >99%) fluid (e.g. water). In some embodiments, a matrix exhibits solid and/or liquid characteristics. In some embodiments, a matrix comprises a three-dimensional crosslinked network within a liquid (e.g. water). In some embodiments, a solid three-dimensional network spans the volume of a liquid medium. In some embodiments, a matrix comprises a hydrogel (aka aquagel). In some embodiments, a hydrogel comprises a network of polymer chains that are water-insoluble (e.g. colloidal gel) in which water is the dispersion medium. In some embodiments, a hydrogel comprises a network of water soluble polymer chains. In some embodiments, hydrogels may vary in strength, permeability, flexibility, hydration, pH, hardness, stickiness, etc. Methods and compositions for hydrogel preparation and use are well known in the art (U.S. Pat. No. 7,511,083 to Madsen, U.S. Pat. No. 7,413,752 to Sawhney, U.S. Pat. No. 7,407,912 Mertens, U.S. Pat. No. 7,329,414 to Fisher, U.S. Pat. No. 7,312,301 to Fang, U.S. Pat. No. 3,640,741 to Etes, U.S. Pat. No. 3,865,108 to Hartop, U.S. Pat. No. 3,992,562 to Denzinger et al., U.S. Pat. No. 4,002,173 to Manning et al., U.S. Pat. No. 4,014,335 to Arnold, U.S. Pat. No. 4,207,893 to Michaels, and in Handbook of Common Polymers, (Scott and Roff, Eds.) Chemical Rubber Company, Cleveland, Ohio.

In some embodiments, an additive element (e.g. therapeutic element) is embedded, contained, absorbed, and/or located within the matrix element (e.g. hydrogel). In some embodiments, a therapeutic element resides within a hydrogel element. In some embodiments, a therapeutic element is dissolved in a solvent (e.g. water) which provides the fluid portion of a matrix composition (e.g. hydrogel). In some embodiments, a matrix (e.g. hydrogel) provides a reservoir for loading a therapeutic element (e.g. drug, small molecule, macromolecule, etc.). In some embodiments, matrix characteristics (e.g. pore size, hydration level, matrix density, matrix composition, etc.) are tailored to provide a suitable/preferable carrier environment for a particular therapeutic element. In some embodiments, matrix characteristics (e.g. pore size, hydration level, matrix density, matrix composition, etc.) are tailored to provide a suitable/preferable delivery environment for a particular therapeutic element. In some embodiments, a matrix (e.g. hydrogel) provides release (e.g. controlled release) of a therapeutic element into the surrounding environment (e.g. biological system). In some embodiments, a therapeutic element elutes by diffusion from a matrix into the surrounding environment. In some embodiments, degradation of a matrix results in elution of a therapeutic element from within the matrix into the surrounding environment.

V. Therapeutic Element

Therapeutics

In some embodiments, the present invention provides a therapeutic element for the treatment and/or prevention of a disease, disorder, discomfort, ailment, etc. In some embodiments, the present invention provides compositions, devices, materials, methods, etc. for the release (e.g. controlled release) of a therapeutic element (e.g. into the surrounding environment). In some embodiments, a therapeutic element is embedded, encapsulated, contained, or layered in a carrier/delivery element. In some embodiments, a therapeutic element elutes from a carrier/delivery element. In some embodiments, a therapeutic element elutes from a carrier/delivery element at a desired or designed time scale (e.g. approximately 1 second, approximately 5 seconds, approximately 10 seconds, approximately 30 seconds, approximately 1 minute, approximately 5 minutes, approximately 10 minutes, approximately 30 minutes, approximately 1 hour, approximately 2 hours, approximately 4 hours, approximately 12 hours, approximately 24 hours, approximately 2 days, approximately 4 days, approximately 1 week, approximately 1 month, approximately 1 year, greater than 1 year, etc.). In some embodiments, a therapeutic element elutes from a carrier/delivery element with a desired or designed half life (e.g. approximately 1 second, approximately 5 seconds, approximately 10 seconds, approximately 30 seconds, approximately 1 minute, approximately 5 minutes, approximately 10 minutes, approximately 30 minutes, approximately 1 hour, approximately 2 hours, approximately 4 hours, approximately 12 hours, approximately 24 hours, approximately 2 days, approximately 4 days, approximately 1 week, approximately 1 month, approximately 1 year, greater than 1 year, etc.). In some embodiments, a therapeutic element elutes through pores and/or pinholes in a carrier/delivery element. In some embodiments, a therapeutic element elutes upon degradation and/or dissolving of a carrier/delivery element in or on the surrounding environment (e.g. body fluid, body surface, etc.).

In some embodiments, the present invention provides a therapeutic element comprising one or more therapeutics from the list including, but not limited to thrombin inhibitors, antithrombogenic agents, thrombolytic agents, fibrinolytic agents, vasospasm inhibitors, calcium channel blockers, vasodilators, antihypertensive agents, antimicrobial agents, antibiotics, inhibitors of surface glycoprotein receptors, antiplatelet agents, antimitotics, microtubule inhibitors, anti secretory agents, actin inhibitors, remodeling inhibitors, antisense nucleotides, anti metabolites, antiproliferatives, anticancer chemotherapeutic agents, anti-inflammatory steroid or non-steroidal anti-inflammatory agents, immunosuppressive agents, growth hormone antagonists, growth factors, dopamine agonists, radiotherapeutic agents, extracellular matrix components, inhibitors, free radical scavengers, chelators, antioxidants, anti polymerases, antiviral agents, photodynamic therapy agents, gene therapy agents, etc.

In some embodiments, a therapeutic element comprises one or more drugs from one or more of the following classes: 5-alpha-reductase inhibitors, 5-aminosalicylates, 5HT3 receptor antagonists, adamantane antivirals, adrenal cortical teroids, adrenergic bronchodilators, agents for hypertensive emergencies, agents for pulmonary hypertension, aldosterone receptor antagonists, alkylating agents, alpha-glucosidase inhibitors, alternative medicines, amebicides, aminoglycosides, aminopenicillins, aminosalicylates, amylin analogs, analgesic combinations, analgesics, androgens and anabolic steroids, angiotensin converting enzyme inhibitors, angiotensin II inhibitors, anorectal preparations, anorexiants, antacids, anthelmintics, anti-angiogenic ophthalmic agents, anti-infectives, antiadrenergic agents, centrally acting, antiadrenergic agents, peripherally acting, antianginal agents, antiarrhythmic agents, antiasthmatic combinations, antibiotics/antineoplastics, anticholinergic antiemetics, anticholinergic antiparkinson agents, anticholinergic bronchodilators, anticholinergics/antispasmodics, anticoagulants, anticonvulsants, antidepressants, antidiabetic agents, antidiabetic combinations, antidiarrheals, antidotes, antiemetic/antivertigo agents, antifungals, antigout agents, antihistamines, antihyperlipidemic agents, antihyperlipidemic combinations, antihypertensive combinations, antihyperuricemic agents, antimalarial agents, antimalarial combinations, antimalarial quinolines, antimetabolites, antimigraine agents, antineoplastic detoxifying agents, antineoplastic interferons, antineoplastic onoclonal antibodies, antineoplastics, antiparkinson agents, antiplatelet agents, antipseudomonal penicillins, antipsoriatics, antipsychotics, antirheumatics, antiseptic and germicides, antitoxins and antivenins, antituberculosis agents, antituberculosis combinations, antitussives, antiviral agents, antiviral combinations, antiviral interferons, anxiolytics, sedatives, and hypnotics, atypical antipsychotics, azole antifungals, bacterial vaccines, barbiturate anticonvulsants, barbiturates, benzodiazepine anticonvulsants, benzodiazepines, beta-adrenergic blocking agents, beta-lactamase inhibitors, bile acid sequestrants, biologicals, bisphosphonates, bronchodilator combinations, bronchodilators, calcium channel blocking agents, carbamate anticonvulsants, carbapenems, carbonic anhydrase inhibitor anticonvulsants, carbonic anhydrase inhibitors, cardiac stressing agents, cardioselective beta blockers, cardiovascular agents, central nervous system agents, cephalosporins, cerumenolytics, chelating agents, chemokine receptor antagonist, chloride channel activators, cholesterol absorption inhibitors, cholinergic agonists, cholinergic muscle stimulants, cholinesterase inhibitors, CNS stimulants, coagulation modifiers, colony stimulating factors, contraceptives, corticotropin, coumarins and indandiones, cox-2 inhibitors, decongestants, dermatological agents, diagnostic radiopharmaceuticals, dibenzazepine anticonvulsants, digestive enzymes, dipeptidyl peptidase 4 inhibitors, diuretics, dopaminergic antiparkinsonism agents, drugs used in alcohol dependence, echinocandins, estrogens, expectorants, factor Xa inhibitors, fatty acid derivative anticonvulsants, fibric acid derivatives, first generation cephalosporins, fourth generation cephalosporins, functional bowel disorder agents, gallstone solubilizing agents, gamma-aminobutyric acid analogs, gamma-aminobutyric acid reuptake inhibitors, gastrointestinal agents, general anesthetics, genitourinary tract agents, GI stimulants, glucocorticoids, glucose elevating agents, glycoprotein platelet inhibitors, glycylcyclines, gonadotropin releasing hormones, gonadotropins, group I antiarrhythmics, group II antiarrhythmics, group III antiarrhythmics, group IV antiarrhythmics, group V antiarrhythmics, growth hormone receptor blockers, growth hormones, *H. pylori* eradication agents, H2 antagonists, hematopoietic stem cell mobilizer, heparin antagonists, heparins, herbal products, hormone replacement therapy, hormones, hormones/antineoplastics, hydantoin anticonvulsants, illicit (street) drugs, immune globulins, immunologic agents, immunosuppressive agents, impotence agents, in vivo diagnostic biologicals, incretin mimetics, inhaled corticosteroids, inotropic agents, insulin, insulin-like growth factor, integrase strand transfer inhibitor, interferons, intravenous nutritional products, iodinated contrast media, ionic iodinated contrast media, iron products, ketolides, laxatives, leprostatics, leukotriene modifiers, lincomycin derivatives, local injectable anesthetics, loop diuretics, lung surfactants, lymphatic staining agents, lysosomal enzymes, macrolide derivatives, macrolides, magnetic resonance imaging contrast media, MAO Inhibitors, mast cell stabilizers, medical gas, meglitinides, metabolic agents, methylxanthines, mineralocorticoids, minerals and electrolytes, miscellaneous agents, miscellaneous analgesics, miscellaneous antibiotics, miscellaneous anticonvulsants, miscellaneous antidepressants, miscellaneous antidiabetic agents, miscellaneous antiemetics, miscellaneous antifungals, miscellaneous antihyperlipidemic agents, miscellaneous antimalarials, miscellaneous antineoplastics, miscellaneous antiparkinson agents, miscellaneous antipsychotic agents, miscellaneous antituberculosis agents, miscellaneous antivirals, miscellaneous anxiolytics, sedatives and hypnotics, miscellaneous biologicals, miscellaneous cardiovascular agents, miscellaneous central nervous system agents, miscellaneous coagulation modifiers, miscellaneous diuretics, miscellaneous genitourinary tract agents, miscellaneous GI agents, miscellaneous hormones, miscellaneous metabolic agents, miscellaneous ophthalmic agents, miscellaneous otic agents, miscellaneous respiratory agents, miscellaneous sex hormones, miscellaneous topical agents, miscellaneous uncategorized agents, miscellaneous vaginal agents, mitotic inhibitors, monoclonal antibodies, mouth and throat products, mTOR kinase inhibitors, mucolytics, muscle relaxants, mydriatics, narcotic analgesic combinations, narcotic analgesics, nasal anti-infectives, nasal antihistamines and decongestants, nasal lubricants and irrigations, nasal preparations, nasal steroids, natural penicillins, neuraminidase inhibitors, neuromuscular blocking agents, next generation cephalosporins, nicotinic acid derivatives, NNRTIs, non-cardioselective beta blockers, non-iodinated contrast media, non-ionic iodinated contrast media, non-sulfonylureas, nonsteroidal anti-inflammatory agents, nucleoside reverse transcriptase inhibitors (NRTIs), nutraceutical products, nutritional products, ophthalmic anesthetics, ophthalmic anti-infectives, ophthalmic anti-inflammatory agents, ophthalmic antihistamines and decongestants, ophthalmic diagnostic agents, ophthalmic glaucoma agents, ophthalmic lubricants and irrigations, ophthalmic preparations, ophthalmic steroids, ophthalmic steroids with anti-infectives, ophthalmic surgical agents, oral nutritional supplements, otic anesthetics, otic anti-infectives, otic preparations, otic steroids, otic steroids with anti-infectives, oxazolidinedione anticonvulsants, penicillinase resistant penicillins, penicillins, peripheral opioid receptor antagonists, peripheral vasodilators, peripherally acting antiobesity agents, phenothiazine antiemetics, phenothiazine antipsychotics, phenylpiperazine antidepressants, plasma expanders, platelet aggregation inhibitors, platelet-stimulating agents, polyenes, potassium-sparing diuretics, probiotics, progestins, prolactin inhibitors, protease inhibitors, proton pump inhibitors, psoralens, psychotherapeutic agents, psychotherapeutic combinations, purine nucleosides, pyrrolidine anticonvulsants, quinolones, radiocontrast agents, radiologic adjuncts, radiologic agents, radiologic conjugating agents, radiopharmaceuticals, recombinant human erythropoietins, renin inhibitors, respiratory agents, respiratory inhalant products, rifamycin derivatives, salicylates, sclerosing agents, second generation cephalosporins, serotoninergic neuroenteric modulators, sex hormone combinations, sex hormones, skeletal muscle relaxant combinations, skeletal muscle relaxants, smoking cessation agents, spermicides, SSNRI antidepressants, SSRI antidepressants, Statins, sterile irrigating solutions, *streptomyces* derivatives, succinimide anticonvulsants, sulfonamides, sulfonylureas, tetracyclic antidepressants, tetracyclines, therapeutic radiopharmaceuticals, thiazide diuretics, thiazolidinediones, thioxanthenes, third generation cephalosporins, thrombin inhibitors, thrombolytics, thyroid drugs, topical acne agents, topical agents, topical anesthetics, topical anti-infectives, topical antibiotics, topical antifungals, topical antihistamines, topical antipsoriatics, topical antivirals, topical astringents, topical debriding agents, topical depigmenting agents, topical emollients, topical steroids, topical steroids with anti-infectives, toxoids, triazine anticonvulsants, tricyclic antidepressants, tumor necrosis factor (TNF) inhibitors, kinase inhibitors, ultrasound contrast media, upper respiratory combinations, urea anticonvulsants, urinary anti-infectives, urinary antispasmodics, urinary pH modifiers, vaginal anti-infectives, preparations, vasodilators, vasopressin antagonists, vasopressors, viral vaccines, viscosupplementation agents, vitamin and mineral combinations, vitamins, etc.

In some embodiments, a therapeutic element comprises a pharmaceutically acceptable carrier. In some embodiments, a therapeutic element is administered via any desired oral, parenateral, topical, intervenous, transmucosal, and/or inhalation routes. In some embodiments, a therapeutic element comprises a composition which is formulated with a pharmaceutically acceptable carrier and optional excipients, flavors, adjuvants, etc. in accordance with good pharmaceutical practice. In some embodiments, the present invention may be in the form of a solid, semi-solid or liquid dosage form: such as patch, tablet, capsule, pill, powder, suppository, solution, elixir, syrup, suspension, cream, lozenge, paste, spray, etc. As those skilled in the art would recognize, depending on the chosen route of administration, the composition form is determined. In general, it is preferred to use a unit dosage form of the therapeutic element in order to achieve an easy and accurate administration of the active compound. In general, the therapeutically effective pharmaceutical compound is present in such a dosage form at a concentration level ranging from about 0.5% to about 99% by weight of the total therapeutic element: i.e., in an amount sufficient to provide the desired unit dose. In some embodiments, the therapeutic element may be administered in single or multiple doses. The particular route of administration and the dosage regimen will be determined by one of skill in keeping with the condition of the individual to be treated and said individual's response to the treatment. The present invention also provides a therapeutic element in a unit dosage form for administration to a subject, comprising a pharmaceutical compound and one or more nontoxic pharmaceutically acceptable carriers, adjuvants or vehicles. The amount of the active ingredient that may be combined with such materials to produce a single dosage form will vary depending upon various factors, as indicated above. A variety of materials can be used as carriers, adjuvants and vehicles in the composition of the invention, as available in the pharmaceutical art. Injectable preparations, such as oleaginous solutions, suspensions or emulsions, may be formulated as known in the art, using suitable dispersing or wetting agents and suspending agents, as needed. The sterile injectable preparation may employ a nontoxic parenterally acceptable diluent or solvent such as sterile nonpyrogenic water or 1,3-butanediol. Among the other acceptable vehicles and solvents that may be employed are 5% dextrose injection, Ringer's injection and isotonic sodium chloride injection (as described in the USP/NF). In addition, sterile, fixed oils may be conventionally employed as solvents or suspending media. For this purpose, any bland fixed oil may be used, including synthetic mono-, di- or triglycerides. Fatty acids such as oleic acid can also be used in the preparation of injectable compositions. Suppositories for rectal administration of the pharmaceutical compound can be prepared by mixing the therapeutic with a suitable nonirritating excipient such as cocoa butter and polyethylene glycols, which are solid at ordinary temperatures but liquid at body temperature and which therefore melt in the rectum and release the drug. Additionally, it is also possible to administer the aforesaid pharmaceutical compounds topically and this may be preferably done by way of patch, cream, salve, jelly, paste, ointment and the like, in accordance with the standard pharmaceutical practice.

Nanodiamond Functionalization

In some embodiments, a therapeutic element of the present invention comprises one or more nanodiamonds, nanodiamond clusters, nanodiamond film, functionalized nanodiamonds, functionalized-nanodiamond film, and/or functionalized-nanodiamond clusters. In some embodiments, any suitable therapeutic compound (e.g. drug, small molecule, macromolecule, etc.) including, but not limited to those listed herein, is provided in conjunction with one or more nanodiamond complexes in the therapeutic element of the present invention.

Nanodiamonds with diameters of approximately 2-8 nm are assembled into closely packed ND complexes (e.g. multilayer ND nanofilm, ND nanoclusters, etc.). In some embodiments, ND nanofilms are of any suitable thickness (e.g. 2 nm . . . 5 nm . . . 10 nm . . . 20 nm . . . 50 nm . . . 100 nm . . . 200 nm, etc.). In some embodiments, nanoclusters are of any suitable diameter (e.g. (e.g. 5 nm . . . 10 nm . . . 20 nm . . . 50 nm . . . 100 nm . . . 200 nm, etc.). In some embodiments, ND nanofilms and/or ND nanoclusters comprise multiple nanodiamonds. In some embodiments, ND nanofilms and/or ND nanoclusters of the present invention comprise integrated therapeutic compounds and/or complexes. In some embodiments, therapeutic compounds and/or complexes are embedded within ND nanofilms and/or ND nanoclusters. In some embodiments, the structures of ND nanofilms and/or ND nanoclusters prepared by methods of the present invention are adjusted according to the desired application (e.g. size, thickness, diameter, ND:therapeutic ratio, type of therapeutic, etc.). In some embodiments, functionalized ND nanocomplexes (e.g. nanofilms, nanoclusters, etc.) comprise ND nanocomplexes integrated with therapeutic molecules. In some embodiments, functionalized ND nanocomplexes are configured to provide controlled release of therapeutic molecules into or onto the surrounding environment (e.g. body fluid, body surface, etc.). In some embodiments, a therapeutic element comprises one or more ND nanocomplexes combined with additional elements, compositions, materials, compounds, complexes, carriers, additives, etc.

VI. Applications

In some embodiments, one or more carrier/delivery elements and one or more therapeutic elements of the present invention are combined to provide a material, composition, and/or device of the present invention. Any combination of embodiments of the carrier/delivery elements and therapeutic elements described explicitly or inherently herein are contemplated. In some embodiments, the present invention provides a coating for devices, surfaces, substrates, compositions, materials, etc. In some embodiments, devices, surfaces, substrates, compositions, or materials coated according to the present invention are configured to administer one or more therapeutic compositions. In some embodiments the present invention is applied to medical devices such as a balloon catheter, an atherectomy catheter, a drug delivery catheter, a stent delivery catheter, an endoscope, an introducer sheath, a fluid delivery device, other infusion or aspiration devices, device delivery (i.e. implantation) devices, and the like.

In some embodiments, the present invention provides a medical device with one or more of its surfaces coated with a composition, material, or nanofilm described herein. The medical device may be implantable. In some embodiments the medical device contains an electrode. A coating of the present invention may be used on a variety of medical substrates, including an implantable medical device. Such medical devices may be made of a variety of biocompatible materials including, but not limited to, any suitable metal or non-metal material (e.g. metals (e.g. Lithium, Magnesium, Aluminium, Titanium, Vanadium, Chromium, Manganese, Cobalt, Nickel, Copper, Zinc, Zirconium, Molybdenium, Silver, Cadmium, Antimony, Barium, Osmium, Platinum, Mercury, Thallium, Lead, etc.), plastics (e.g. Bakelite, neoprene, nylon, PVC, polystyrene, polyacrylonitrile, PVB, silicone, rubber, polyamide, synthetic rubber, vulcanized rubber, acrylic, polyethylene, polypropylene, polyethylene terephthalate, polytetrafluoroethylene, gore-tex, polycarbonate, etc.), etc. Medical substrates onto which the composition and/or materials of the present invention are coated include, neural/cardiovascular/retinal implants, leads and stents, and dental implants (e.g., nanofilms to seed bone growth). In some embodiments, the materials, compositions and/or nanofilm may be coated onto the electrode of an implantable medical device. In fact, coating the present materials, compositions and/or nanofilms onto an electrode is contemplated to provide important medical advantage because the materials, compositions and/or nanofilm is contemplated to prevent or minimize bio-fouling which often begins at the site of a metal electrode. In addition, unlike more conventional implant coatings, the present coatings may be made thin enough that they do not interfere with electrode function (e.g., electrical conductivity or redox reactions at electrodes). Other medical device uses and configurations will be understood by one skilled in the art using the principles described herein.

VII. Selected Embodiments

Parylene Bilayer

The following provides embodiments of the present invention in which a therapeutic layer is embedded between two or more Parylene layers, such as a base layer and an elution layer. The embodiments herein should not be construed as limiting the scope of the invention, and may be utilized in combination with any other embodiments contemplated and/or disclosed throughout the present application.

Certain members of the poly-p-xylenes family, commonly known as Parylene, have been used as coatings for medically implanted devices due to their biocompatibility (Eskin et al. Journal of Biomedical Materials Research, 1976, 10, 113, Fontaine et al. 1996, 3, 276, herein incorporated by reference in their entireties) (USP approved Class VI polymer). The nature of the chemical deposition process (CVD), through which the polymerization of Parylene takes place, allows for the formation of a conformal barrier (Fortin & Lu. Chemical Vapor Deposition Polymerization The Growth and Properties of Parylene Thin Films; Kluwear: Norwell, 2004, herein incorporated by reference in its entirety) between the medical device and exterior environment. Another advantage to the deposition process is that it occurs at room temperature (Dolbier & Beach. Journal of Fluorine Chemistry 2003, 122, 97, herein incorporated by reference in its entirety), preserving device function. Applications of Parylene derivatives such as Parylene C (dichloro(2,2)paracyclophane) and Parylene N ((2,2)paracyclophane) include a range of devices from catheters (Bruck. Blood Compatible Synthetic Polymers CC Thomas: Springfield, 1974, herein incorporated by reference in its entirety) to stents. Recent efforts to supplement the integration of Parylene coated medical devices by applying alternative drug-conjugated polymeric coatings to the Parylene surface, have been successful in the fabrication of drug eluting stents (Westedt et al. Journal of Controlled Release 2006, 111, 235, Unger et al. Journal of Controlled Release 2007, 117, 312, herein incorporated by reference in their entireties). These multi-polymeric coatings complement the biomaterial platform. Developing biocompatible polymeric coatings with a greater degree of biological activity has been a struggle in the field. Experiments were conducted during the development of embodiments of the invention to assess the drug eluting potential of an amine functionalized poly-p-xylene, known as Parylene A (4-amino(2,2) paracyclophane). Murine macrophage cell line RAW 264.7 served as a cellular response to dexamethasone (DEX), a synthetic anti-inflammatory gluco-corticoid, and doxorubicin, an anticancer therapeutic. DEX was used as an example of a therapeutic that can be used with a Parylene A nanofilm. Decrease of NFK-B mediated cytokines, Interleukin-6 (IL-6) and Tumor Necrosis Factor-α (TNF-α), resultant DNA fragmentation, and spectroscopic analysis revealed the drug eluting properties of a Parylene A polymeric bilayer. These experiments demonstrated that Parylene A finds use in drug delivery devices.

Figure 40:
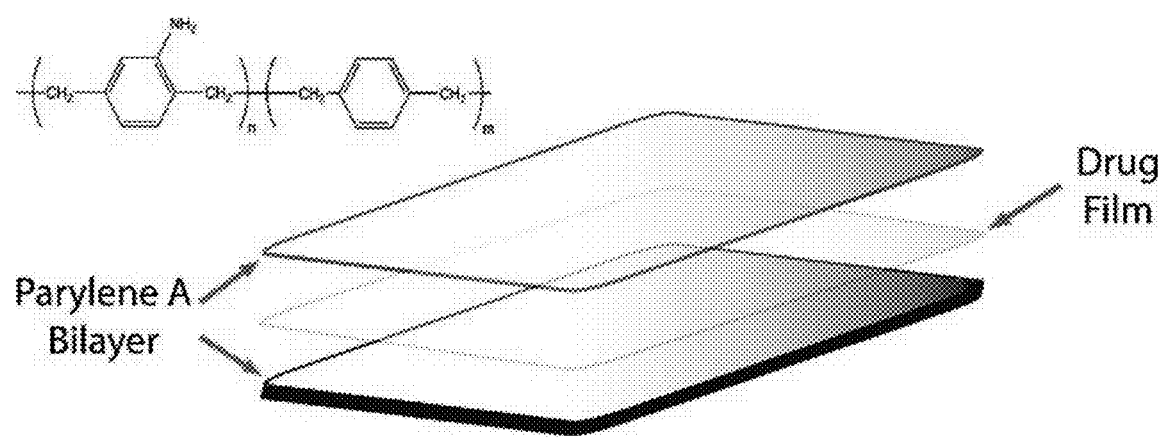
FIG. 40 shows a schematic illustrating the chemical structure Parylene A, and a therapeutic (drug) eluting Parylene A nanofilm device.

For example, experiments were conducted during the development of embodiments of the invention, to expand upon the capability of differentially functionalized poly-p-xylene (Parylene) derivatives, and to examine the drug eluting potential of Parylene A. An exemplary deposition of Parylene A occurred in a two step fashion wherein a coating of dexamethasone (DEX) (anti inflammatory agent) or doxorubicin (DOX) (anti-cancer therapeutic), used as examples of useful therapeutic agents, was dispersed between a primary base layer and a secondary elution layer (SEE FIG. 40). The polymerization reaction of the secondary layer allowed for the elution of therapeutic agents to be examined. The release of the underlying drug was accomplished by restricting the amount of polymer (e.g., Parylene A) available for the deposition process, and depriving the polymerization reaction sufficient material to coat the surface in a conformal manner; pinholes formed as a result, although the present invention is not limited to any particular mechanism of action and an understanding of the mechanism of action is not necessary to practice the present invention. Prior to experiments conducted during the development of embodiments of the invention, an investigation concerning the surface characterization of micro to nanoscale deposition was incomplete; however, reports available revealed the presence of pinholes at or below the micron level (Spellman et al. 1999, 15, 308, herein incorporated by reference in its entirety). Previous work also indicated the elution of underlying material from a nanoscale deposition of Parylene C (Zeng et al. Biomacromolecules 2005, 6, 1484, herein incorporated by reference in its entirety). Experiments were conducted during the development of embodiments of the invention to characterize the disposition, frequency, size, and concentration of pinhole formation within micro to nanoscale Parylene A films. The control over film properties provided by the present invention permits optimization of drug elution over time in a site-specific concentration-dependent fashion.

The application of two different classes of drugs, dexamethasone, an anti-inflammatory and doxorubicin, a chemotherapeutic, revealed an exemplary range of medicinal agents which can be incorporated into a Parylene A polymeric device, although medical agents outside this range may be utilized with the present invention. Experiments conducted during the development of embodiments of the invention demonstrate that drug concentration attained levels comparable to their respective controls, and drug function was retained following the application of the secondary eluting layer. It is contemplated that this platform finds use to present a biocompatible surface with adherent biomolecules (e.g., proteins (De Bartolo et al. Biomolecular Engineering 2007, 24, 23, Lopez et al. Surface and Coatings Technology 2005, 200, 1000, herein incorporated by reference in their entireties) or other biological agents (Hoffman. Clinical Chemistry 2000, 46, 1478, herein incorporated by reference in its entirety), covalently linked to surface amine groups, while maintaining site specific drug eluting properties. A wide range of desired biomolecules or other molecules may be conjugated to the amine groups to provide desired properties to the device.

Figure 44:
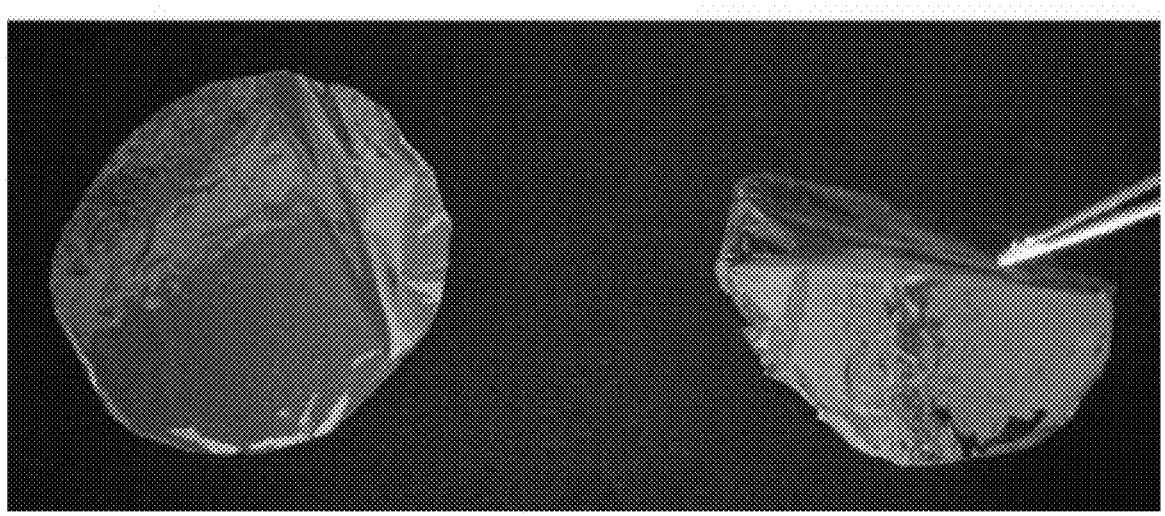
FIG. 44 shows a photo of a Parylene A film revealing its micron thin profile and flexibility.

A Parylene A nanofilm comprising a therapeutic patch (SEE FIG. 44), or providing a coating for a biomedical device, augments existing medical treatments in a non-invasive fashion. Incorporation of an immunosuppressant such as DEX into the coating of a medical device inhibits localized inflammation at the source of implantation, reducing scarring and expediting recovery time. In some embodiments, application of an anti-cancer eluting device, utilizing a chemotherapeutic-eluting Parylene A nanofilm, provides localized delivery of chemotherapeutic agents following post-surgical tumor excision decreasing the incidence of tumor resurgence. Other therapeutic uses and configurations will be understood by one skilled in the art using the principles described herein.

Therapeutic-Functionalized Nanodiamonds within a Bilayer

The following provides embodiments of the present invention in which therapeutic-functionalized nanodiamonds are embedded within the layers of a bilayer, such as a base layer and an elution layer. The embodiments herein should not be construed as limiting the scope of the invention, and may be utilized in combination with any other embodiments contemplated and/or disclosed throughout the present application.

Numerous synthetic and natural nanoscale carriers have been developed and investigated for modulating therapeutic release. These include, but are not limited to polymer-protein conjugates, liposomes, micelles, dendrimers, polyelectrolyte films, co-polypeptides, carbon nanotubes, and variants of the above (Peer et al. Nature Nanotechnology, 2007, 18, 751, Volodkin et al. Soft Matter; 2008, 4, 122, Langer. Science, 1990, 249, 1527, Wood et al. Proceedings National Academy of Sciences, 2006, 103, 10207, Wood et al. Langmuir, 2005, 21, 1603, Deming. Advanced Drug Delivery Reviews, 2002, 54, 1145, Lacerda et al. Advanced Drug Delivery Review, 2006, 58, 1460, herein incorporated by reference in their entireties). Nanodiamonds (NDs) in particular possess several characteristics that make them suitable for advanced drug delivery. NDs with individual diameters of 2-8 nm have been functionalized with doxorubicin (DOX) (Huang et al. Nano Letters, 2007, 7, 3305, herein incorporated by reference in its entirety). Due to their high surface to volume ratio and non-invasive dimensions, extremely high loading capacities of therapeutic were achieved. NDs possess tailorable surface properties and compositions providing the capability to interface with virtually any therapeutic molecule via physical interactions (Huang et al. ACS Nano, 2008, 2, 203, herein incorporated by reference in its entirety). With highly ordered aspect ratios near unity, NDs have been shown to be biologically stable, allowing them to preclude adverse cellular stress and inflammatory reactions. Several reports have confirmed the inherently amenable biological performance of suspended NDs when interacting with cells (Huang et al. Nano Letters, 2007, 7, 3305, Huang et al. ACS Nano, 2008, 2, 203, Schrand et al. The Journal of Physical Chemistry Letters, 2007, 111, 2, Liu et al. Nanotechnology, 2007, 18, 325102, Yu et al. Journal of American Chemical Society, 2005, 127, 17604, herein incorporated by reference in their entireties). The general cellular viability, morphology and mitochondrial membrane is maintained amongst various cell types when incubated with suspended NDs. As such, with appropriate manipulation of drug elution parameters in conjunction with proper selection of material matrices, NDs serve as promising platforms for sustained and localized therapeutic release.

Previous studies functionalizing ND films fabricated via chemical vapor deposition (CVD) with various biological entities have provided exciting prospects for biosensing applications but are nonetheless difficult to implant due to their rigidity (Hartl et al. Nature Materials, 2004, 3, 736, Yang et al. Nature Materials, 2002, 1, 253, herein incorporated by reference in their entireties). Experiments were conducted during the development of embodiments of the present invention to develop an easily fabricated flexible nanofilm device capable of extended localized chemotherapeutic drug delivery. It is contemplated that through targeted slow release, continuously administered small dosages replicate the efficacy of normally larger prescribed amounts, reducing side effects generally associated with systemic chemotherapeutic treatments (Lankelma et al. Clinical Cancer Research, 1999, 5, 1703, Legha et al. Annals of Internal Medicine, 1982, 96, 133, Legha et al. Cancer, 1982, 49, 1762, herein incorporated by reference in their entireties).

Parylene C, a material with well-documented biocompatibility and FDA-approval, was used as an example of a useful, flexible, and robust framework for the path (Hahn et al. Journal of Applied Polymer Science Applied Polymer Symposium, 1984, 38, 55, Yamagishi. Thin Solid Films (Switzerland), 1991, 202, 39, herein incorporated by reference in their entireties). Parylene coatings have been utilized in several medical applications due to their highly conformal nature, biostability and inertness under physiological conditions with no known biological degradation events.

Figure 45:
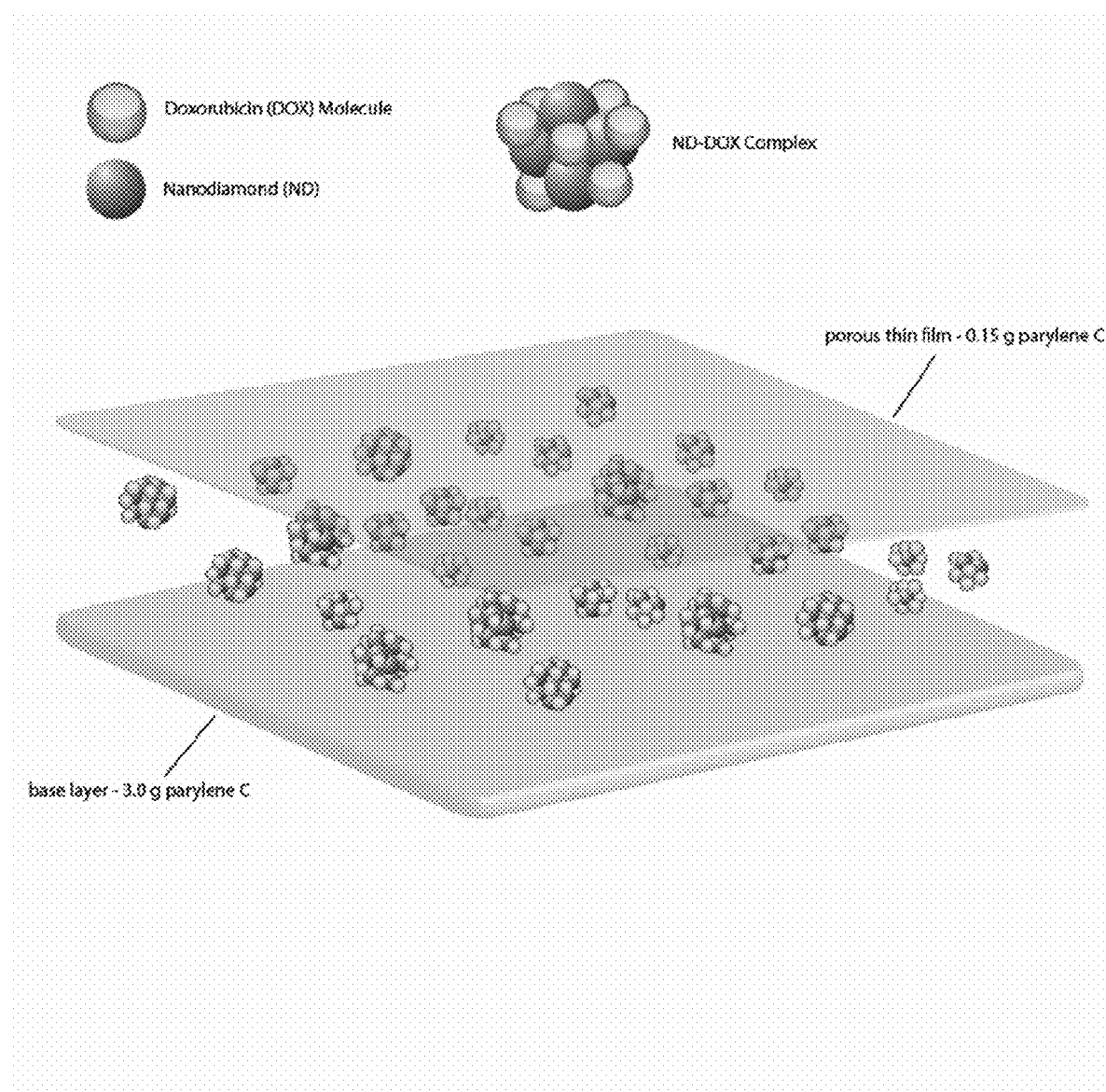
FIG. 45 shows a) an illustrated schematic of a DOX-ND encapsulated Parylene C nanofilm. b) A photograph of DOX-ND encapsulated Parylene C nanofilms with a 10 g base layer, or varied size and shape. c) A demonstration of the flexibility of DOX-ND encapsulated Parylene C nanofilm.

An exemplary hybrid film was made and tested. The hybrid film comprised DOX-functionalized NDs, sandwiched between a thick hermetic base and thin permeable layer of Parylene C (SEE FIG. 45A). NDs efficiently sequestered DOX, and could be released gradually upon appropriate stimuli (e.g. DOX concentration gradients and acidic pH conditions, which have been shown to be indicative of cancerous cells); although the present invention is not limited to any particular mechanism of action and an understanding of the mechanism of action is not necessary to practice the present invention. A permeable top layer of Parylene C acted as an additional physical barrier that further limits and modulates elution. NDs have previously been functionalized with cytochrome c, DNA, and various protein antigens (Huang & Chang, Langmuir, 2004, 20, 5879, Vshizawa et al. Chemical Physics Letters, 2002, 351, 105, Kossovsky et al. Bioconjugate Chemistry, 1995, 6, 507, herein incorporated by reference in their entireties). Experiments have previously demonstrated the ability to functionalize NDs with the apoptosis-inducing chemotherapeutic agent, DOX, and anti-inflammatory immunosuppressant glucocorticoid, dexamethasone. However, to enhance the applicability of the NDs as foundational elements for device fabrication, experiments were conducted during the development of embodiments of the invention to generate a localized elution device to address a broad range of medical conditions including difficulties involving tumor heterogeneity, blood circulation and unsustainable controlled release over a prolonged period of time (Jain, Advanced Drug Delivery Reviews, 2001, 46, 149, herein incorporated by reference in its entirety). Therefore, the ND-Parylene hybrids possess particular significance and relevance towards oncological and anti-inflammatory translation. Furthermore, the biocompatible properties, customization, and localization capacity of the flexible Parylene C encapsulated DOX-ND hybrid film (SEE FIGS. 45B-C), of the present invention, addressed several of these difficulties and provides a method for a wide variety of drug delivery schemes.

Hybrid polymer-ND based films were constructed as a flexible, robust and slow drug release device useful as implants or as stand-alone devices for specific therapies such as antitumor patches. This device configuration provides a platform on which a wide variety of therapeutic drug delivery devices could be developed. These devices also find use in research settings. In some embodiments, two or more therapeutics agents are provided in a device and/or two or more devices each having one agent are utilized. Hybrid films were capable of releasing a continuous amount of drug for at least a month. By altering drug-ND deposition amounts and the thickness of the permeable Parylene layer, dosage amounts and thus, total release times can be calibrated. Since drug release is presumably driven by drug concentration gradients, it is contemplated that the devices can be optimized to reduce elution rates, should the local therapeutic concentration reach a defined threshold. The flexibility of the biocompatible structural material (e.g. Parylene) and the drug sequestering element, NDs, provide an invention with numerous uses involving adjustable and extended timed release with a variety of therapeutics.

Therapeutic-Functionalized Nanodiamonds within Hydrogel Matrix

The following provides embodiments of the present invention in which therapeutic-functionalized nanodiamonds are embedded within a hydrogel matrix. The embodiments herein should not be construed as limiting the scope of the invention, and may be utilized in combination with any other embodiments contemplated and/or disclosed throughout the present application.

Nanodiamonds (NDs) contain several unique features beneficial to potential biomedical applications. Due to the surface characteristics of the diamond surface, ND particles can be functionalized and bound to a variety of biological agents (Huang & Chang. Langmuir, vol. 20, pp. 5879-5884, 2004, Ushizawa et al. Chemical Physics Letters, vol. 351, pp. 105-108, 2002, Kossovsky et al. Bioconjugate Chemistry, vol. 6, pp. 507-511, September-October 1995, Kruger. Angewandte Chemie-International Edition, vol. 45, pp. 6426-6427, 2006, herein incorporated by reference in their entireties) implemented for the capture and separation of specific proteins, and used as fluorescent markers for cell imaging (Yeap et al. Analytical Chemistry, vol. 80, pp. 4659-4665, June 2008, Bondar et al. Physics of the Solid State, vol. 46, pp. 758-760, 2004, Yu et al. Journal of the American Chemical Society, vol. 127, pp. 17604-17605, December 2005, Neugart et al. Nano Letters, vol. 7, pp. 3588-3591, December 2007, Chang et al. Nature Nanotechnology, vol. 3, pp. 284-288, May 2008, herein incorporated by reference in their entireties). In addition, NDs find use in a variety of biocompatibility assays, including evaluation of viability, mitochondrial function, ATP production, and genetic profiles for inflammation (Schrand et al. Journal of Physical Chemistry B, vol. 111, pp. 2-7, 2007, Bakowicz & Mitura. Journal of Wide Bandgap Materials, vol. 9, p. 12, 2002, Liu et al. Nanotechnology, vol. 18, p. 10, August 2007, Huang et al. Nano Letters, vol. 7, pp. 3305-3314, 2007, herein incorporated by reference in their entireties). Developments in breaking up large particle aggregates have further contributed to the potential in applying NDs in biomedical practice (Ozawa et al. Advanced Materials, vol. 19, pp. 120, May 2007, Kruger et al. Carbon, vol. 43, pp. 1722-1730, July 2005, herein incorporated by reference in their entireties).

In addition to the high surface area-to-volume ratio, ND powders contain an abundant amount of defects on their surface, resulting in large surface areas up to 450 $m^2 \, g^{-1}$ (Dolmatov. Uspekhi Khimii, vol. 70, pp. 687-708, 2001, herein incorporated by reference in its entirety). These large surface areas offer advantageous loading capacities for attaching therapeutics, which can be further improved with additional surface modification. Experiments performed during development of embodiments of the present invention impart unique nanoparticle features towards the macroscale by immobilizing NDs within a polymer matrix.

Widely used, poly(ethylene glycol) (PEG) hydrogels have been used to immobilize and release oligonucleotides, proteins, growth factors, drugs, enzymes and various cells (West & Hubbell. Reactive Polymers, vol. 25, pp. 139-147, 1995, Gayet & Fortier. Journal of Controlled Release, vol. 38, pp. 177-184, 1996, Scott & Peppas. Biomaterials, vol. 20, pp. 1371-1380, 1999, Andreopoulos et al. Biotechnology and Bioengineering, vol. 65, pp. 579-588, December 1999, Anseth et al. Journal of Controlled Release, vol. 78, pp. 199-209, 2002, Bhattacharjee et al. Journal of Nanoparticle Research, vol. 4, pp. 225-230, 2002, Gattas-Asfura et al. Journal of Physical Chemistry B, vol. 107, pp. 10464-10469, September 2003, herein incorporated by reference in their entireties). PEG has the desirable properties of biocompatibility, beneficial hydration, and adequate resistance towards protein adsorption and cell adhesion. Furthermore, as it is not easily recognized by the immune system, PEG reduces immunogenetic and antigenic reactions of proteins in vivo (Fuertges & Abuchowski. Journal of Controlled Release, vol. 11, pp. 139-148, 1990, herein incorporated by reference in its entirety). Versatility in controlling PEG concentrations due to innate water solubility and functional group modifications allow uncomplicated fundamental structural modifications towards obtaining desired release kinetics (Kim et al. Pharmaceutical Research, vol. 9, pp. 283-290, 1992, herein incorporated by reference in its entirety).

In some embodiments of the present invention, poly (ethylene glycol) diacrylate (PEGDA) with an average molecular weight of ~575 was utilized within dental compounds and flexible coatings due to its chemical and impact resistance, flexibility, strength and adhesion (Sigma MSDS). In addition, PEGDA has proven biocompatibility, for which it has been implemented as a hydrogel crosslinker and scaffold in tissue applications (Zheng Shu et al. Biomaterials, vol. 25, pp. 1339-1348, 2004, herein incorporated by reference in its entirety).

A myriad of nanoparticle-hydrogel hybrids have been developed (Bhattacharjee et al. Journal of Nanoparticle Research, vol. 4, pp. 225-230, 2002, Gattas-Asfura et al. Journal of Physical Chemistry B, vol. 107, pp. 10464-10469, September 2003, Huang et al. Journal of Controlled Release, vol. 94, pp. 303-311, February 2004, herein incorporated by reference in their entireties). The immobilization of drug conjugated 2-8 nm diameter ND particles (Huang et al. Nano Letters, vol. 7, pp. 3305-3314, 2007, Huang et al. ACS Nano, vol. 2, pp. 203-212, 2008, herein incorporated by reference in their entireties) within a PEGDA polymer capable provided extended drug storage. In particular, NDs bound with the apoptosis-inducing chemotherapeutic, doxorubicin hydrochloride (DOX) demonstrated an easy and direct method of analyzing drug release due to its strong absorbance.

Experiments were performed during development of embodiments of the present invention in which ND:PEGDA hydrogels were demonstrated to concurrently sequester and slow-release drug while avoiding burst release effects. In addition, the gels were fabricated in an expeditious, economical and facile manner, providing high loading capacities without any additional complex steps. PEG in particular has several beneficial characteristics that make it suitable for clinical applications. ND:PEGDA hydrogels have demonstrated utility in biomedical applications, namely in coatings and tissue engineering.

Properties and release characteristics of ND:PEGDA hydrogels can be tailored by varying PEG molecular weight, crosslinking density, the swelling ratio, gel content or functional groups (Priola et al. Polymer, vol. 34, pp. 3653-3657, 1993, herein incorporated by reference in its entirety). In addition, the biocompatibility of the hydrogels can be further improved by altering photoinitiators without any loss in fabrication fidelity or simplicity (Bryant et al. Journal of Biomaterials Science-Polymer Edition, vol. 11, pp. 439-457, 2000, Williams et al. Biomaterials, vol. 26, pp. 1211-1218, 2005, herein incorporated by reference in their entireties).

In experiments performed during development of embodiments of the present invention, after two weeks of incubation, ND:PEGDA hydrogels did not release the bulk of the drug while standard hydrogels released virtually all of their initial reservoirs. Optimal release effects can be achieved by varying pH and degradation rates. In some embodiments, NDs are included with environmental gels that degrade within physiological conditions. In some embodiments, as the surrounding matrix is reduced, therapeutically modified NDs are released with the NDs serving as an antigen delivery vehicle. For example, anti-inflammatories can be adsorbed onto NDs and inserted into hydrogels as a contributive implant coating. For very specific location delivery, micropatterned hydrogels can be formed easily with existing micro-manufacturing techniques and non toxic solvents (Revzin et al. Langmuir, vol. 17, pp. 5440-5447, September 2001, Subramani & Birch. Biomedical Materials, vol. 1, pp. 144-154, September 2006, herein incorporated by reference in their entireties).

EXAMPLES

The following Examples are presented in order to provide certain exemplary embodiments of the present invention and are not intended to limit the scope thereof.

Example 1

Soluble Nanodiamond-Drug Complexes

This example describes the preparation and testing of soluble nanodiamond-drug complexes.
ND-Drug Complex Preparation Samples of NDs (20 mg/ml), ND:Purvalanol A (10:1 ratio—20 mg/ml ND, 2 mg/ml Purvalanol A), and Purvalanol A alone (2 mg/ml) suspended in DMSO were prepared. The DMSO mixtures were diluted 20 fold in water to create a 5% DMSO solution with the various mixtures of ND and drug.

To prepare the ND:4-OHT complexes, 1 mg 4-OHT was solubilized in 174 mM acetic acid in de-ionized water. NDs (10 mg/ml) were sonicated for 4 hours, added to the 4-OHT sample, and thoroughly vortexed to yield a ND:4-OHT conjugate solution (5 mg/mL ND, 0.5 mg/mL 4-OHT). Solvent only (174 mM acetic acid), ND only (5 mg/mL), and 4-OHT only (0.5 mg/mL) solutions were prepared as controls.

UV-Vis Spectrophotometric Characterization of Drug Adsorption/Desorption

Prior to scanning, all samples were diluted to concentrations of 50 µg/mL and 500 µg/mL for 4-OHT and NDs, respectively. All samples underwent centrifugation at 14,000 rpm for 2 hours at 25° C., where the supernatant was then subsequently collected for spectroscopic scans from 200 nm to 600 nm. Drug loading concentrations were determined via ND-complex pull-down experiments which comprised of an initial absorbance reading, then a 2 hour centrifuge of all samples at 25° C. and 14000 RPM followed by a final absorbance reading. The concentration of loaded drug was then calculated by measuring the difference between the initial and final readings.

Transmission Electron Microscopy

TEM was performed by sonicating the ND:4-OHT solution and then pipetting a droplet onto a carbon TEM grid (Ted Pella). Following 2 hours of drying, a JEOL 2100F Field Emission Gun TEM was used for high voltage 200 kV imaging. A pristine ND sample was also imaged via the same protocol.

Particle Size and Zeta Potential Measurement

The particle size and zeta potential of the complexes were measured using a Zetasizer Nano (Malvern Instruments). ND:4-OHT and Dex-ND complexes were prepared in 25% aqueous DMSO as described previously. ND:Purvalanol A complexes were prepared in a similar manner in 5% aqueous DMSO as described previously. The final concentration of ND and therapeutic in all complexes was 1 mg/mL and 0.1 mg/mL, respectively. All size measurements were performed at 25° C. at a 90° scattering angle. Mean hydrodynamic diameters were obtained via cumulative analysis of 11 measurements. The zeta potential measurements were performed using capillary wells at 25° C., and the mean potential obtained via cumulative analysis of 15 measurements.

DNA Fragmentation Assays

A 1:10 dilution of 5% DMSO in water, NDs in 5% DMSO in water (1 mg/ml), ND:Purvalanol A in 5% DMSO in water (10:1 ratio—1 mg/ml ND, 0.1 mg/ml Purvalanol A), and Purvalanol A in 5% DMSO in water (0.1 mg/ml) were added to HepG2 tissue culture cells and grown for 24 hours. The cultured cells were lysed in 500 µL lysis buffer (10 mM Tris-HCl, pH 8.0, 10 mM EDTA, 1% Triton X-100). 30-minute incubations at 37° C. followed separate RNase A and proteinase K treatment. Following phenol chloroform extraction, nuclear DNA was isolated in isopropyl alcohol and stored at −80° C. overnight. The samples were then resuspended in DEPC water following a 70% ethanol wash and electrophoresed using a 0.8% agarose gel, and finally stained with ethidium bromide.

MTT Cell Viability Assay

MCF-7 cells were plated to 50% confluence in 96-well plates in pH 7.1 MEM/EBSS culture media containing 75 ug/mL NDs, or ND:4-OHT complexes (75 ug/mL ND, 7.5 ug/mL 4-OHT). 7.5 ug/mL 4-OHT was used as a positive control. All samples accounted for the 1.31 mM acetic acid associated with the 4-OHT ND complex solution. Cultures were maintained at 37° C., 5% $CO_2$ for 44 hours prior to performing the MTT-based cell viability assay according to the manufacturer's protocol (Sigma-Aldrich). Absorbances were determined at 570 nm using a Safire multiwell plate reader (Tecan) and Magellan software (Tecan). All samples were run in triplicate.

Results

NDs were synthesized, purified, and processed as previously described [22,26]. Fourier transform infrared spectroscopy (FTIR) measurements confirmed the presence of carboxyl groups on the surface which were deposited as a result of acid treatment during the purification process to remove contaminants [26]. The utility of the carboxyl groups was initially hypothesized to contribute to the ability to interface the NDs with drug molecules through physisorption or electrostatic interactions such that the drug could eventually be released upon external stimuli. In this Example, this hypothesis was confirmed via a multitude of drug-ND imaging and characterization experiments, and UV-Vis analysis of drug-ND interfacing, in addition to functionality assays.

Due to its enormous potential as a chemotherapeutic for liver cancer, Purvalanol A was an ideal drug to complex with NDs. Soluble in DMSO, Purvalanol A is a cyclin dependent kinase inhibitor capable of interrupting cell cycle progression. It has been shown to promote death in cell lines that overexpress myc, an oncogene that is often constitutively expressed in cancers. Due to the role of myc in cell proliferation, its overexpression or mutation often leads to cancer. 4-hydroxytamoxifen (4-OHT), a water-insoluble breast cancer therapeutic, was selected as another model drug system due to its demonstrated efficacy against estrogen-relevant cancers. Lastly, Dexamethasone (Dex) was selected as an additional drug model due to its broad clinical relevance as a steroidal anti-inflammatory, among other physiological conditions toward which it is applicable. All ND-drug complexes were demonstrated to be rapidly dispersable in water, indicating the potential applicability of ND platforms as scalable, water-insoluble therapeutic compound delivery agents.

In order to examine the solubility changes with the introduction of NDs, samples of NDs (20 mg/ml), ND:Purvalanol A (10:1 ratio—20 mg/ml ND, 2 mg/ml Purvalanol A), and Purvalanol A alone (2 mg/ml) suspended in DMSO were compared. The DMSO mixtures were diluted 20 fold in water to create a 5% DMSO solution with the various mixtures of ND and drug (FIGS. 1A-1C). Following dilution in water, Purvalanol A precipitated out of solution, producing a turbid liquid (FIG. 1C). The presence of NDs significantly reduced the turbidity of Purvalanol A aqueous solutions, presumably through efficient drug adsorption to the ND surface, which implies a reduction in free Purvalanol A in solution. This surface interface between the NDs and therapeutics has been confirmed for numerous types of drugs in this study (e.g. Doxorubicin, 4-hydroxytamoxifen, Dexamethasone, etc.). While not necessary to understand or practice the present invention, and while not limiting the present invention, it is hypothesized that physisorption is the main interaction between Purvalanol A and the NDs. It has been previously demonstrated the potential for small molecule release by modulating this interaction with the addition and removal of salts.[26] Due to the reversible nature of the Purvalanol A-ND interface, the complexes served as a favorable platform for both initially dispersing the drug in water and facilitating its subsequent release.

4-hydroxytamoxifen (4-OHT) was selected as the second therapeutic for ND-drug complexing given its importance as a triphenylethylene (TPE) treatment strategy for estrogen receptor (ER)-positive breast cancer. 4-OHT is soluble in ethanol and is often prescribed for its localized activity upon the breast even through systemic administration and therapy, which for other drugs can normally result in non-specific effects. 4-OHT administration has been shown to reduce the risk of local recurrence, by preventing introduction of new primary tumors to the breast [37-40].

ND-mediated enhancement of 4-OHT solubility in water was qualitatively examined and confirmed by observing degrees of visibility through vials which contained ND, 4-OHT, and ND:4-OHT samples in 25% DMSO similar to the interfacial test done with Purvalanol A (FIGS. 1D-1F). In addition, to visually confirm ND:4-OHT interfacing, transmission electron microscope (TEM) images of NDs with and without bound 4-OHT were compared (FIGS. 1G-1H). It was clearly observed that an amorphous 4-OHT residue was present upon drug addition to the ND solution (FIG. 1H).

Figure 2A:
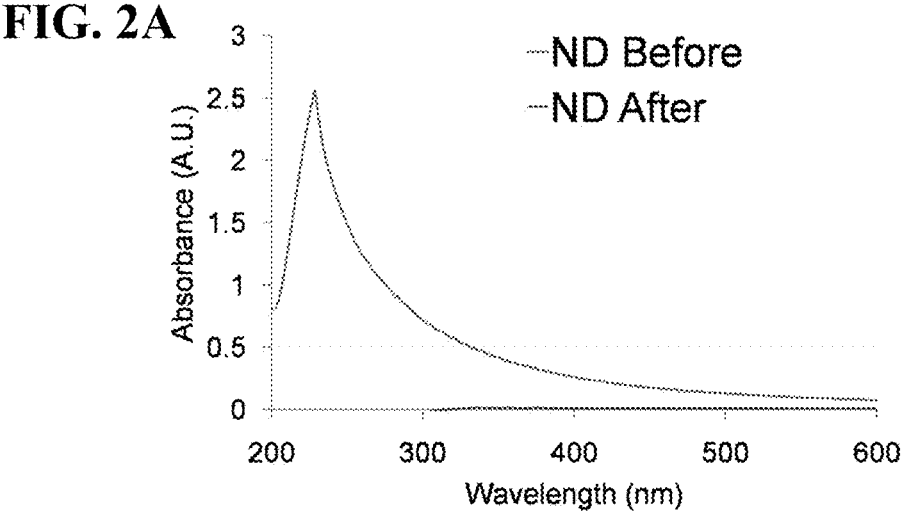
FIGS. 2A-C. UV-Vis spectrophotometric analysis of ND:4-OHT and Dex-ND complex pulldown. A) UV-Vis analysis of ND samples after centrifugation revealed a decrease in UV-Vis absorbance, confirming the ability to utilize the NDs as agents to interface with the 4-OHT and draw the drug into the pelleted ND sample. B) A comparative plot between the UV/Vis absorbance of 4-OHT and ND:4-OHT demonstrates ND and 4-OHT interfacing. The free 4-OHT in solution decreased as a result of physisorption to NDs, which were removed from the aqueous solution via centrifugation. Note there is no observed effect on separating 4-OHT from the aqueous supernatant phase when NDs are absent as illustrated by the overlapping dotted black and solid black lines representing 4-OHT before and after centrifugation, respectively. C) Dex-ND complex formation was also confirmed as shown by the sequestering of Dex following centrifugation.
Figure 2B:
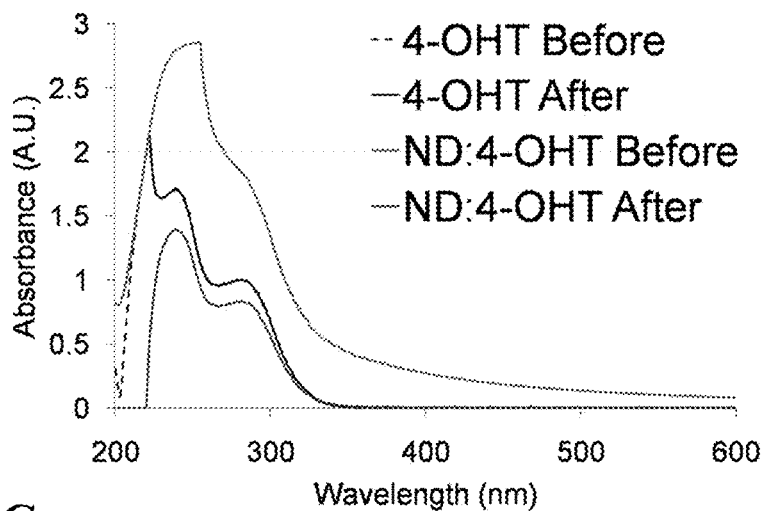
Figure 2C:
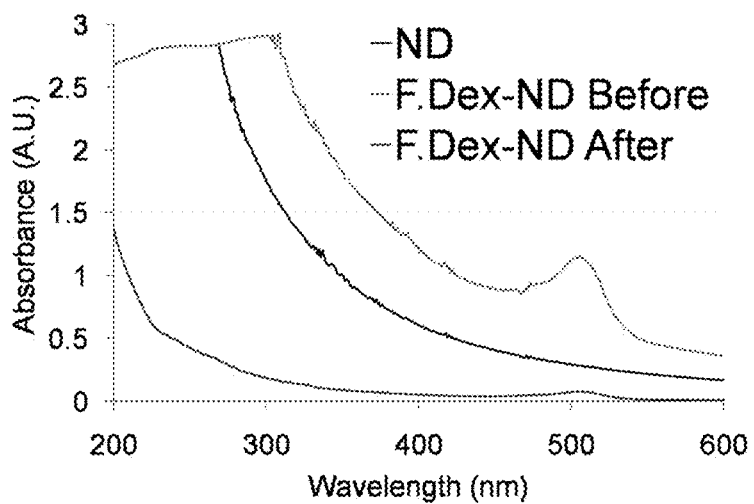

ND:4-OHT interfacing was further confirmed quantitatively via ND pulldown assays coupled with UV-Vis spectrophotometric analysis (FIG. 2). A wavelength scan of uncomplexed NDs revealed that the great majority of NDs pelleted upon centrifugation, leaving little ND remnants behind in the supernatant (FIG. 2A). In contrast, a similar control assay with uncomplexed 4-OHT, before and after centrifugation was performed. An insignificant change in the UV-Vis absorbance demonstrated that in the absence of NDs, the same amount of free 4-OHT resided within the supernatant despite centrifugation (FIG. 2B). This reading served as a control to mark the changes in uncomplexed 4-OHT dispersion due to centrifugation. Therefore, it logically follows that ND:4-OHT complexes would pellet upon centrifugation, and uncomplexed 4-OHT would remain in the supernatant resulting in a decrease in 4-OHT concentration in the supernatant. This conjugation scheme was tested by measuring UV-Vis absorption for ND:4-OHT solutions before and after centrifugation at the same conditions and concentrations as the ND and 4-OHT controls (FIG. 2B). This experiment revealed a marked change in absorbance between the uncentrifuged and centrifuged ND:4-OHT samples, which implied that a significant amount of 4-OHT was pulled down in conjunction with the NDs, possibly through ND:4-OHT physisorption and clustering. These data confirm the observation that NDs enhance the solubility of 4-OHT in 25% DMSO as compared to 4-OHT alone. The same clustering effect was observed in pulldown assays using FITC-labeled Dex-ND complexes (FIG. 2C).

While the present invention is not limited to any particular mechanism and an understanding of the mechanisms is not necessary to practice the invention, similar to the interaction between Purvalanol A and ND, the interplay between 4-OHT and the NDs is also thought to be mainly attributed to physisorption and/or electrostatic in nature. As a result of potential dipoles that exist from the structure of 4-OHT, the presence of surface carboxyl groups could have contributed to the interfacing between the two components in order to preserve ND:4-OHT sequestering.

To determine the physical effects of the electrostatic interactions between NDs and respective therapeutics, the particle sizes and zeta potentials of the complexes were examined via dynamic light scattering (DLS) (FIG. 3). The lack of solubility of the three drugs is ultimately a result of particle aggregation upon titration with water from DMSO. In 5% DMSO, NDs had a mean diameter of 46.96 nm, and Purvalanol A, 4-OHT, and Dex aggregated into 340 µm, 485.1 nm, and 1.245 µm particles, respectively. Upon complexing with NDs, the average Purvalanol A, 4-OHT, and Dex particle sizes decreased to 556 nm, 278.9 nm, and 77.55 nm, respectively (FIGS. 3A-3C). The decrease in particle size for all drugs tested is evidence of physisorption of drug molecules to the surface of the ND particles. These data demonstrate the ability for drug molecules to associate with NDs and as a result, experience a significant decrease in particle size, in some cases by several orders of magnitude.

Figure 3A:
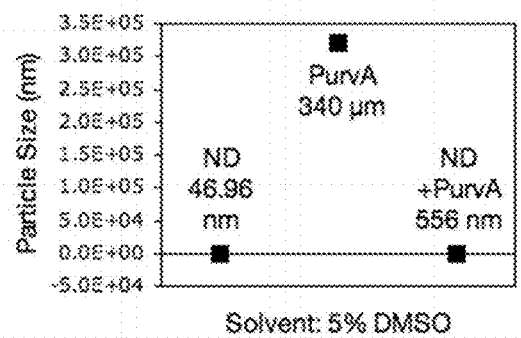
FIGS. 3A-F. DLS analysis of particle size and zeta potential of ND-drug complexes.
Figure 3D:
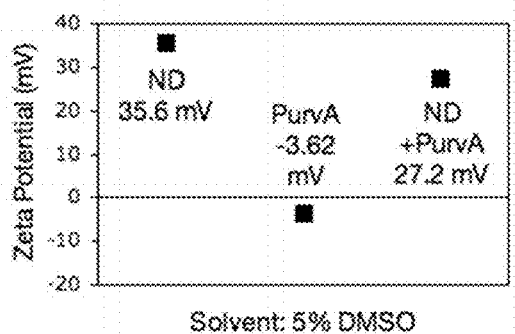
Figure 3B:
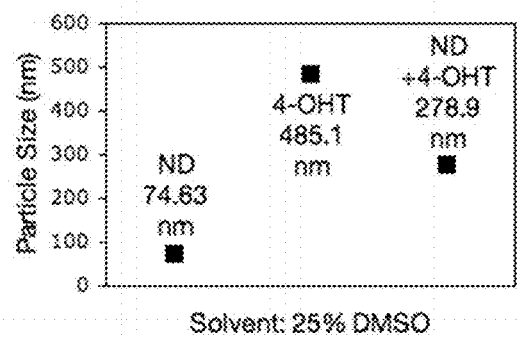
Figure 3E:
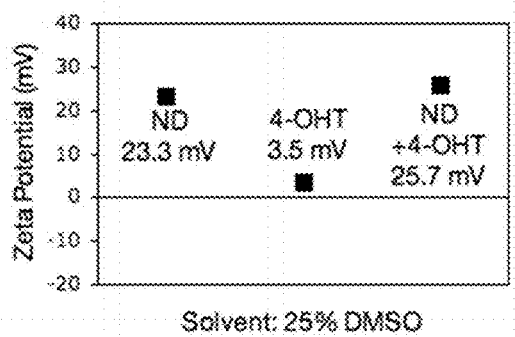
Figure 3C:
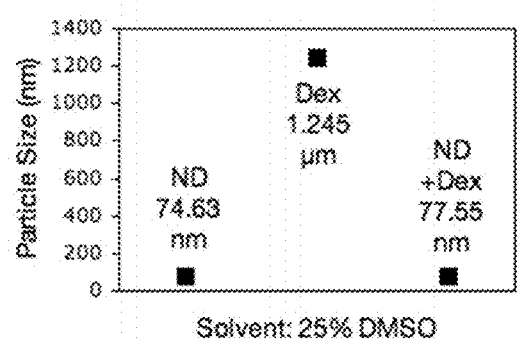
Figure 3F:
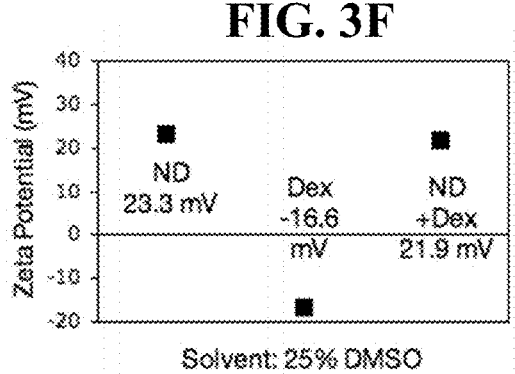

Additionally, the zeta potentials of each drug were shown to become more positive upon association with NDs (FIGS. 3D-3F). This increased zeta potential would contribute to the increased solubility of ND-drug complexes in water due to water molecules having a greater affinity for forming hydration shells around charged complexes compared to neutral molecules.

Moreover, the increased drug solubility that has been demonstrated may also have potential clinical advantages pertaining to increased therapeutic efficacy as it has been shown that cellular internalization is enhanced when particles are both smaller and slightly positively charged [41-42]. Both properties are favorable for internalization across the negatively charged plasma membrane and may facilitate drug uptake via endocytosis and pinocytosis.

Figure 4:
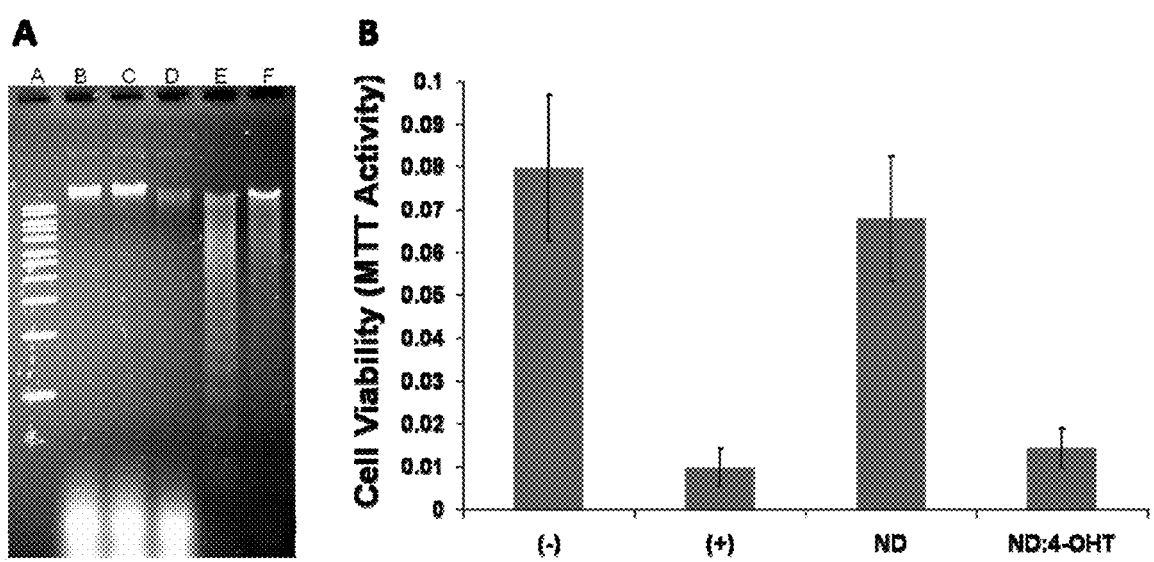
FIG. 4. Therapeutic biofunctionality assays confirm maintained drug activity upon enhanced dispersion via ND complexing. Panel A) Preservation of Purvalanol A activity was confirmed via a DNA fragmentation assay with the following lane designations: A) DNA Marker; B) Negative control (nothing added); C) 5% DMSO in water solution; D) 1 mg/ml ND in 5% DMSO in water solution; E) 1 mg/ml ND, 0.1 mg/ml Purvalanol A in 5% DMSO in water solution; F) 0.1 mg/ml Purvalanol A in 5% DMSO in water solution. Lane E confirmed the potent activity of ND-Purvalanol A complexes. Panel B) MTT cell viability assays were performed to confirm the preserved therapeutic activity of 4-OHT following complex formation with the NDs. The following conditions were examined: (−): negative control; (+): positive control, 7.5 ug/mL 4-OHT; ND: 75 ug/mL ND; ND:4-OHT: 75 ug/mL ND, 7.5 ug/mL 4-OHT. All conditions were in culture media containing 1.31 mM acetic acid. Comparison of cell viability levels between the positive control and ND:4-OHT samples demonstrate preserved 4-OHT potency when complexed to NDs. One representative experiment of three is shown.
Figure 5A:
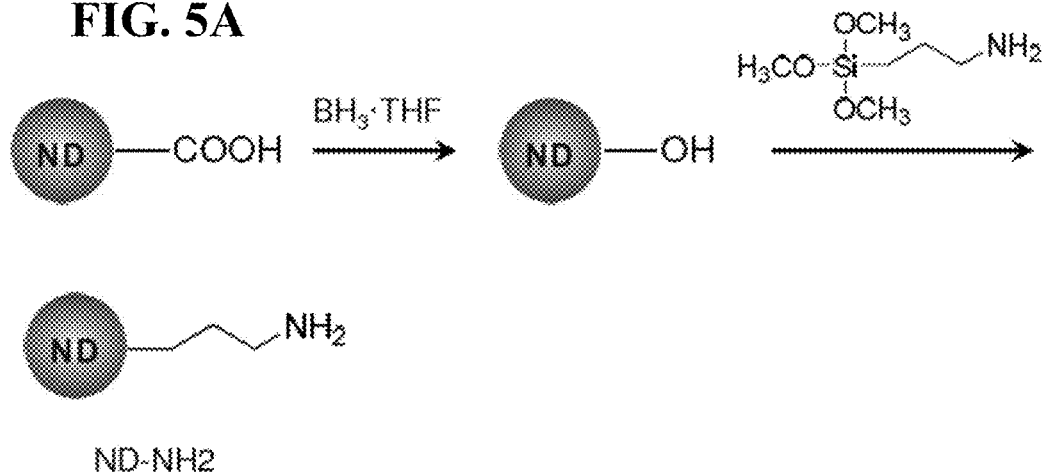
FIGS. 5A and 5B. Schematic illustration of (A) aminofunctionalized nanodiamonds and (B) low molecular weight polyethyleneimine (PEI800) modified nanodiamonds.
Figure 5B:
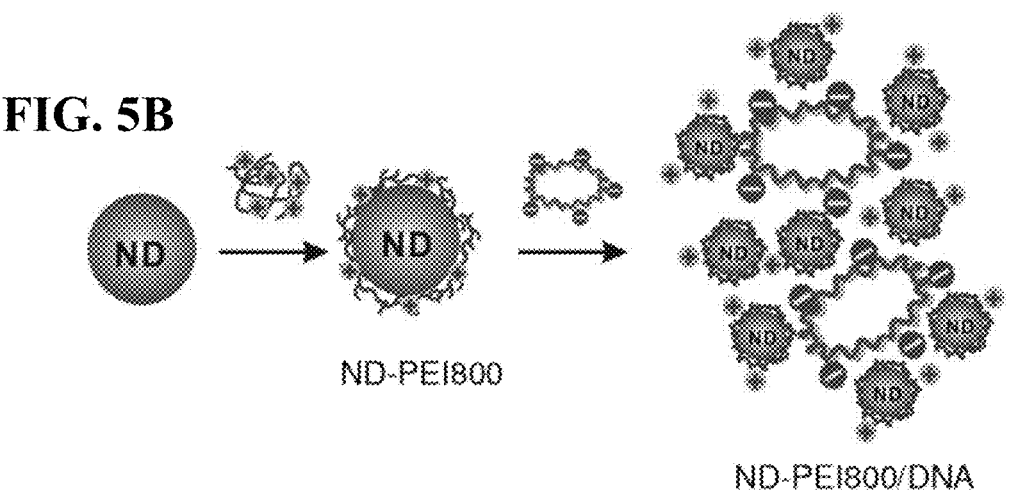
Figure 5B:
Figure 5B:
Figure 5B:
Figure 6:
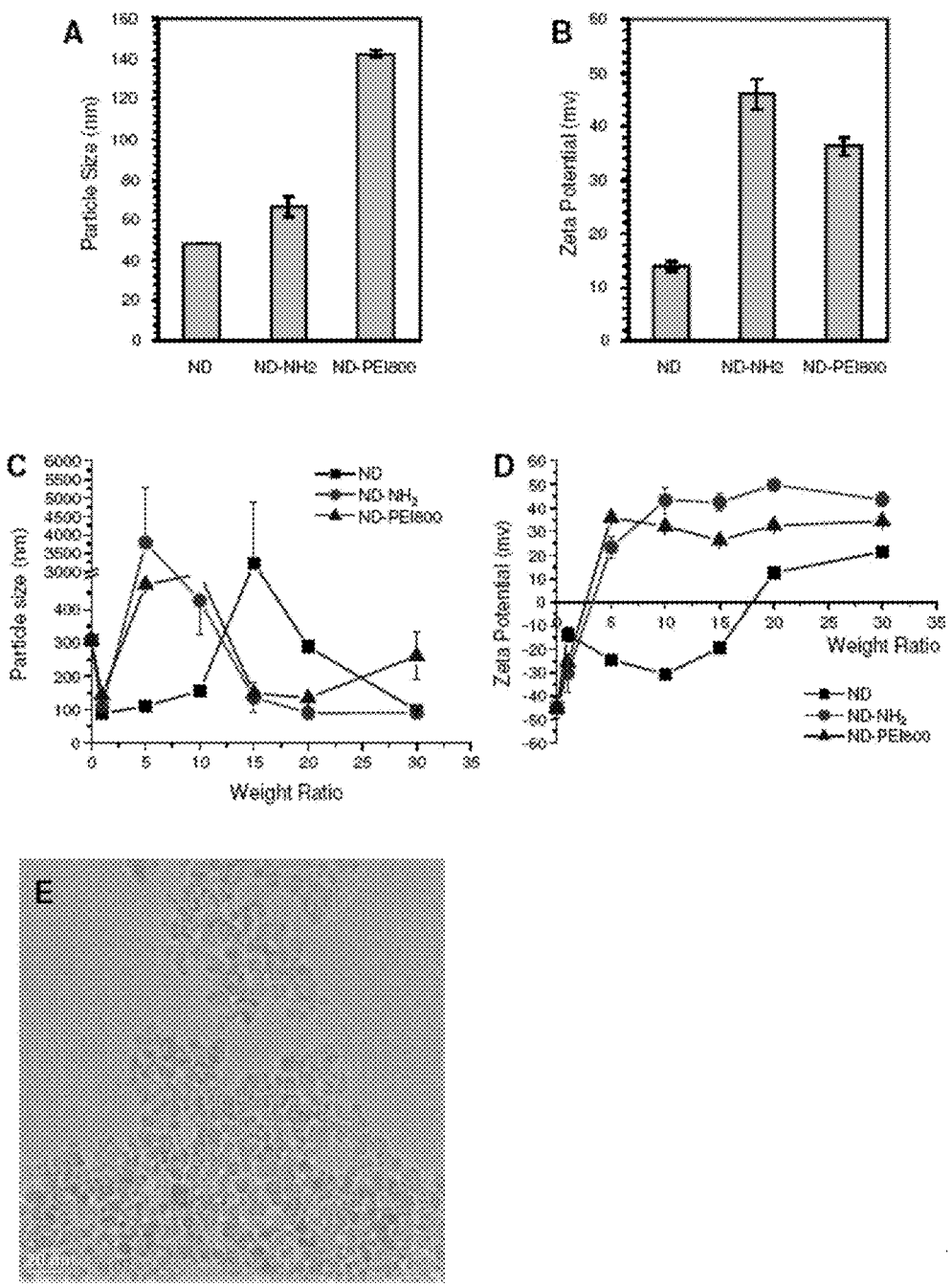
FIG. 6. Size (Panel A) and Zeta potential (Panel B) of nanodiamonds and functionalized nanodiamonds before pDNA binding. The particles were suspended in deionized water at a concentration of 60 ug/ml; Size (Panel C) and Zeta potential (Panel D) of nanodiamonds and functionalized nanodiamonds after pDNA binding with a fixed concentration of 3 ug pDNA/ml. The size measurements were performed using the Zetasizer Nano ZS (Malvern, Worcestershire, United Kingdom) at 25° C. at a 173° scattering angle. The mean hydrodynamic diameter was determined by cumulative analysis. The zeta potential determinations were based on electrophoretic mobility of the particles in the aqueous medium, which was performed using folded capillary cells in automatic mode. Data are represented as the mean±standard deviation (n=2). (Panel E) TEM image of ND-PEI800/DNA. Scale bar is 20 nm.
Figure 7:
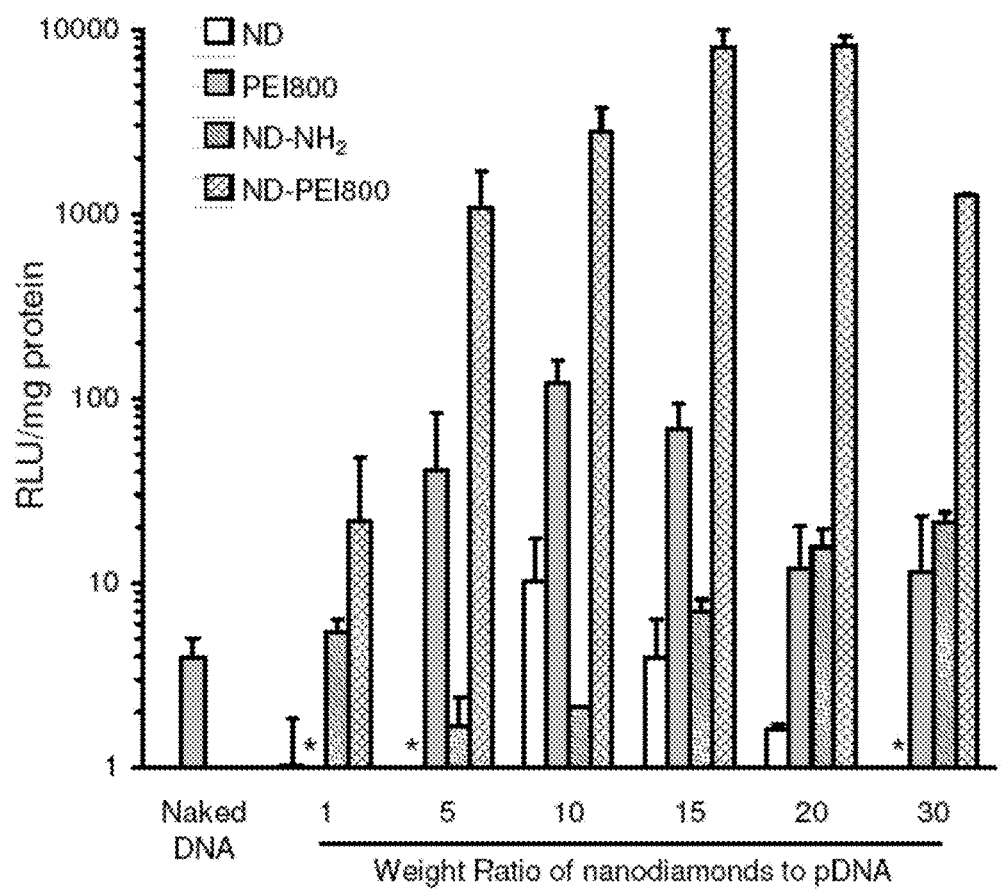
FIG. 7. PEI800 functionalized nanodiamonds mediated efficient gene transfection in HeLa cells. HeLa cells were seeded into 24-well plates at a density of $10^5$/well 24 h before transfection. Nanoparticles were added to the cells and incubated for 4 h at 37° C. Upon washing, cells were further incubated for 44 h. The concentrations of the particles were calculated on the basis of different weight ratios with a target pLuc dose of 3 μg/well. Cell harvesting and luciferase assays were performed 48 h after transfection. Data is represented as a mean±standard deviation (n=2). * represents particles with transfection efficiency lower than 10 RLU/mg of protein in the cell lysate.
Figure 8:
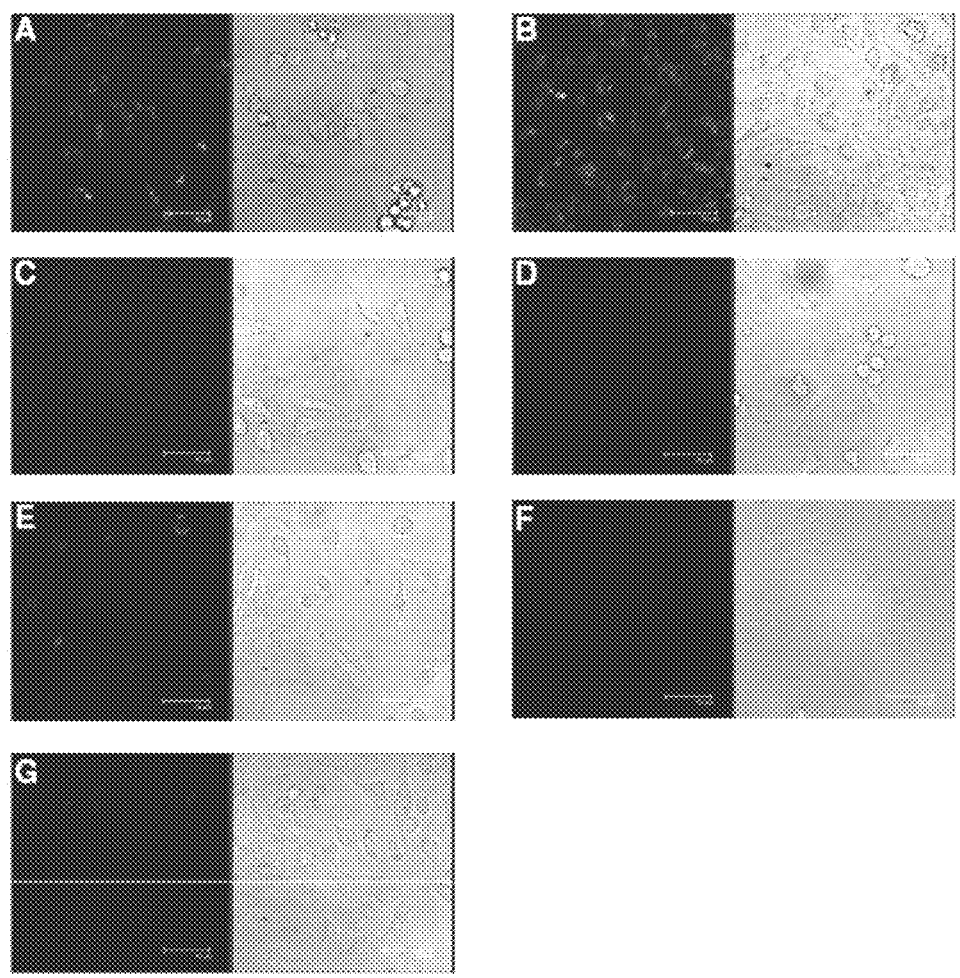
FIG. 8. Bright field and GFP confocal imaging of GFP expression in living HeLa cells mediated by ND-PEI800/pGFP at weight ratio of 5 (A) and 15 (B); unmodified nanodiamonds/pGFP at weight ratio of 5 (C) and 15 (D); PEI800/pGFP at weight ratio of 5 (E) and 15 (F); and naked pGFP (G). HeLa cells were seeded into 24-well plates at a density of $1.5 \times 10^5$/well for 24 h before transfection. Nanoparticles were added to the cells and incubated for 4 h at 37° C. Upon washing, cells were further incubated for 44 h. The concentrations of the particles were calculated on the basis of a target pLuc dose of 6 μg/well. The living HeLa cells were washed by PBS and observed live under confocal microscopy (Leica Inverted Laser Scanning System, Argon Laser excitation 488 nm) 48 h after transfection. (Scale bar: 50 um)

To assess drug functionality following enhanced dispersion in water via ND complexing, DNA laddering assays were performed to confirm Purvalanol A-induced DNA fragmentation (FIG. 4A). Fragmentation was evident in both ND:Purvalanol A and Purvalanol A samples, demonstrating the retained biological activity of Purvalanol after undergoing sequestration to and release from the NDs. As such, the assay attests to the capability of NDs not only to disperse a poorly water-soluble drug in an aqueous solution, but also to maintain Purvalanol A therapeutic activity.

Additionally, the chemotherapeutic effects of the ND:4-OHT complexes were evaluated via MTT cell viability assays (FIG. 4B). FIG. 4B shows no significant difference in cell viability between MCF-7 cultures with and without NDs, which further confirms the reported biocompatibility of NDs. Moreover, comparison of cell viability between ND:4-OHT complexes and the 4-OHT positive control demonstrates that the ND:4-OHT complexes have the same magnitude of chemotherapeutic potency as the drug alone. Exposure to the ND:4-OHT complexes decreased cell viability over seven-fold compared to the negative control and ND cultures. Most importantly, these observations collectively confirm the ability for NDs to increase 4-OHT dispersion in water via formation of a water-soluble ND:4-OHT complex, while maintaining drug functionality.

This Example has demonstrated the application of NDs towards enhancing water-dispersion of poorly water-soluble therapeutics. Purvalanol A and 4-OHT/Dexamethasone were selected as model drugs as they are characteristically soluble in DMSO and ethanol, respectively. Furthermore, due to the functionality of Purvalanol A as a broadly relevant cyclin dependent kinase inhibitor/chemotherapeutic and 4-OHT as a potent breast cancer drug, their enhanced solubility in water is catalytic towards their continued translation to the clinical realm. NDs represent a class of medically-significant nanomaterials that are capable of enabling rapid and high-throughput complex formation with hydrophobic drugs to enable their suspension in water and clinically-relevant applications. As such, NDs serve as scalable platforms that can facilitate facile delivery of these drugs with maintained biocompatibility.

Example 2

Alkaline-Sensitive Nanodiamond-Protein Complexes

This example describes the preparation and testing of nanodiamond-protein complexes.

Cell Culture

The murine cell lines RAW 264.7 macrophages and 3T3-L1 fibroblasts (ATCC Manassas, Va.) were maintained in DMEM (Cellgro, Herndon, Va.) with 1% penicillin/streptomycin (Cambrex, East Rutherford, N.J.) containing 10% FBS (ATCC) and 10% CBS (ATCC), respectively, at 37° C. in 5% $CO_2$. 3T3-L1 fibroblasts were cultured in DMEM supplemented with 10% CBS until reaching 90% confluency, whereupon adipocyte differentiation commenced in accordance to previously established protocols [35, 36]. Media was replaced with DMEM, 10% FBS, 0.86 μM insulin, 0.25 μM dexamethasone and 0.5 mM isobutyl-methylxanthine (IBMX) (Sigma Aldrich St. Louis, Mo.) for 4 days, renewing the media on day 2. Media was replaced on day 4 with DMEM, 10% FBS and 0.86 μM insulin, and again on day 6 with DMEM, 10% FBS for an additional 4 days. Cells were fully differentiated on day 10, and subsequently cultured in DMEM, 10% FBS and 1% penicillin/streptomycin.

Formation of ND-Insulin Complex

Nanodiamonds (NanoCarbon Research Institute Co., Ltd., Nagano, Japan) dispersed in water underwent ultrasonication for 4 hours (100 W, VWR 150D Sonicator) to further disperse ND aggregates. Aqueous insulin was then added to ND solutions at varying ratios and mixed thoroughly to promote insulin binding to the NDs by physical adsorption.

Protein Characterization

FITC-labeled insulin (Sigma-Aldrich) was dissolved in a 1 mM stock solution. Samples were measured using a Beckman Coulter DU730 UV/vis spectrophotometer (Fullerton, Calif.) at peak absorbance of approximately 494 nm (peak varied with solvent). Bovine insulin (Sigma-Aldrich), dissolved in acetic acid (pH 3) and neutralized with 1 mM NaOH, was used to supplement the results from FITC insulin. Protein detection was performed using the Micro BCA Protein Assay Kit (Thermo Scientific, Rockford, Ill.), measuring absorbance at 562 nm.

FT-IR and TEM Characterization

A 4:1 ratio of NDs to insulin was prepared, centrifuged at 14,000 rpm for 2 hours and the supernatant removed. The ND-insulin pellet was rinsed with water and dried under vacuum. Individual ND and insulin samples were also prepared by dehydrating each respective solution. Additionally, a sample of NaOH-treated ND-insulin was made for TEM imaging by adding 1 mM NaOH adjusted to pH 10.5 to ND-insulin, centrifuging for 2 hours at 14,000 rpm and isolating the ND pellet. Samples were characterized at room temperature using a Thermo Nicolet Nexus 870 FT-IR spectrometer and a Hitachi H-8100 TEM (Pleasanton, Calif.).

DLS Analysis

Hydrodynamic size and zeta potential of samples was measured with a Zetasizer Nano (Malvern Instruments, Worcestershire, United Kingdom). NDs and insulin were prepared as previously described. Briefly, the particles were suspended in buffer with corresponding pH at a concentration of 50 mg/mL. The size measurements were performed at 25° C. and at a 173° scattering angle. The mean hydrodynamic diameter was determined by cumulative analysis. The zeta potential determinations were based on electrophoretic mobility of the microparticles in the aqueous medium, which was performed using folded capillary cells in automatic mode.

Insulin Adsorption and Desorption

Determination of insulin adsorption to NDs was performed by protein detection assays before and after centrifugation. Insulin was added to a ND suspension, centrifuged at 14,000 rpm for 2 hours and the resultant solution extracted and quantified. Detection of desorbed insulin was performed by adding alkaline solutions of 1 mM NaOH, adjusted for varying pH, to samples of ND-insulin in suspension. Binding ratios were determined similar to the adsorption test.

Additionally, a 5-day desorption test was conducted to determine cumulative insulin release. Samples were prepared by combining NDs and insulin (4:1 ratio), centrifuging at 14,000 rpm for 2 hours and extracting the remaining solution to remove any non-adsorbed insulin. Subsequently, a 1 mM NaOH solution adjusted to pH 10.5 was added to the samples, mixed thoroughly and centrifuged after a 24-hour period to determine protein concentration utilizing a BCA assay. In addition to alkaline-mediated release, water was added to a separate set of samples. The samples were replenished with NaOH or water after each measurement for the respective conditions, and the process was repeated every 24 hours over the course of 5 days.

MTT Cell Viability Assay

RAW 264.7 murine macrophages were plated in 96-well plates, serum-starved for 8 hours and then incubated for 24 hours. Post-starvation media was composed of the following conditions: DMEM, 0.1 µM insulin, 1 µM insulin, DMEM 10% FBS, approximately 0.1 µM insulin released from ND-insulin complex by NaOH at pH 10.5 (insulin present in media), resultant solution from centrifuged ND-insulin in water, ND-insulin treated with NaOH at pH 10.5 (1 µM total insulin, ND-insulin complex present in media) and ND-insulin (1 µM total insulin, ND-insulin complex present in media). Insulin released from NDs was prepared by centrifuging samples of NDs with adsorbed insulin in NaOH and extracting the resultant solution, which could be reconstituted with media to 0.1 µM insulin. In a similar fashion, water was utilized as a neutral solution for relevant desorption analysis. Methylthiazolyldiphenyl-tetrazolium bromide (MTT) solution (Sigma-Aldrich) was added corresponding to 10% of total volume, and then incubated for 3 hours. After formazan crystal formation, the media was removed and MTT solvent, 0.1N HCl in anhydrous isopropanol (Sigma-Aldrich), was added to samples to solubilize the MTT dye. Sample absorbance measurements occurred at 570 nm, accounting for background at a wavelength of 690 nm.

Quantitative RT-PCR

RT-PCR procedures were conducted as described previously [35]. 3T3-L1 adipocytes were plated in 6-well plates, serum-starved for 4 hours and then recovered in media solutions of DMEM, insulin, approximately 0.1 µM insulin released from ND-insulin by NaOH (pH 10.5), resultant solution from centrifuged ND-insulin in pH-neutral water, ND-insulin treated with NaOH (1 µM total insulin) and NDs with bound insulin (ND-insulin, 1 µM total insulin). Preparations of media solutions containing DMEM, insulin, NDs and NaOH were conducted in a similar fashion to those implemented for the MTT assay. RNA isolation was completed by lysing cells with TRIzol reagent (Invitrogen Corporation, Carlsbad, Calif.) and added to chloroform to obtain genetic material by centrifugation. cDNA synthesis was performed using the iScript Select cDNA Synthesis Kit (Bio-Rad, Hercules, Calif.). PCR expression of the Ins1 and Csf3/G-csf genes (Integrated DNA Technologies, Coralville, Iowa) were quantified by the MyiQ Single Color Real-Time PCR machine (Bio-Rad, Hercules, Calif.) using SYBER Green detection reagents (Quanta Biosciences, Gaithersburg, Md.). The Rpl32 gene (Integrated DNA Technologies) served as the housekeeping gene for normalization of cDNA among samples. The primer sequences for genes are given:

Ins1,
(SEQ ID NO: 1)
5'-AGGTGGCCCGGCAGAAG-3'
and (SEQ ID NO: 2)
5'-GCCTTAGTTGCAGTAGTTCTCCAGCT-3';

Csf3/G-csf,
(SEQ ID NO: 3)
5'-CCAGAGGCGCATGAAGCTAAT-3'
and (SEQ ID NO: 4)
5'-CGGCCTCTCGTCCTGACCAT-3';

Rpl32,
(SEQ ID NO: 5)
5'-AACCGAAAAGCCATTGTAGAAA-3'
and (SEQ ID NO: 6)
5'-CCTGGCGTTGGGATTGG-3'.

FT-IR and TEM

Figure 9:
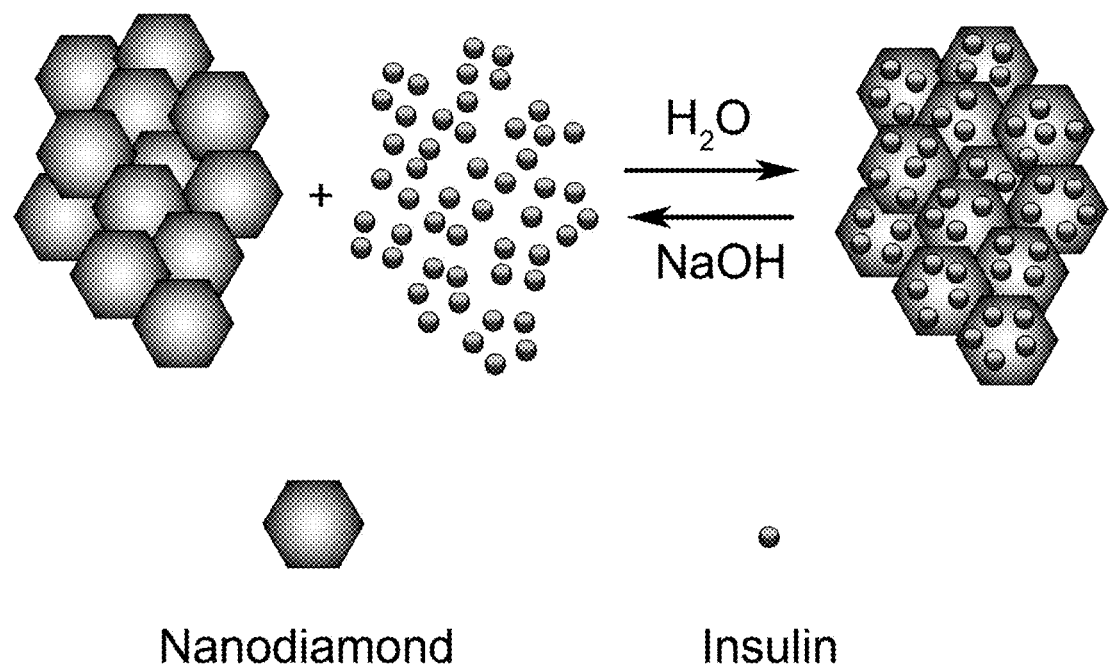
FIG. 9. A hypothetical schematic illustration showing insulin adsorption to NDs in water and desorption in the presence of NaOH. Insulin non-covalently binds to the ND surface in water by means of electrostatic and other interactions. The shift to an alkaline environment alters the insulin surface charge characteristics, thereby causing release from the ND surface.
Figure 10:
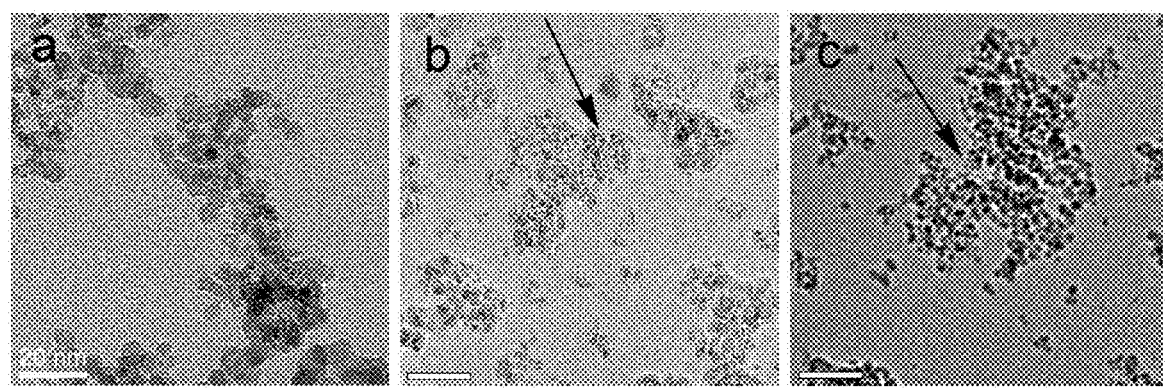
FIG. 10. TEM images of (a) bare NDs, (b) NDs with adsorbed insulin in aqueous solution and (c) NDs with adsorbed insulin after treatment with 1 mM NaOH adjusted to pH 10.5. There is an apparent layer or coating on the surface of NDs (b), as compared to bare NDs (a), with a thickness of approximately 5-10 nm. Seeing as the addition of insulin was the only difference in sample preparation between (a) and (b), the visible layer may indicate insulin adsorption. The material is not present on the NaOH-treated NDs (c). The scale bar represents 20 nm in (a) and 50 nm in (b, c).

While the present invention is not limited to any particular mechanism and an understanding of the mechanism is not necessary to practice the present invention, illustrated in FIG. 9 is a representation of the proposed mechanism of insulin adsorption and desorption in neutral and alkaline solutions, respectively. Transmission electron microscopy (TEM) images in FIG. 10 show bare NDs (a), NDs with adsorbed insulin (b) and the ND-insulin complex after treatment with NaOH (c). In (b) there is an apparent layer of material coating the NDs approximately 5-10 nm in thickness. The NaOH-treated ND-insulin sample (c) qualitatively shows a diminished layer of material on the NDs, suggesting NaOH treatment of ND-insulin removed the material present on the ND surface. Fourier transform infrared (FT-IR) spectroscopy (FIG. 11) suggests the presence of insulin on NDs. Samples of insulin (1), bare NDs (2) and ND-insulin (3) are shown, with spectra peaks on ND-insulin indicating characteristic peaks similar to insulin.

DLS Analysis

Figure 12:
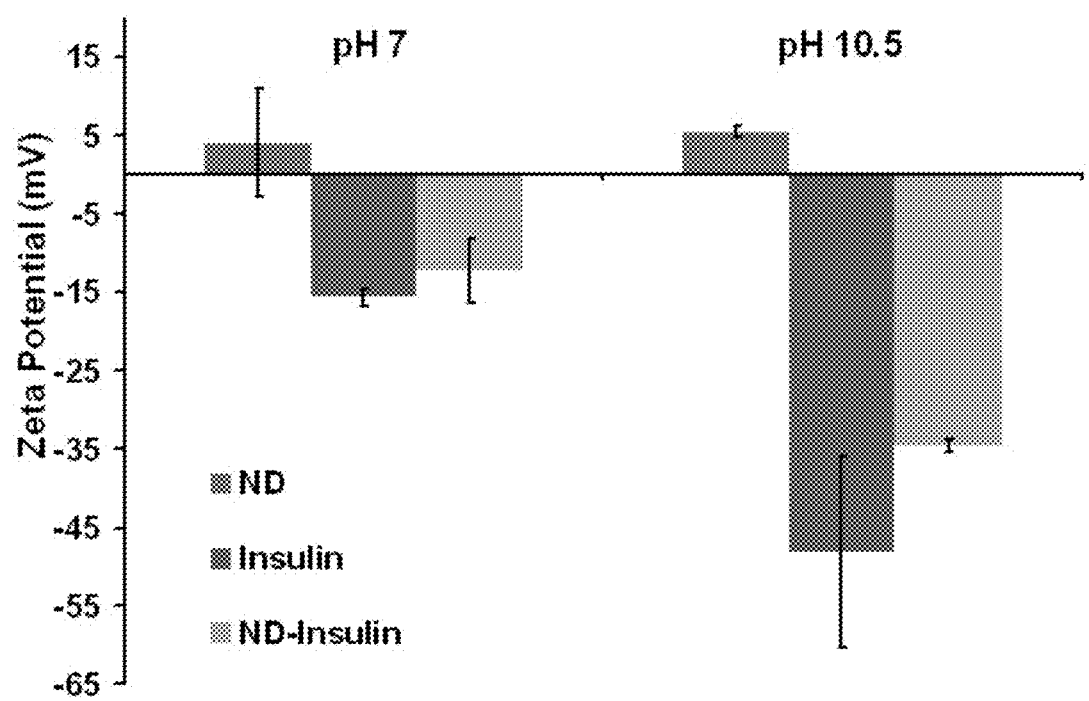
FIG. 12. Zeta potential changes associated with insulin and ND complexing at pH 7 and pH 10.5. NDs reveal a slightly positive zeta potential at both pH values, compared to the negative potential of insulin and the ND-insulin complex. The apparent difference in zeta potential between NDs and the ND-insulin complex implies an interaction between NDs and insulin.

The interaction between NDs and insulin was characterized by means of dynamic light scattering (DLS) analysis, revealing hydrodynamic nanoparticle cluster size and polydispersity index summarized in Table 1 and zeta potential illustrated in FIG. 12. Average ND cluster size remained similar at pH 7 and 10.5, whereas insulin showed a larger average size at pH 10.5. The ND-insulin complex demonstrated an average size comparable to bare NDs and a decreased polydispersity index. NDs exhibited a slightly positive zeta potential at both pH 7 and 10.5, while insulin and ND-insulin resulted in negative values. The zeta potential of insulin and ND-insulin at pH 10.5 was substantially more negative than similar samples at pH 7.

Adsorption

Figure 13:
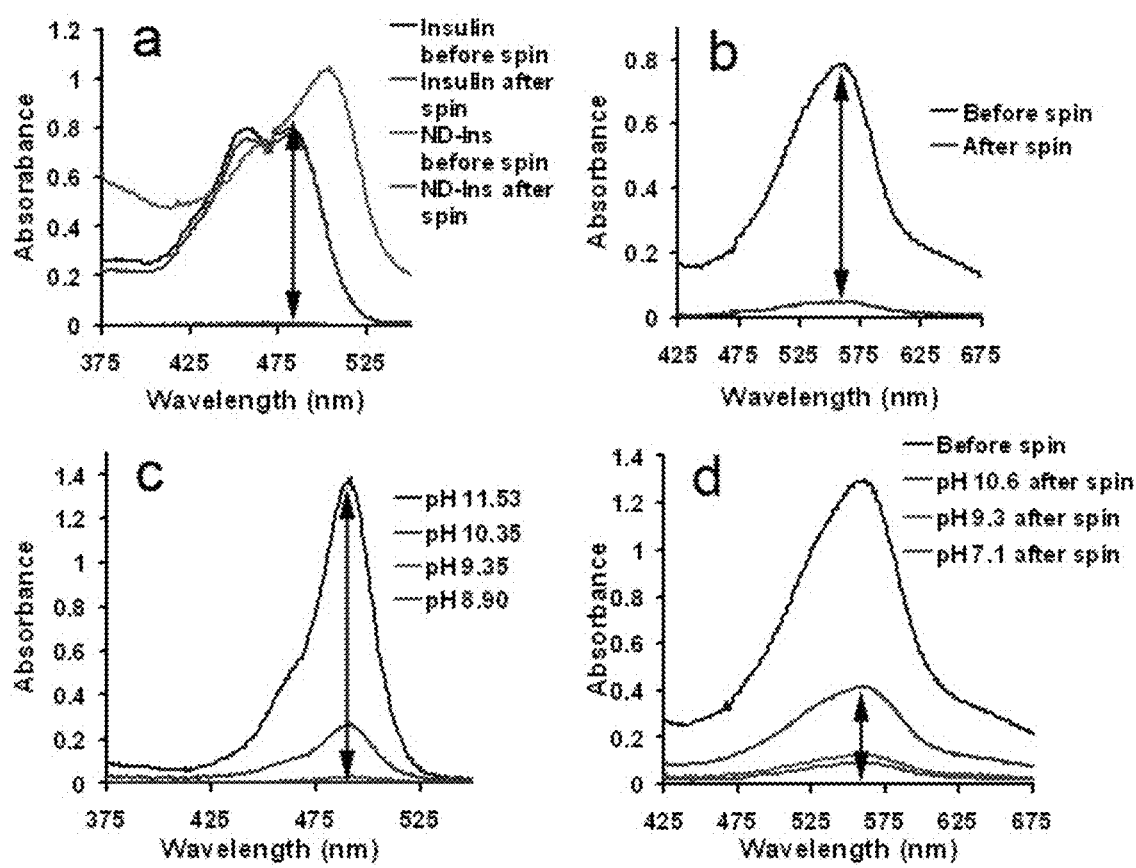
FIG. 13. UV/vis quantification of the adsorption and desorption of insulin from NDs. (a) Adsorption of FITC insulin to NDs is noted by the differential absorbance values attained between the initial and centrifuged ND-insulin, measured at 485 nm. (b) Absorbance of bovine insulin implementing the BCA protein assay, measured at 562 nm. (c) Desorption of FITC insulin from NDs in 1 mM NaOH adjusted to various pH values. Samples were centrifuged under alkaline conditions, and the resultant solution measured. (d) Desorption of bovine insulin from NDs using the BCA protein assay. From the release absorbance spectra, greater amounts of insulin are desorbed in alkaline environments, suggesting NaOH affects the charge characteristics of insulin.

FIG. 9 shows a hypothetical schematic of how insulin in neutral solutions will bind by physical adsorption to NDs. FITC insulin samples of varying concentrations were mixed thoroughly with 100 µg/mL NDs to promote adsorption. Absorbance spectra for ND-insulin (FIG. 13-a) differ from that of aqueous insulin due to the adsorption of insulin to NDs. The ND-insulin complex, however, retains the spectral characteristics necessary to quantify the presence of insulin. The molecular weight of NDs, in addition to any adsorbed material, allows for the separation of components via centrifugation. Separation and analysis of remaining solutions yields supporting data concerning loading capacity and resultant release from NDs. FIG. 13-*a* illustrates protein adsorption of FITC insulin at a 5:1 ratio of NDs to insulin, demonstrating 89.8±8.5% binding in water. ND-insulin and insulin samples were measured before and after centrifugation, resulting in lower insulin concentrations of the ND-insulin sample as compared to the insulin sample due to centrifugation.

A similar test was conducted using standard bovine insulin implementing the BCA protein assay. Adsorption of 25 µg/mL insulin to 100 µg/mL NDs (4:1 ratio of NDs to insulin) demonstrated 79.8±4.3% binding, taking into account the pull-down effect of centrifugation on insulin. FIG. 13-*b* shows the absorbance spectra for ND-insulin samples before and after centrifugation, with peak absorbance at 562 nm. The absorbance of the centrifuged sample is significantly lower than that of the initial sample.

Protein binding ratios were determined by calculating the difference in absorbance between initial and centrifuged samples, and subtracting the difference in initial and centrifuged insulin control. The insulin control must be taken into consideration due to the slight gradient formed when insulin is centrifuged.

Desorption

The desorption assays were conducted in a similar manner as the adsorption assays. Aqueous solutions of FITC-labeled and standard insulin were added to ND suspensions at 5:1 and 4:1 ratios, respectively. Initial and centrifuged samples were measured, and the amount of insulin desorbed was calculated. Comparing released FITC insulin at pH values of 8.90, 9.35, 10.35 and 11.53, maximum desorption was demonstrated at the most alkaline pH (FIG. 13-*c*). Separate tests at pH 10.7 show the ND-insulin complex achieving 53.3±1.2% desorption. Standard insulin release from NDs at pH 7.1, 9.3 and 10.6 also showed the greatest elution occurred at a pH of 10.6 (FIG. 13-*d*). This desorption profile shows that insulin release demonstrates proportionality to the pH of solution. Separate tests conducted with NDs and insulin at a 4:1 ratio in the presence of NaOH at pH 10.5 resulted in a 31.3±1.6% release of insulin.

Figure 14:
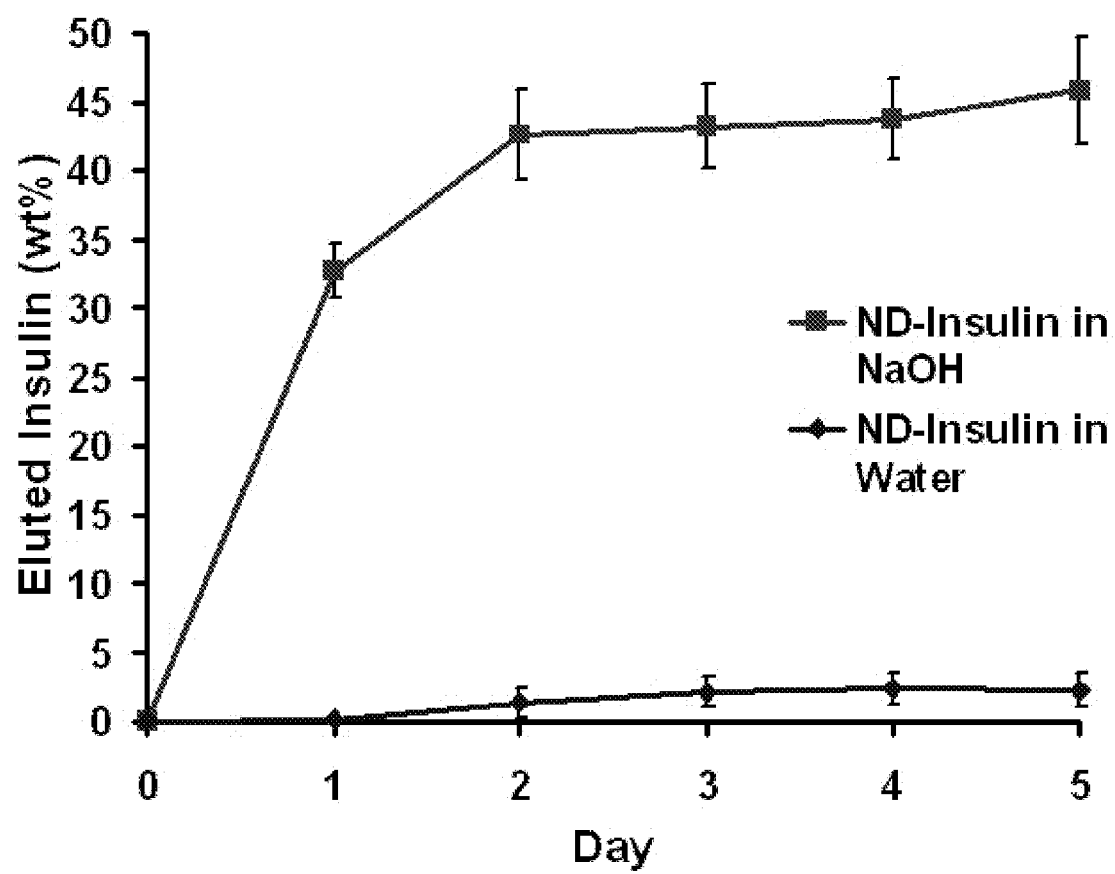
FIG. 14. Five-day insulin desorption test of ND-insulin samples treated with NaOH (pH 10.5) and water, showing insulin release in an alkaline pH environment. The cumulative weight percentage of released insulin was measured. The NaOH samples show increased desorption within the first 2 days and then a leveling-off of the amount released for a total desorption of 45.8±3.8%. Samples treated with water, however, released only a fraction of insulin totaling 2.2±1.2%. The majority of insulin released by NaOH occurred by day 1, indicating the alkaline solution had its maximal effect on fully-adsorbed NDs.

FIG. 14 illustrates the release of insulin from NDs over a period of 5 days in NaOH (pH 10.5) and water. Cumulative insulin eluted was quantified by weight percentage of total adsorbed insulin. The amount of insulin released by day 1 from alkaline conditions (pH 10.5) was 32.7±1.9 wt % compared to that of the water sample of 0.2±0.1 wt %, revealing a considerable difference in release between the two samples. By day 3 both samples tended to plateau and release significantly less insulin, and by day 5 the total amount of insulin eluted by NaOH and water was 45.8±3.8 wt % and 2.2±1.2 wt %, respectively. These values denote more than 20 times the amount of insulin released from the samples containing NaOH than those containing water.

MTT Cell Viability Assay

Figure 15:
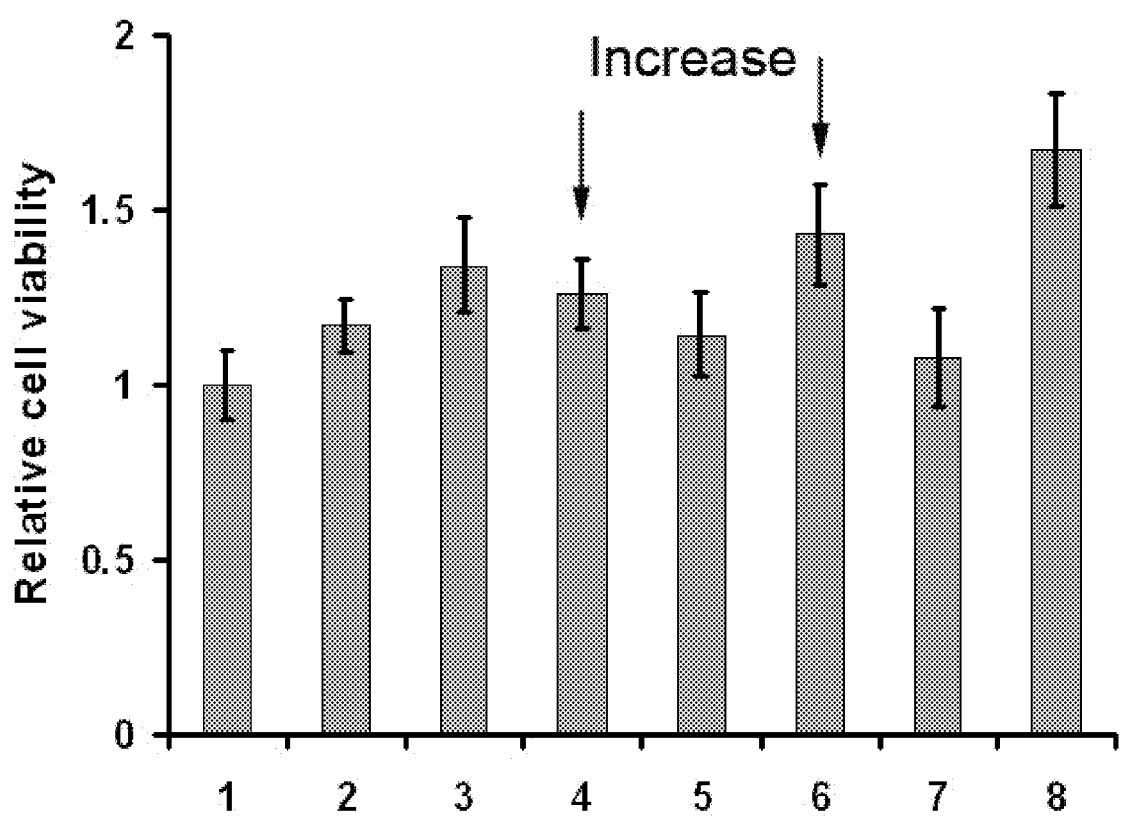
FIG. 15. MTT cell viability assay of RAW 264.7 macrophage cells under varying media conditions. Cells were serum-starved for 8 hours, followed by a 24-hour recovery period with the indicated media solutions: (1) DMEM, (2) 0.1 μM insulin, (3) 1 μM insulin, (4) approximately 0.1 μM insulin released from ND-insulin by NaOH (pH 10.5), (5) resultant solution from centrifuged ND-insulin in water, (6) ND-insulin treated with NaOH (1 μM total insulin), (7) NDs with bound insulin (ND-insulin, 1 μM total insulin) and (8) DMEM 10% FBS. Relative viability of ND-insulin treated with NaOH (6) was similar to that of high insulin concentration (3) demonstrating effective recovery with the released insulin. Insulin released by NaOH (4) showed higher relative viability than that of insulin released by water (5), signifying a greater desorption via alkaline solutions. ANOVA statistical analysis gave $P<0.01$, representing a significant difference among groups.

Cell viability tests under different insulin and ND conditions were performed (FIG. 15): DMEM (1), 0.1 µM insulin (2), 1 µM insulin (3), approximately 0.1 µM insulin released from ND-insulin complex by NaOH (pH 10.5) (4), resultant solution from centrifuged ND-insulin in water (5), ND-insulin treated with NaOH (1 µM total insulin) (6), NDs with bound insulin (ND-insulin, 1 µM total insulin) (7) and DMEM 10% FBS (8). Note that the amount of insulin adsorbed to NDs for both ND-containing samples is equal to 1 µg in media if insulin completely dissociates from the ND surface. Significantly higher relative viability occurred from 0.1 µM (2) to 1 µg (3) insulin, inferring increased viability at higher insulin concentrations. Relative viability for insulin released from ND-insulin by NaOH (4) is comparable to a relative viability between that of 0.1 µM to 1 µg insulin. Insulin desorbed by water (5) showed relative viability similar to that of 0.1 µM insulin, despite previous desorption results revealing insignificant levels of insulin in the resultant solution. ND-insulin treated with NaOH (6) demonstrated improved relative viability, greater than that of 1 µg insulin but less than 10% FBS media. ND-insulin (7) resulted in low relative cell viability comparable to DMEM and insulin released by water. For the ND-insulin treated with NaOH and ND-insulin conditions, NDs were present in the media during the recovery period allowing for cellular interactions with the NDs as compared to similar samples absent of NDs. Regular culture media, 10% FBS in DMEM (8), reflected the highest relative viability. An analysis of variance (ANOVA) statistical test was conducted yielding $P<0.01$, indicating a significant difference among sample groups.

Quantitative RT-PCR

Figure 16:
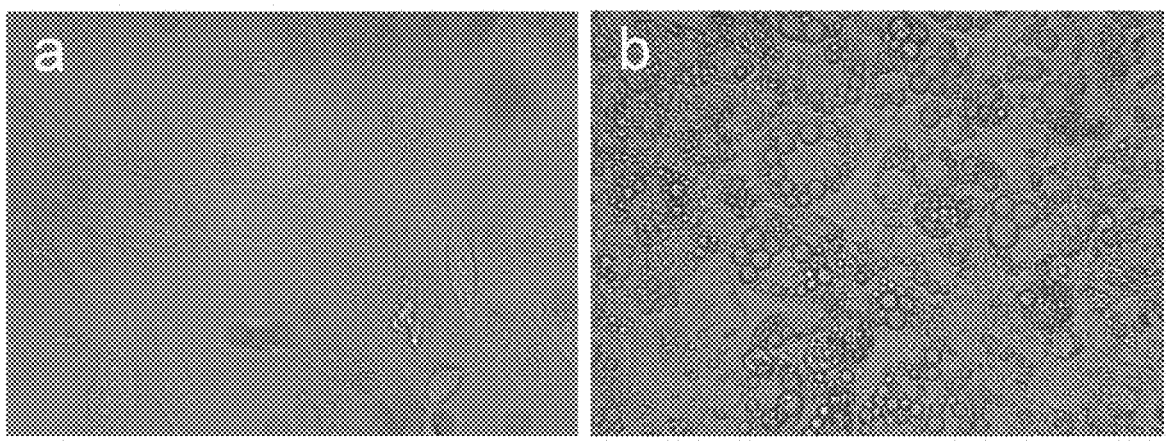
FIG. 16. (a) 3T3-L1 pre-adipocytes and (b) differentiated adipocytes, showing a clear difference in morphology between the two cell types. The pre-adipocyte fibroblast cells undergo differentiation upon supplementing media with insulin, dexamethasone and IBMX, becoming fully differentiated by day 10 post-induction. Lipid vesicle formation occurs during differentiation and can be seen in (b). 250× magnification.
Figure 17:
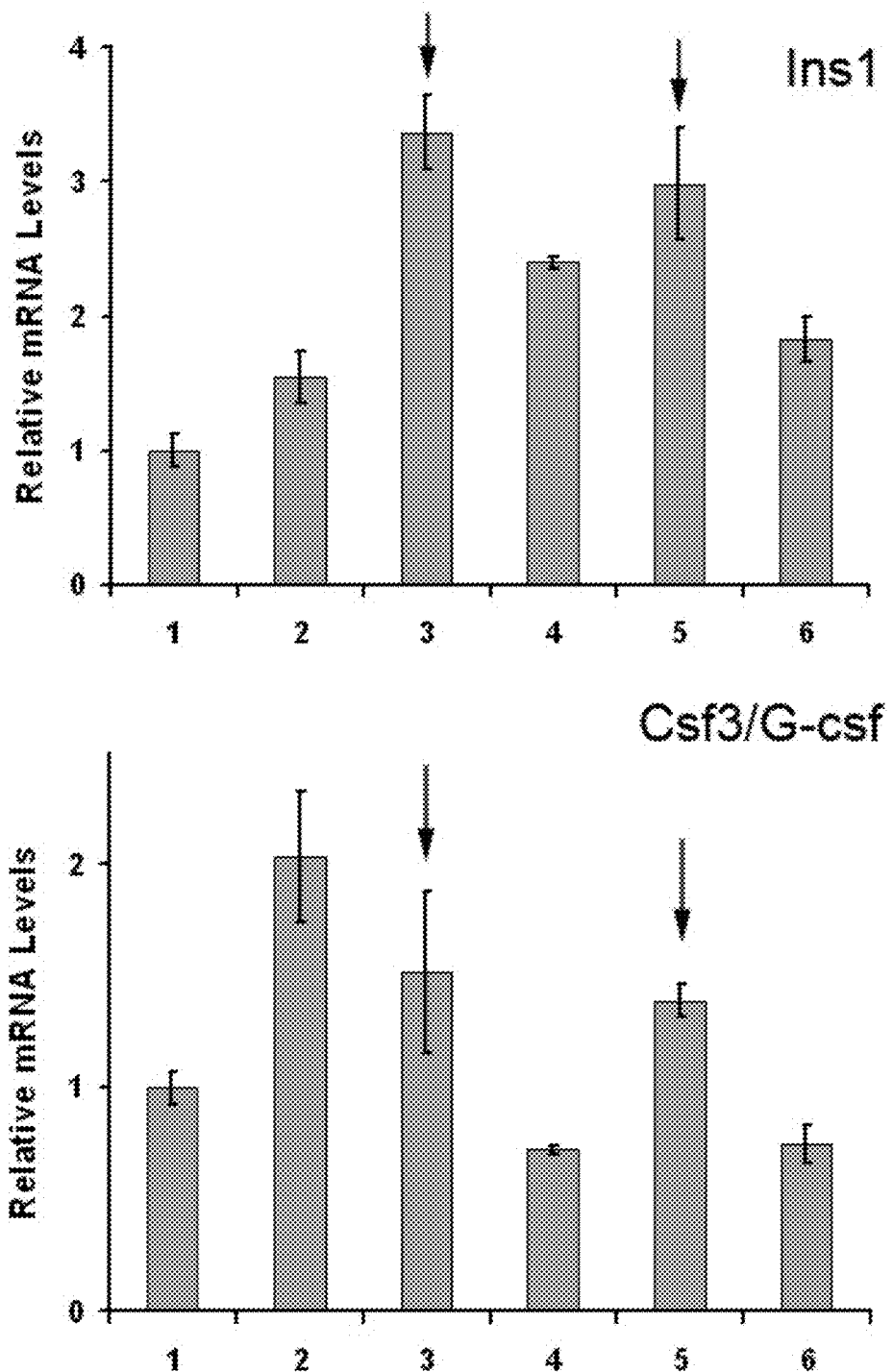
FIG. 17. Real-time PCR gene expression for Ins1 and Csf3/G-csf under media conditions. 3T3-L1 adipocytes were serum-starved for 4 hours prior to a 2-hour recovery period in different media solutions: (1) DMEM, (2) 0.1 μM insulin, (3) 0.1 μM insulin released from ND-insulin by NaOH (pH 10.5), (4) resultant solution from centrifuged ND-insulin in water, (5) ND-insulin treated with NaOH (1 μM total insulin) and (6) NDs with bound insulin (ND-insulin, 1 μM total insulin). Both genes showed increased expression for insulin released by NaOH (3) and ND-insulin treated with NaOH (5), indicating effective insulin release by alkaline conditions while preserving activity. Comparatively, insulin released by water (4) and ND-insulin (6) demonstrated low relative expression for both genes alluding to the sequestration of insulin to the ND surface preventing protein function. Gene expression plot representative of RT-PCR samples. ANOVA: $P<0.01$.
Figure 18:
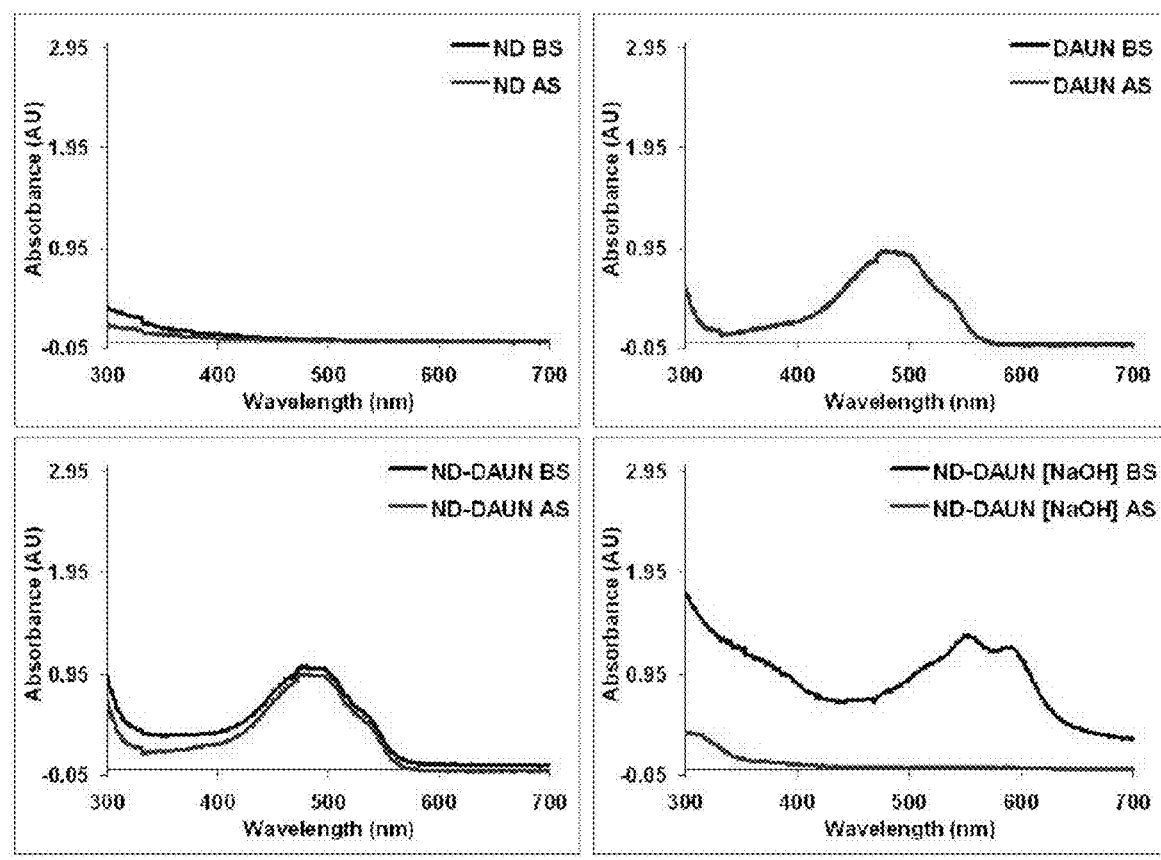
FIG. 18. Spectroscopic analysis of Nanodiamond-Daunorubicin (ND-Daun) adsorption. Absorbance curves were measured before (BS) and after (AS) 15 minute spins (14000 rpm) to pellet any NDs or ND-Daun complexes present in each solution.
Figure 19:
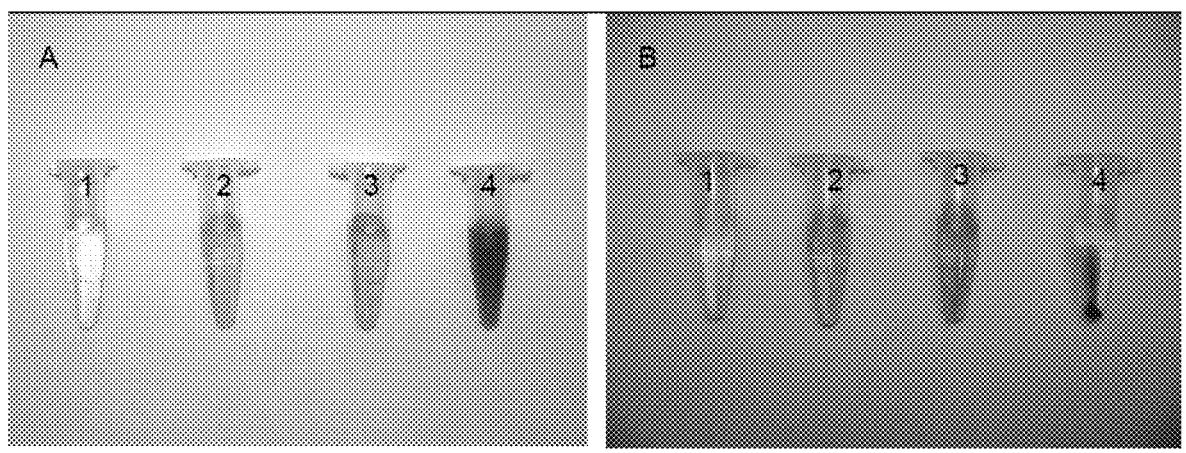
FIG. 19. Comparison of Nanodiamond-Daunorubicin (ND-Daun) adsorption. ND (1), Daun (2), ND-Daun (3), and ND-Daun+NaOH (4) solutions before (A) and after (B) 15 minute centrifugation at 14000 rpm.
Figure 20:
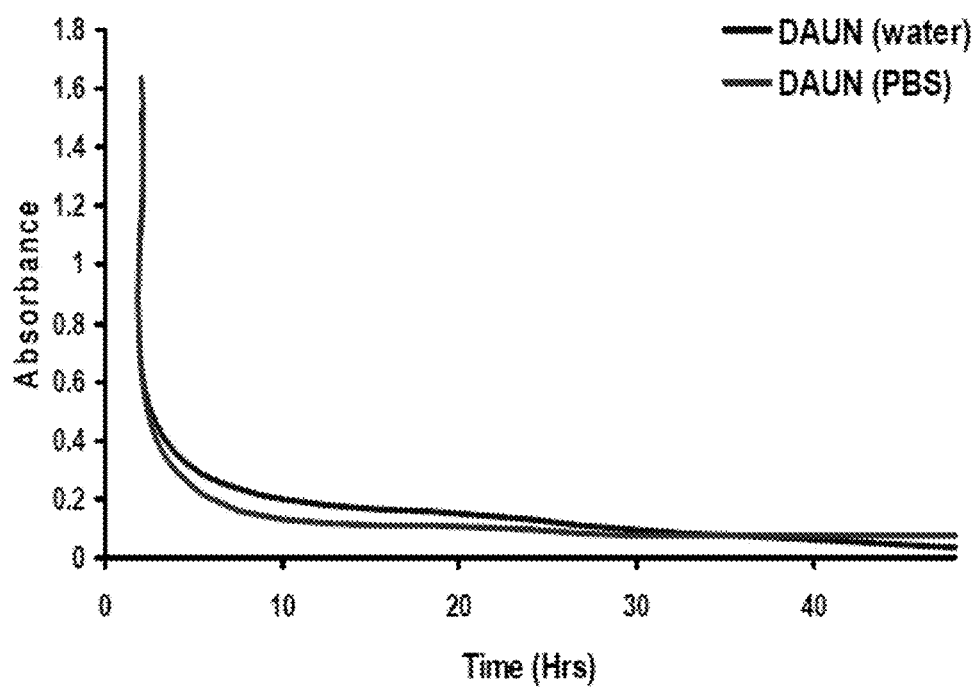
FIG. 20. Desorption of DAUN from Nanodiamond conjugates in water and PBS respectively. Release profiles reveal drug elution is sustained over several hours. Absorbance measured at 485 nm.
Figure 21:
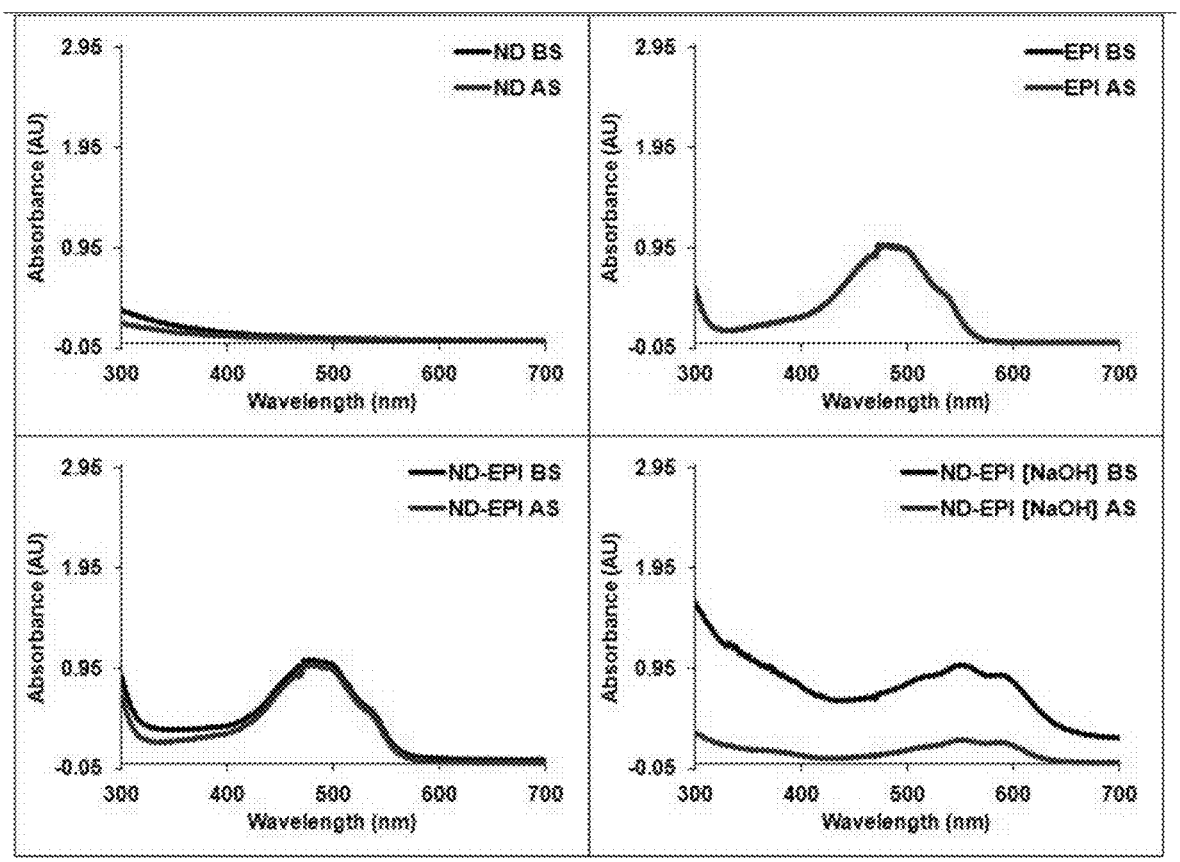
FIG. 21. Spectroscopic analysis of Nanodiamond-Epirubicin (ND-Epi) adsorption. Absorbance curves were measured before (BS) and after (AS) 15 minute spins (14000 rpm) to pellet any NDs or ND-Epi complexes present in each solution.
Figure 22:
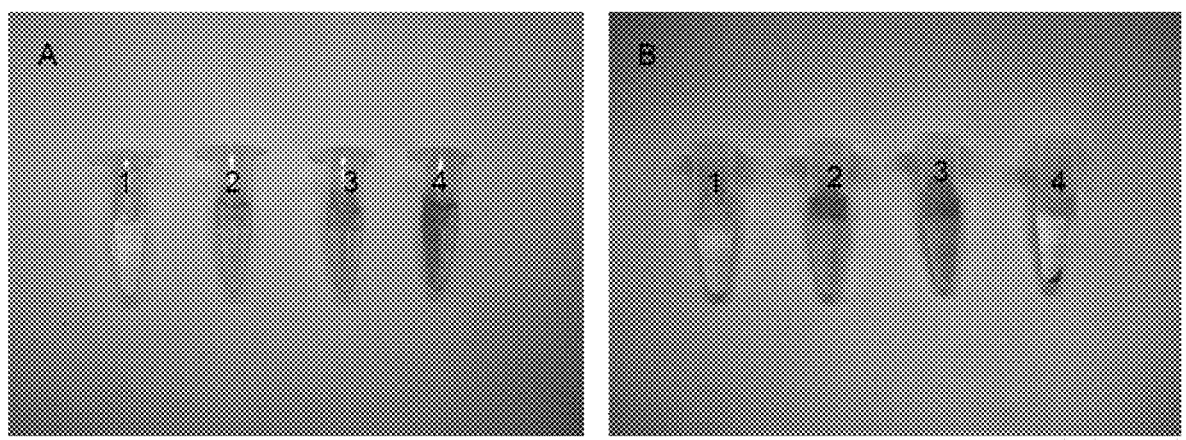
FIG. 22. Comparison of Nanodiamond-Epirubicin (ND-Epi) adsorption. ND (1), Epi (2), ND-Epi (3), and ND-Epi+NaOH (4) solutions before (A) and after (B) 15 minute centrifugation at 14000 rpm.
Figure 23:
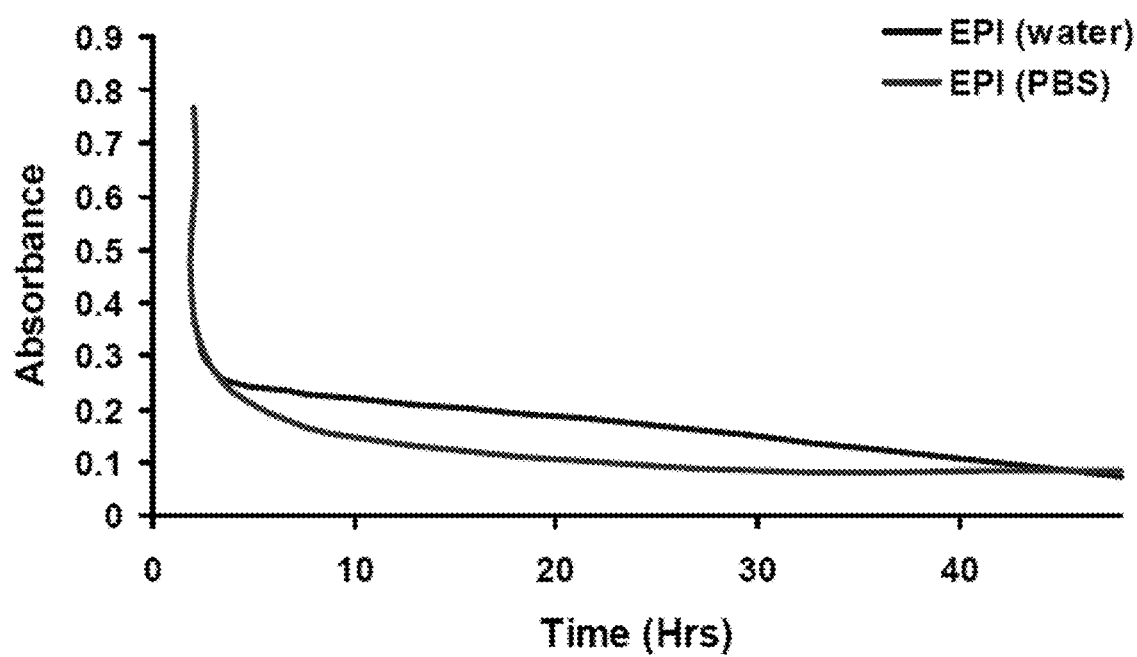
FIG. 23. Desorption of EPI from Nanodiamond conjugates in water and PBS respectively. Release profiles reveal drug elution is sustained over several hours. Absorbance measured at 485 nm.
Figure 24:
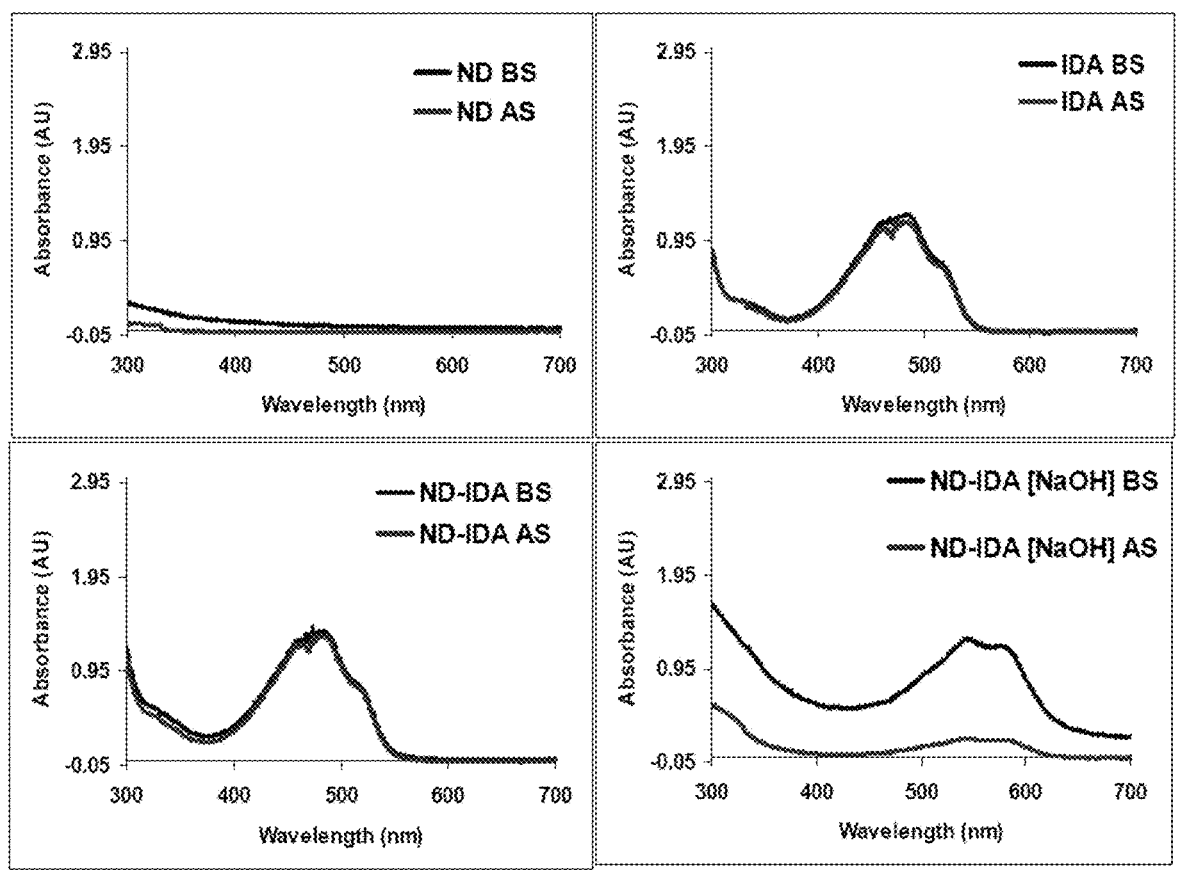
FIG. 24. Spectroscopic analysis of Nandiamond-Idarubicin (ND-IDA) adsorption. Absorbance curves were measured before (BS) and after (AS) two hour spins to pellet any NDs or ND-IDA complexes present in each solution.
Figure 25:
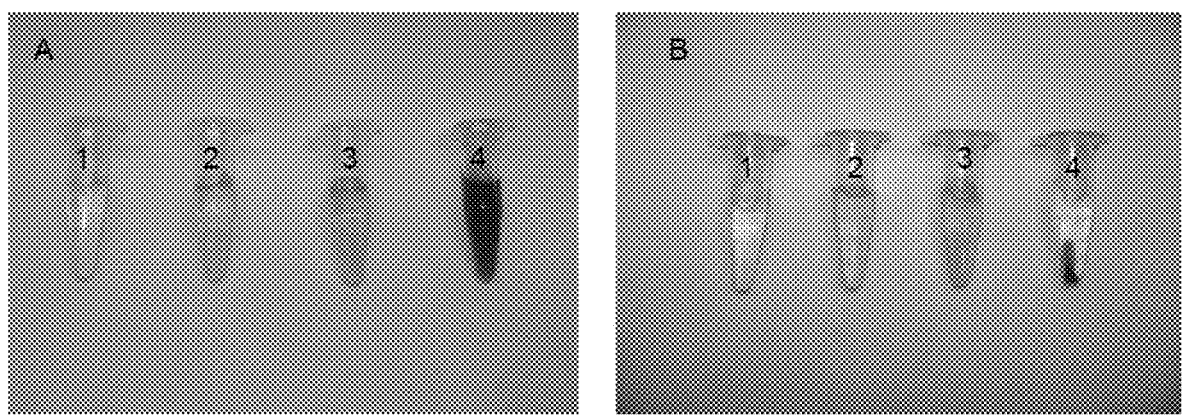
FIG. 25. Comparison of ND-Ida adsorption. ND (1), Ida (2), ND-Ida (3), and ND-Ida+NaOH (4) solutions before (A) and after (B) 15 minute centrifugation at 14000 rpm.
Figure 26:
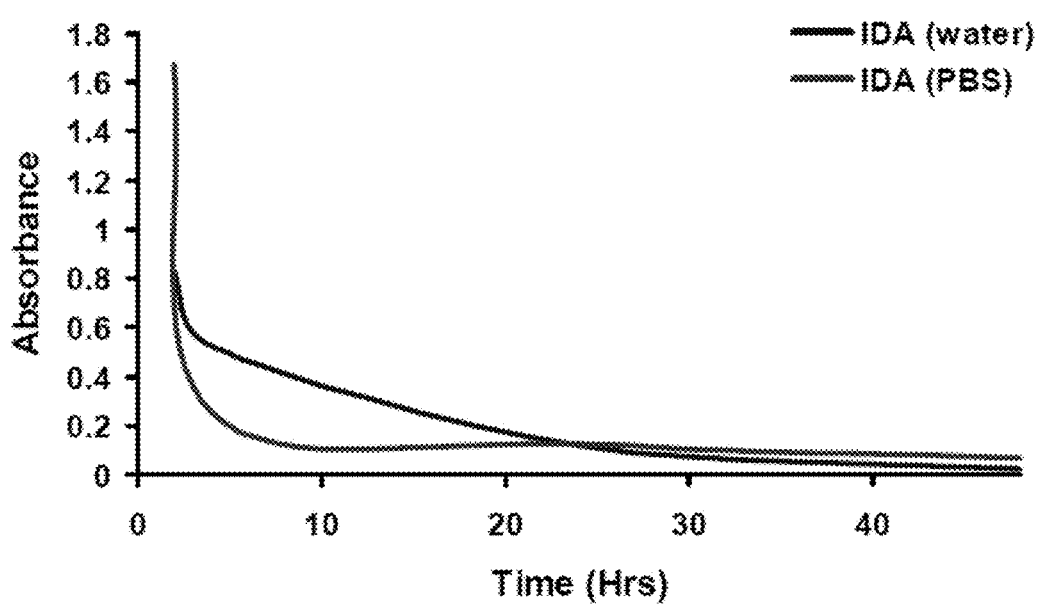
FIG. 26. Desorption of IDA from Nanodiamond conjugates in water and PBS respectively. Release profiles reveal drug elution is sustained over several hours over. Absorbance measured at 485 nm.
Figure 27:
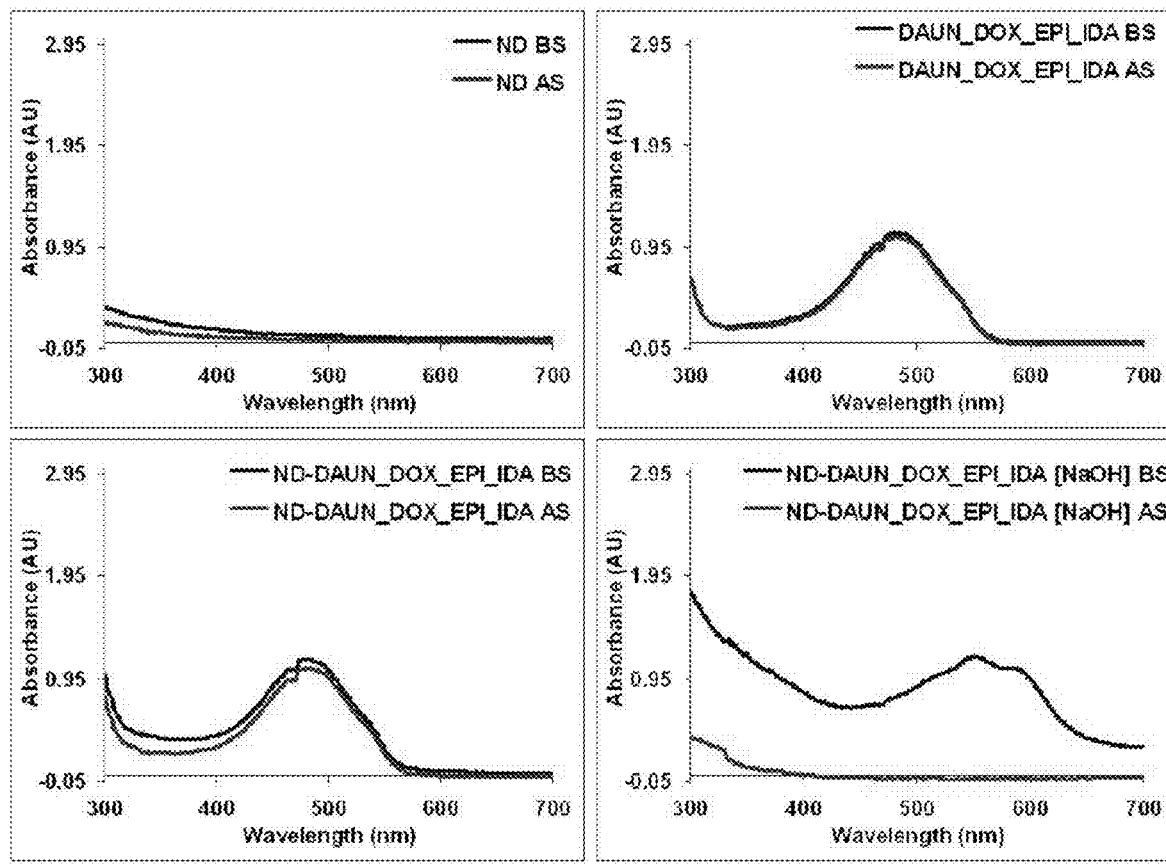
FIG. 27. Spectroscopic analysis of ND-Daun-Dox-Epi-Ida adsorption. Absorbance curves were measured before (BS) and after (AS) 15 minute spins (14000 rpm) to pellet any NDs or ND-Daun+Dox+Epi+Ida complexes present in each solution.
Figure 28:
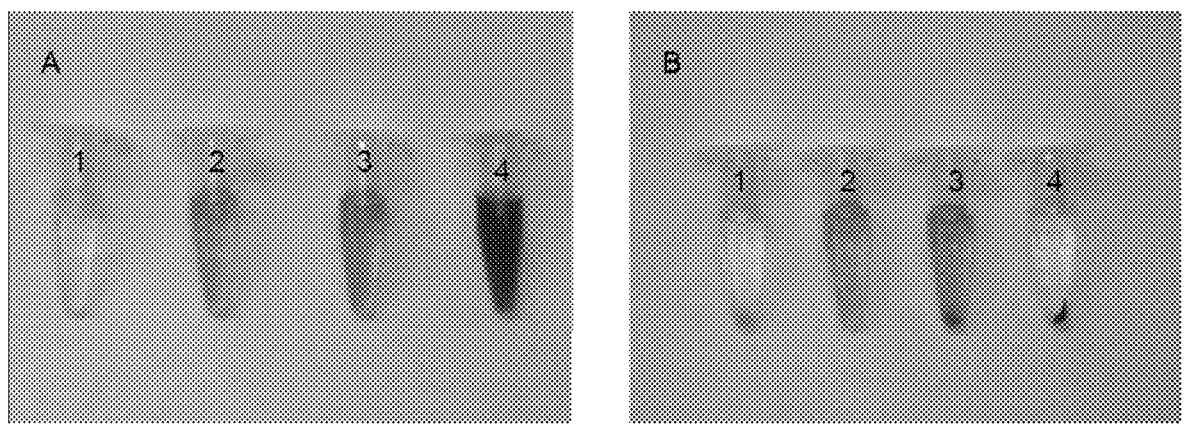
FIG. 28. Comparison of ND-Daun-Dox-Epi-Ida adsorption. ND (1), Daun+Dox+Epi+Ida (2), ND-Daun+Dox+Epi+Ida (3), and ND-Daun+Dox+Epi+Ida+NaOH (4) solutions before (A) and after (B) 15 minute centrifugation at 14000 rpm.
Figure 29:
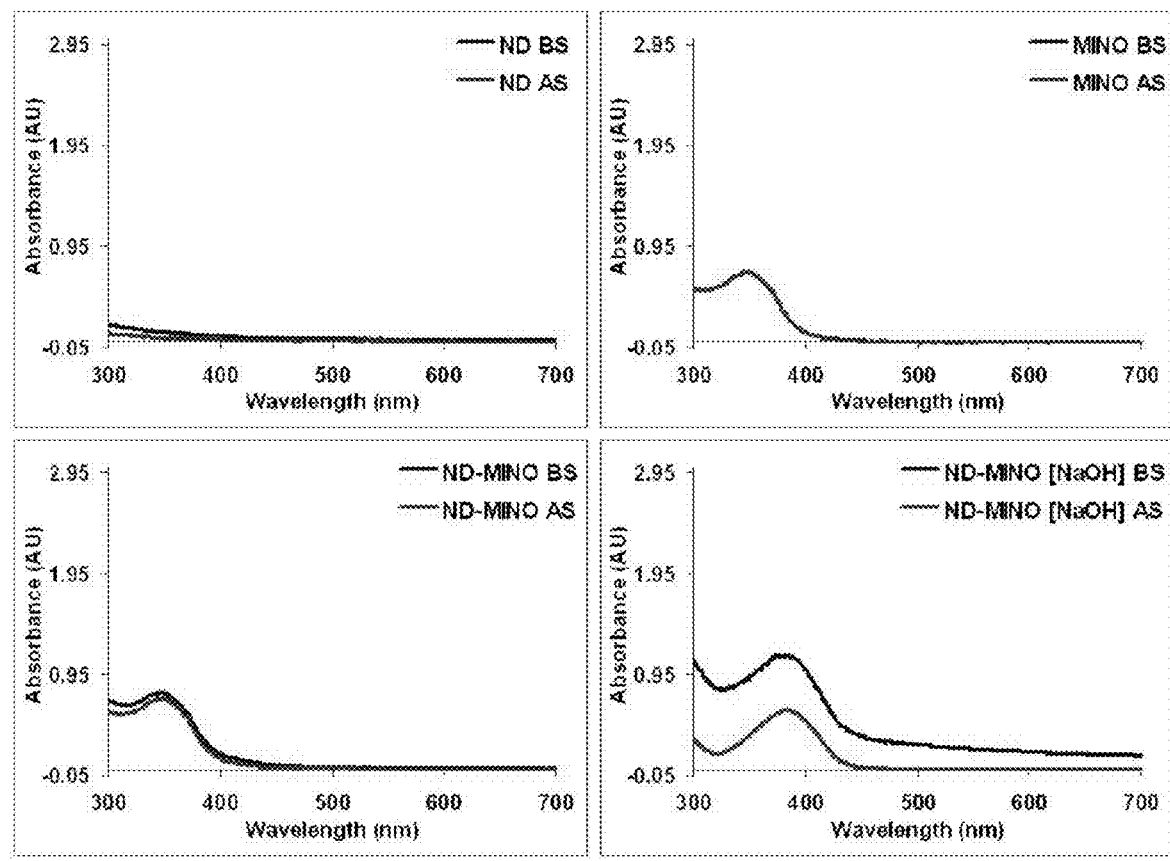
FIG. 29. Spectroscopic analysis of Nanodiamond-Minocycline (ND-Mino) adsorption. Absorbance curves were measured before (BS) and after (AS) 15 minute spins (14000 rpm) to pellet any NDs or ND-Mino complexes present in each solution.
Figure 30:
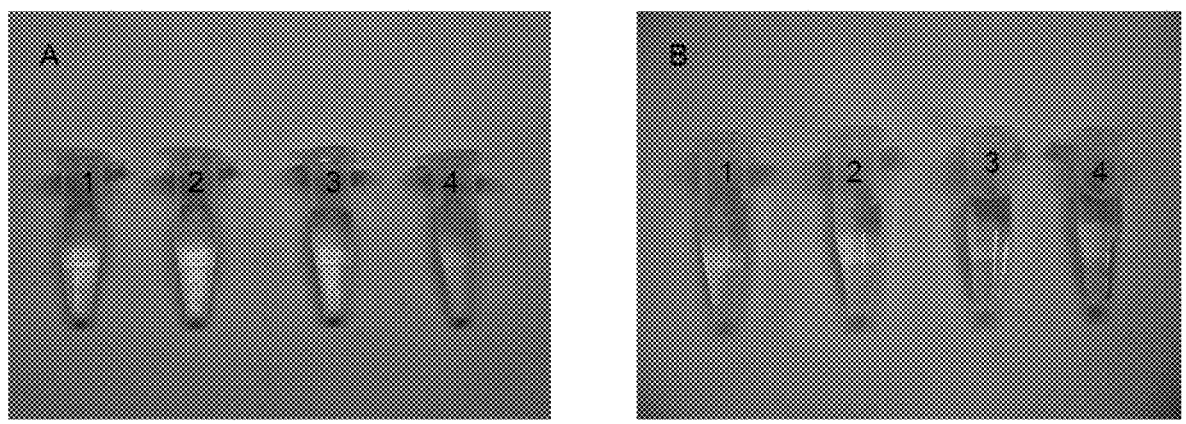
FIG. 30. Comparison of Nanodiamond-Minocycline (ND-Mino) adsorption. ND (1), Mino (2), ND-Mino (3), and ND-Mino+NaOH (4) solutions before (A) and after (B) 15 minute centrifugation at 14000 rpm.
Figure 31:
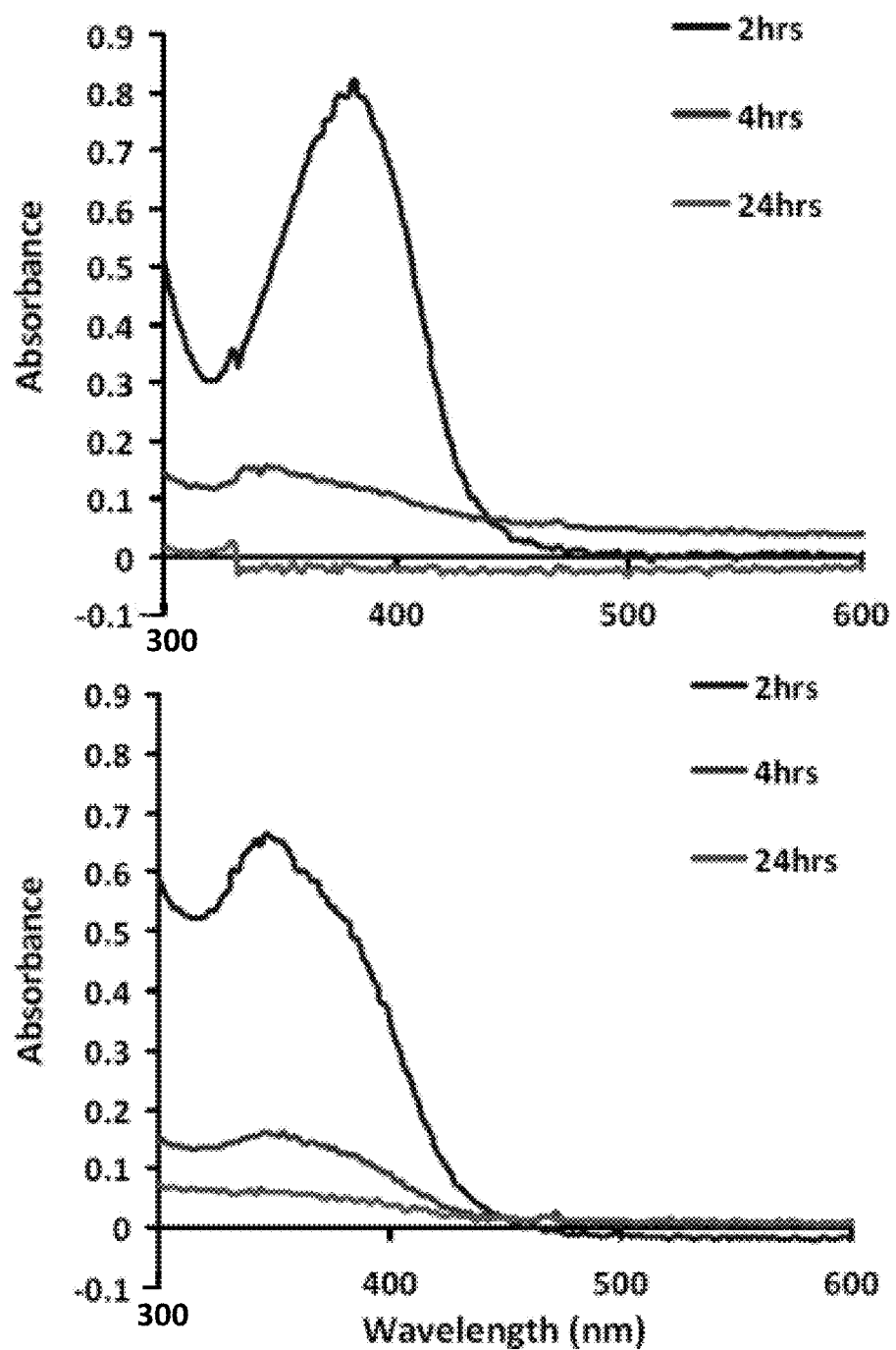
FIG. 31. Desorption of Minocycline from Nanodiamond conjugates. Release profiles performed in water (above) and PBS (below) indicate sustained release over the course of the first few hours.
Figure 32:
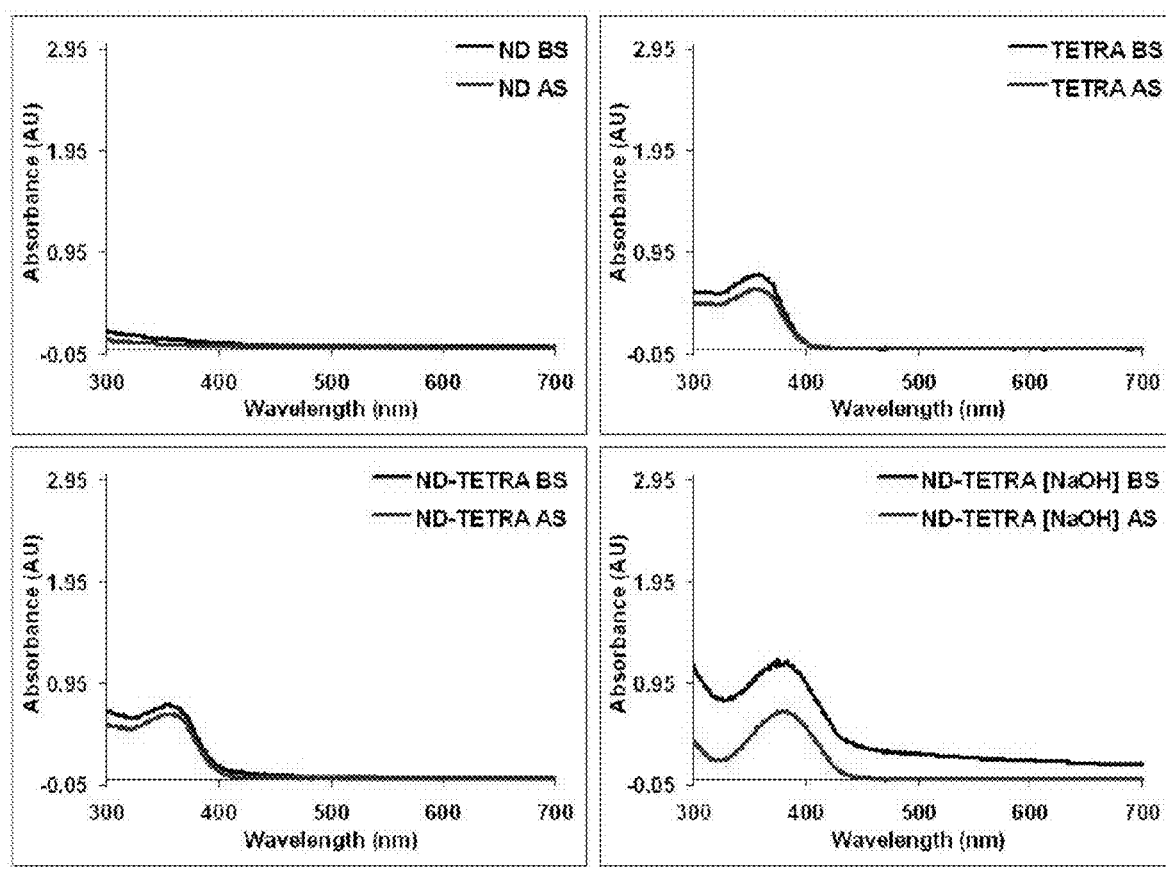
FIG. 32. Spectroscopic analysis of Nanodiamond-Tetracycline (ND-Tetra) adsorption. Absorbance curves were measured before (BS) and after (AS) 15 minute spins (14000 rpm) to pellet any NDs or ND-Tetra complexes present in each solution.
Figure 33:
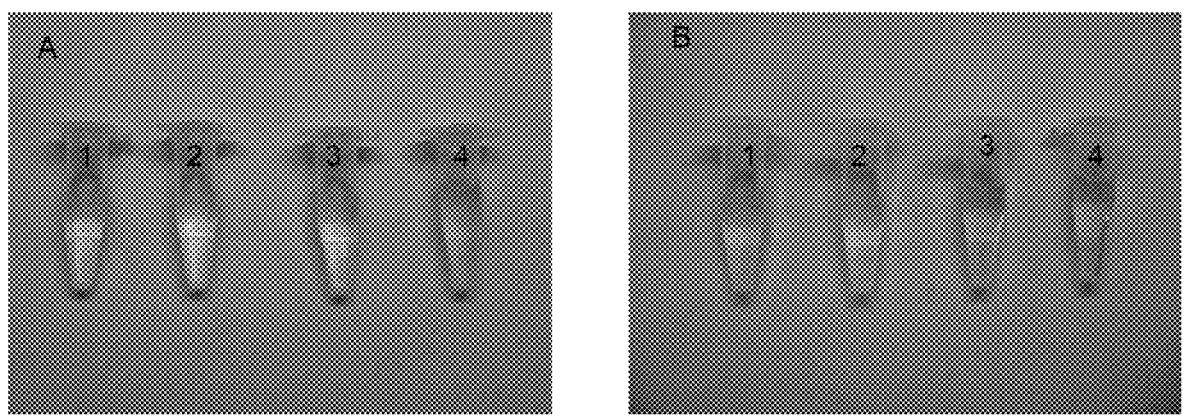
FIG. 33. Comparison of Nanodiamond-Tetracycline (ND-Tetra) adsorption. ND (1), Tetra (2), ND-Tetra (3), and ND-Tetra+NaOH (4) solutions before (A) and after (B) 15 minute centrifugation at 14000 rpm.
Figure 34:
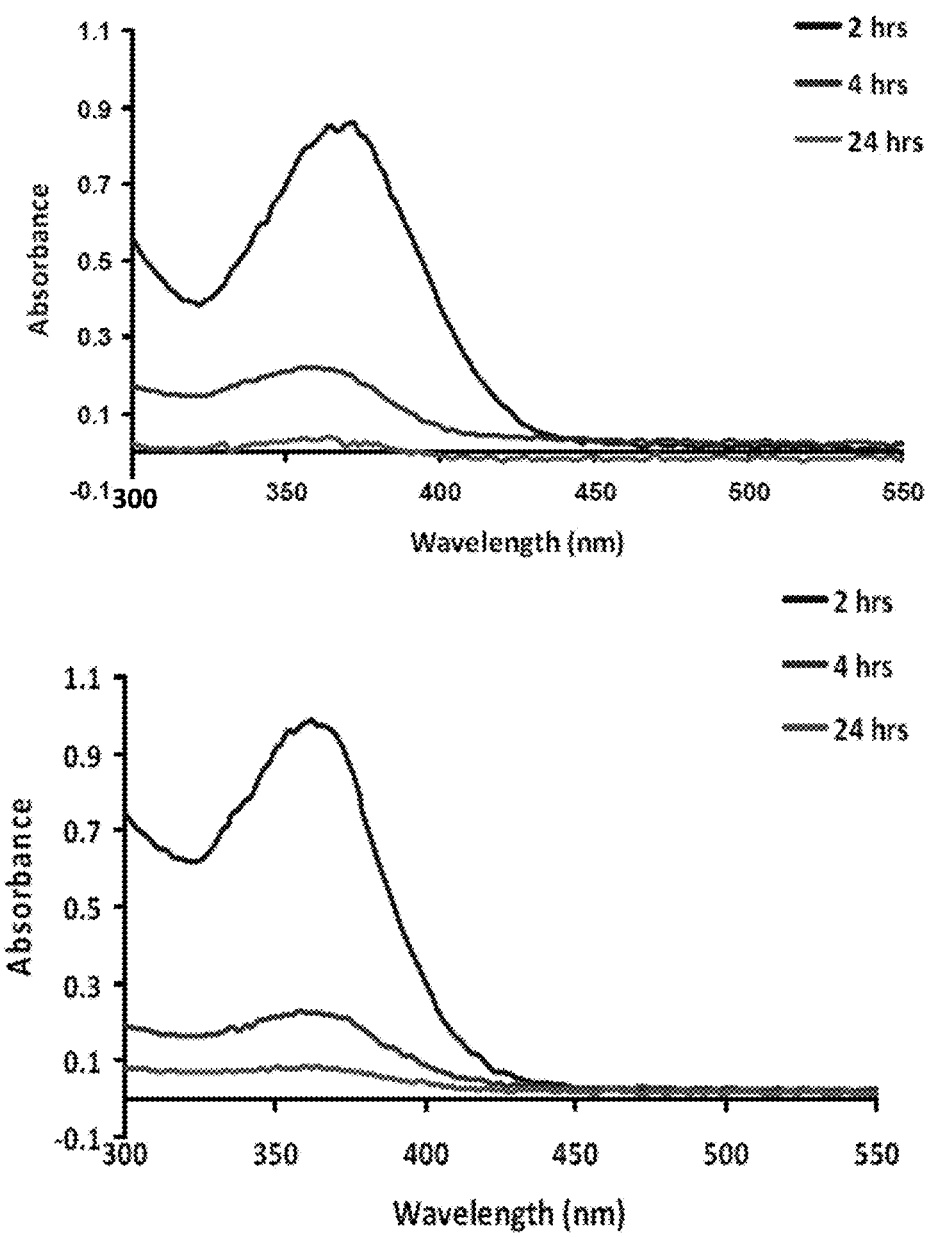
FIG. 34. Desorption of Tetracycline from Nanodiamond conjugates. Release profiles performed in water (above) and PBS (below) indicate sustained release over the course of the first few hours.
Figure 35:
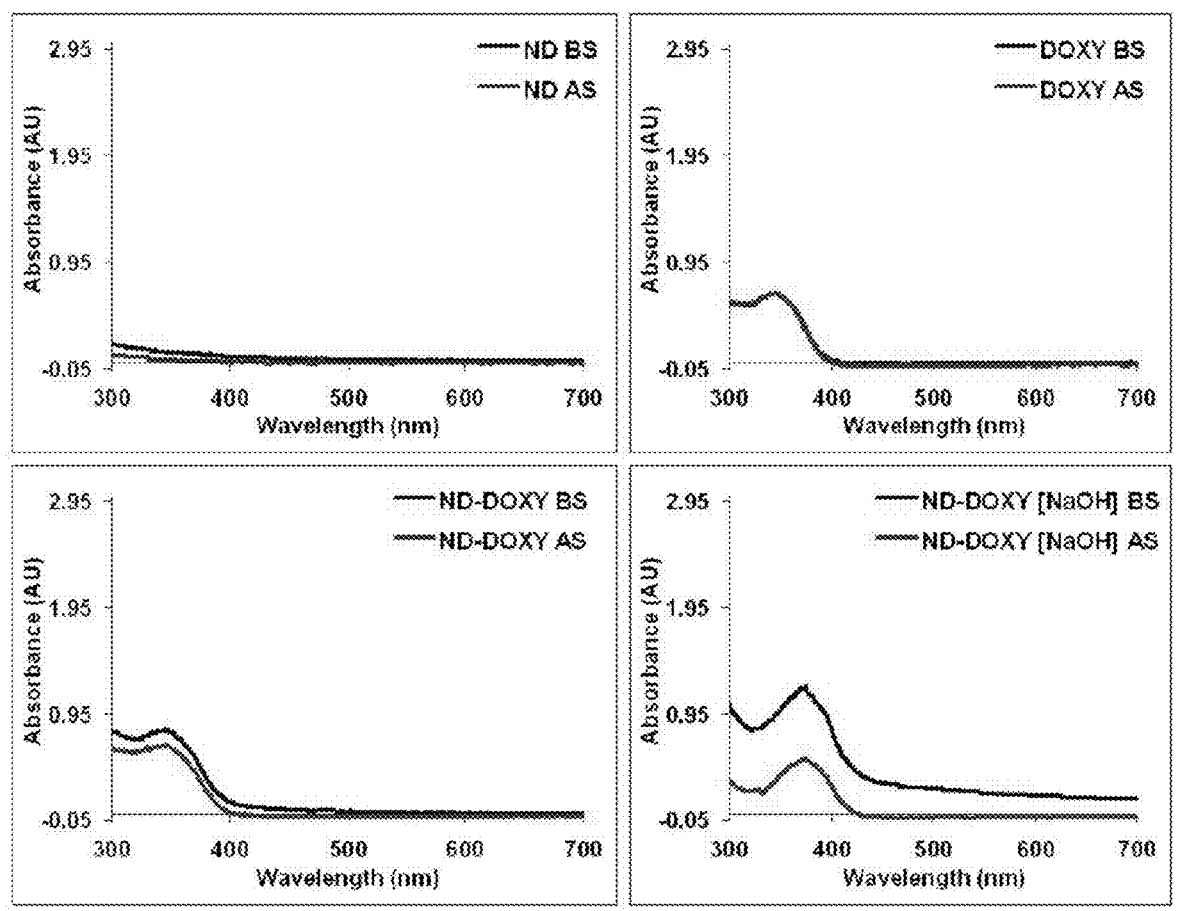
FIG. 35. Spectroscopic analysis of Nanodiamond Doxycycline (ND-Doxy) adsorption. Absorbance curves were measured before (BS) and after (AS) 15 minute spins (14000 rpm) to pellet any NDs or ND-Doxy complexes present in each solution.
Figure 36:
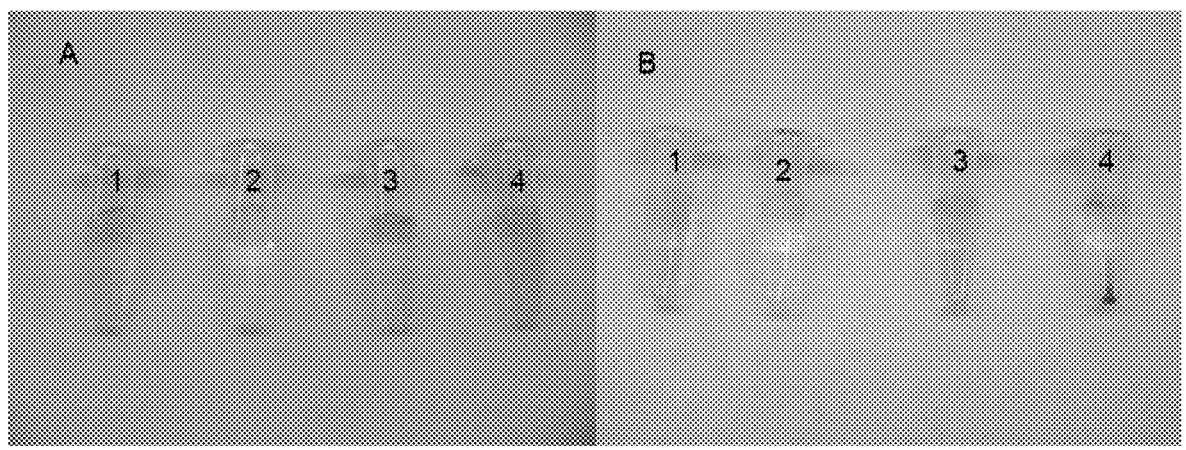
FIG. 36. Comparison of Nanodiamond-Doxycycline (ND-Doxy) adsorption. ND (1), Doxy (2), ND-Doxy (3), and ND-Doxy+NaOH (4) solutions before (A) and after (B) 15 minute centrifugation at 14000 rpm.
Figure 37:
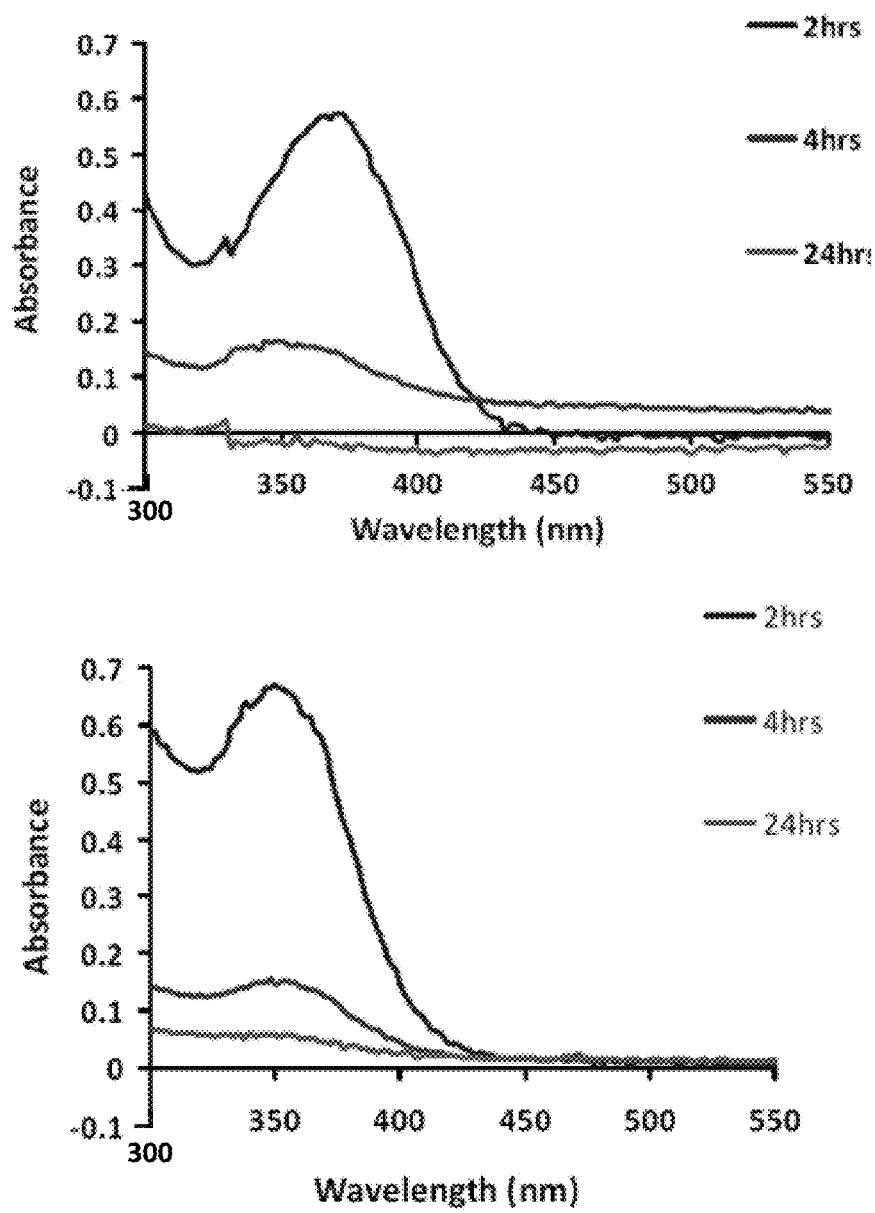
FIG. 37. Desorption of Doxycycline from Nanodiamond conjugates. Release profiles performed in water (above) and PBS (below) indicate sustained release over the course of the first few hours.
Figure 38:
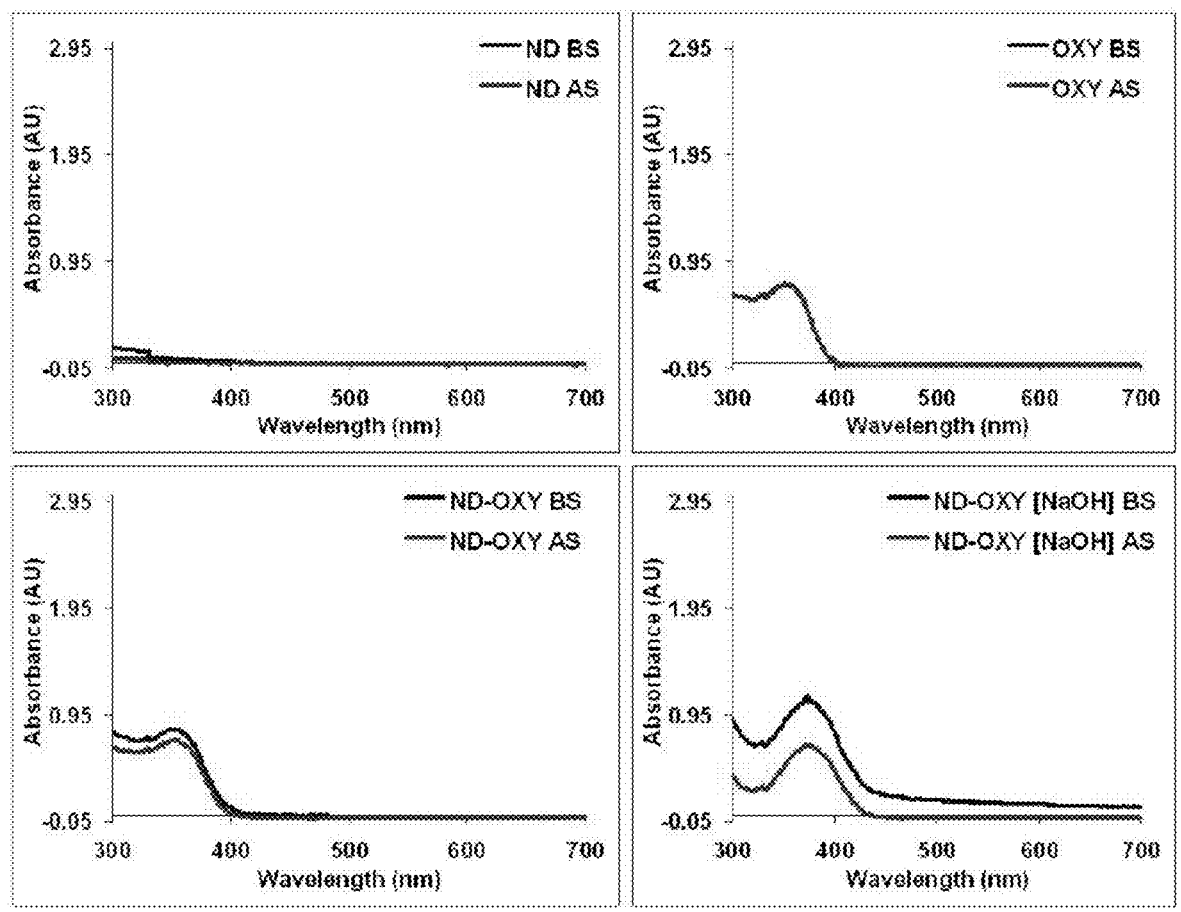
FIG. 38. Spectroscopic analysis of Nanodiamond-Oxytetracycline (ND-Oxy) adsorption. Absorbance curves were measured before (BS) and after (AS) 15 minute spins (14000 rpm) to pellet any NDs or ND-Oxy complexes present in each solution.
Figure 39:
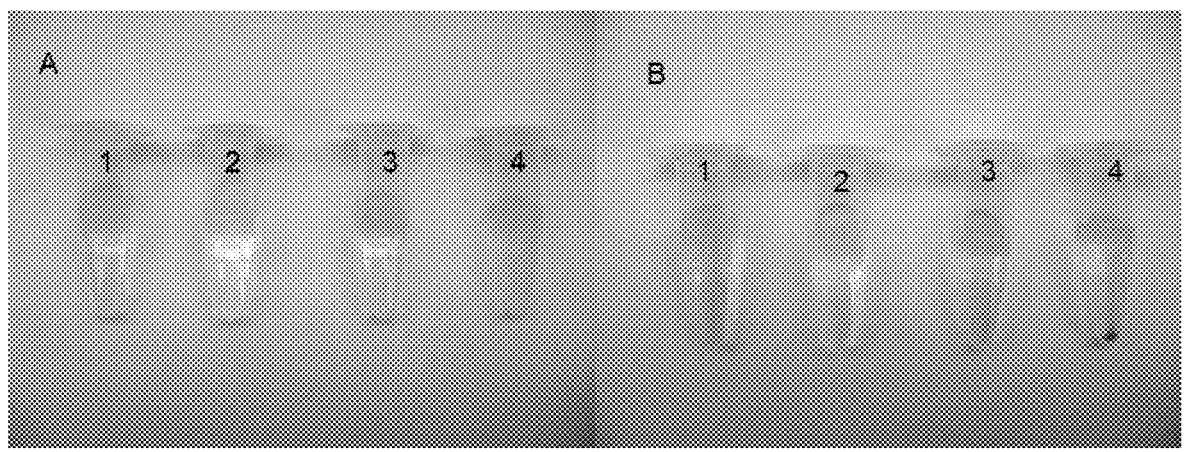
FIG. 39. Comparison of Nanodiamond-Oxytetracycline (ND-Oxy) adsorption. ND (1), Oxy (2), ND-Oxy (3), and ND-Oxy+NaOH (4) solutions before (A) and after (B) 15 minute centrifugation at 14000 rpm.

Pre-adipocyte differentiation yielded adipocytes by day 10 post-induction based on observations of morphology change and lipid vesicle formation in >90% of cells (FIG. 16). Pre-adipocytes (a) differ from adipocytes (b) by the clearly visible lipid vesicles. The effect of released insulin on adipocytes was quantified by RT-PCR for the genes Insulin 1 (Ins1) and Granulocyte colony-stimulating factor (Csf3/G-csf), and normalized to the housekeeping gene Ribosomal protein L32 (Rpl32). The relative expression of Ins1 in response to varying media solutions is shown (FIG. 17-*a*). Compared to DMEM (1), insulin released by NaOH (3) and ND-insulin treated with NaOH (5) showed the highest relative expressions, indicating these conditions had the greatest effect on Ins1. Insulin released by water (4) and ND-insulin (6) resulted in moderate expression levels compared to the insulin-only condition (2) showing the lowest expression of Ins1. Csf3/G-csf relative expression is displayed in FIG. 17-*b* and shows a similar trend as with Ins1 in that both insulin released by NaOH (3) and ND-insulin treated with NaOH (5) demonstrate high expression levels, while insulin released by water (4) and NDs with bound insulin (6) are significantly lower. The effect of 0.1 µM insulin on Csf3/G-csf, however, was comparably higher than that of Ins1. The ANOVA statistical test gave $P<0.01$, indicating a significant difference among sample groups.

Physical Adsorption

Conditions during ND synthesis result in a heavily functionalized hydrophilic carbon surface of hydroxyl and carboxyl groups, which can lead to a characteristic surface charge in aqueous solutions [8, 28, 29]. Such functional groups present favorable conditions for the physical adsorption of proteins via electrostatic attraction between anionic end groups (—COO$^-$) and protonated amino groups (—NH$_3^+$) of polypeptides. In addition to charge-charge interactions, hydrogen bonds can form between —NH$_3^+$ and —COO$^-$ or other CO-containing surface groups, with H-bond binding energies between 10-30 kcal/mol [33, 34, 37]. Charged amino acid residues on the exterior of the insulin molecule contribute to its hydrophilicity and can be attracted to the ND surface. Although the isoelectric point of insulin is approximately 5.6 [38], indicating a slightly negative net charge at neutral pH, the electrostatic interactions and H-bonding between ND functional groups and amine biomolecules may lead to attractive interactions. FIG. 9 illustrates, hypothetically, this concept of insulin adsorption to NDs in a neutral environment.

Figure 11:
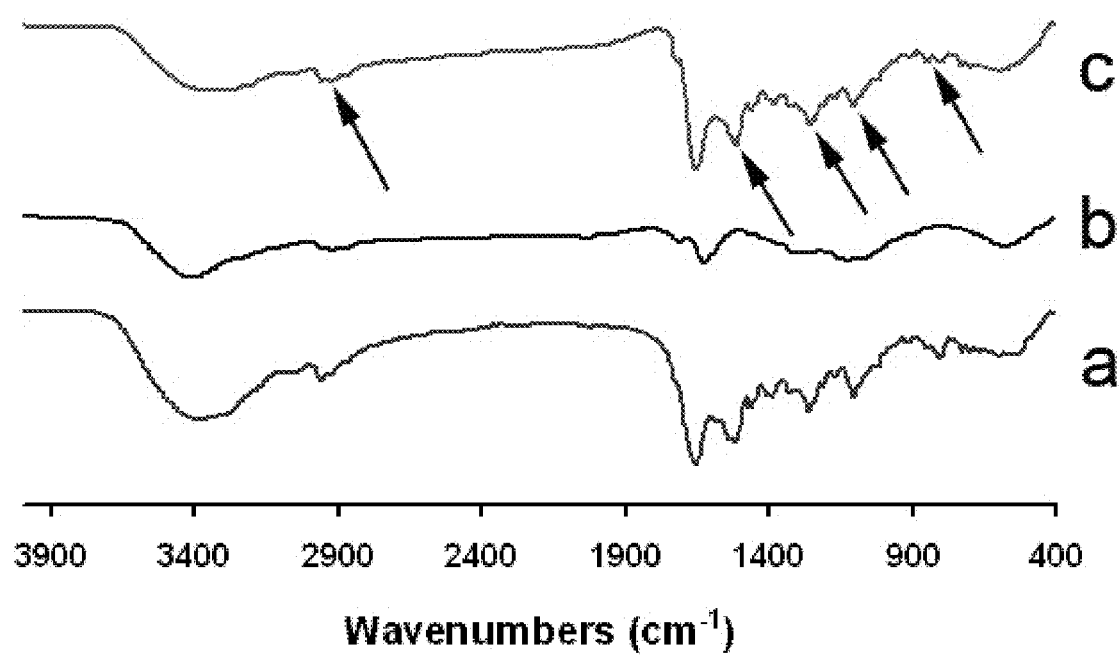
FIG. 11. Infrared spectra of (a) FITC insulin, (b) bare NDs and (c) ND-insulin complex. The arrows indicate the characteristic spectra of insulin present on the ND-insulin spectra, as compared to the bare-ND spectra. Image (c) suggests the formation of ND-insulin complexes as noted by the differential spectra. The data alludes to the non-covalent adsorption of insulin to NDs.

TEM imagery shows NDs after immersion in aqueous insulin (FIG. 10-*b*) with a visible layer of material coating the ND surface, as compared to bare NDs (a). Since the addition of insulin (b) is the only discriminating factor, it lends precedence to the material layer (thickness 5-10 nm) being identified as adsorbed insulin. The ND clusters seen in FIG. 10 boast very high surface area allowing for substantial insulin adsorption to functional groups on the NDs. In fact, ND characterization has previously demonstrated a remarkable surface area of 450 m²/g [9]. TEM imaging provides visual recognition of protein binding, and adsorption can be quantified by FT-IR spectroscopy. Insulin adsorption to NDs is validated by FT-IR characterization of insulin, bare NDs and NDs with bound insulin (FIG. 11). The characteristic spectra of insulin (a) is distinctly seen in the spectra of NDs with bound insulin (c), quantifiable results that otherwise would not be obtained from NDs without adsorbed insulin (b). TEM and FT-IR provide additional evidence of insulin adsorption to the ND surface.

Further substantiation of the ND-insulin complex is given by UV/vis analysis. Adsorption tests revealed a 5:1 ratio of NDs to FITC insulin at optimal binding capacity (absence of excess insulin in resultant solution), demonstrating 89.8±8.5% adsorption. Absence of measurable absorbance of the centrifuged ND-insulin sample (FIG. 13-a) signifies considerable FITC insulin adsorption to NDs. The absorbance difference at 485 nm between initial and centrifuged ND-insulin samples is attributed to the molecular weight of NDs and settling of NDs with bound insulin during centrifugation, leaving trivial amounts of residual insulin in solution. A slight difference between initial and centrifuged insulin control samples is used to normalize adsorption values since the molecular weight of insulin compared to the aqueous solution allows for the separation of components. FIG. 5-a reveals altered absorbance spectra of ND-insulin when compared to that of insulin, with absorbance peaks of insulin and ND-insulin shifting from 485 nm to 505 nm. This peak shift is possibly due to a change in optical properties of the FITC molecule when FITC-labeled insulin adsorbs to NDs, indicating a possible conformational change in protein structure often observed in protein adsorption [39].

Similar results were obtained from standard bovine insulin adsorption tests with an optimal ND-to-insulin binding ratio of 4:1. A higher adsorption ratio for standard bovine insulin is expected given that the molecular weight of insulin as compared to that of FITC-labeled insulin. FIG. 13-b depicts BCA protein assay absorbance revealing contrasting peaks for initial and centrifuged ND-insulin samples associating to a substantial 79.8±4.3% insulin adsorption.

Insulin adsorption tests involving FITC-labeled and standard insulin are consistent with previous investigation verifying protein-ND binding [34] and exhibit exceptional adsorption capabilities, with approximately 80% of insulin binding to the ND surface at optimal ND-insulin ratios. The protein loading capacity of NDs as demonstrated by the adsorption tests imply a relatively efficient drug-loading process where the majority of available protein is adsorbed to the ND surface. The simple method of physical adsorption in aqueous solutions is ideal for drug delivery preparation methods by eliminating complex conjugation protocols that can affect the properties of the drug or substrate.

The physical interaction between NDs and insulin was also characterized via dynamic light scattering (Table 1).

TABLE 1

|  | pH | Average Size (μm) | PDI |
| --- | --- | --- | --- |
| Nanodiamond | 7 | 1.67 ± 0.64 | 0.41 ± 0.084 |
|  | 10.5 | 1.63 ± 0.66 | 0.30 ± 0.13 |
| Insulin | 7 | 1.59 ± 0.038 | 0.97 ± 0.046 |
|  | 10.5 | 2.28 ± 0.66 | 0.99 ± 0.011 |

TABLE 1-continued

|  | pH | Average Size (μm) | PDI |
| --- | --- | --- | --- |
| Nanodiamond- | 7 | 1.69 ± 0.37 | 0.23 ± 0.18 |
| Insulin | 10.5 | 1.05 ± 0.081 | 0.40 ± 0.12 |

Table 1 shows a DLS analysis of hydrodynamic nanoparticle cluster size and the associated polydispersity index (PDI) at pH7 and 10.5. NDs exhibited similar size and PDI at both pH conditions, while insulin at pH 10.5 tended to form larger particles with an increased PDI. Upon formation of the ND-insulin complex the PDI decreased, suggesting NDs mediate a relatively even distribution size of clusters.

NDs formed clusters of similar hydrodynamic size and distribution at pH 7 and 10.5 while insulin aggregated into larger sizes within alkaline solutions. Upon complexing with NDs, the polydispersity index is not only reduced, but the zeta potential of the clusters also altered to a negative value (FIG. 12). The reduction of PDI as seen with the formation of ND-insulin complexes, compared to that of insulin, indicates a ND-mediated development of a more uniform nanomaterial-protein complex. NDs originally maintained a slightly positive zeta potential within alkaline solutions while insulin inherently possessed a negative zeta potential that further decreased in alkaline solutions. This zeta potential was retained upon introduction with NDs, implying insulin adherence onto the ND surface. This result is further verified since the cluster's zeta potential at pH 10.5 lies within a narrow confined range of values. The clear difference in zeta potential between bare NDs and ND-insulin suggests an interaction between NDs and insulin.

pH-Mediated Desorption

Release of insulin from the ND-insulin complex was observed in alkaline sodium hydroxide solutions and can be explained by a change in charge characteristics affected by pH modification. Insulin in aqueous environments at a pH above the isoelectric point may carry a negative net surface charge owing to the charge alteration of the functional end groups. Subsequently, the negative charge can become stronger with increased alkalinity and affect charge interactions with other species. Thus, the effect of pH on desorption is rather straightforward. Insulin molecules bound to charged functional groups on the ND surface via electrostatic interactions and hydrogen bonding will begin to display altered charge characteristics as the aqueous environment shifts from neutral to alkaline, and therefore release from the NDs by electrostatic repulsion.

The amount of desorbed insulin seems to be proportional to the pH of solution, showing increased insulin release in alkaline solutions (FIG. 13c-d). Absorbance spectra of FITC-labeled insulin desorption (FIG. 13-c) represent an increase in desorption as the pH shifts from 8.90 to 11.53, and a similar pattern is expressed in FIG. 13-d with standard insulin. These results are consistent with the pH-dependent desorption premise mentioned previously. The 31.3±1.6% desorption of standard insulin in NaOH demonstrates insulin is capable of being adsorbed and subsequently released from the ND surface into an aqueous medium.

Many practical applications necessitate the release of a drug over time, and in order to quantify the time-release of insulin a 5-day desorption test was conducted with NDs with bound insulin in both NaOH and water. The disproportion between the two release curves in FIG. 14 exemplifies the difference in desorption ability of alkaline and neutral solutions. Alkaline-mediated desorption reached 45.8±3.8% by day 5 compared to only 2.2±1.2% in water. The bulk of desorption occurred by day 1 of the test, suggesting a burst release of insulin from NDs. Day 2, however, did produce a moderate insulin release. The time-dependency of insulin release enables the ND-insulin complex to slow release insulin upon exposure to alkaline environments.

Preservation of Protein Function

Results discussed in the previous section establish a basis for pH-mediated insulin desorption, yet practical use of such a system relies on the retained function of the drug upon release from the ND surface. The data obtained from MTT viability assays and RT-PCR suggest insulin function is indeed preserved subsequent to desorption as noted by cell viability and gene expression. Furthermore, insulin sequestered on the ND surface seems to remain inactive to cellular pathways despite the presence of the ND-insulin complex.

Cell viability data (FIG. 15) reveal an increase in cellular recovery with insulin released from NDs by NaOH and ND-insulin complex treated with NaOH, the latter comprised of NDs and desorbed insulin in media solution. The increased viability levels of cells in these two media conditions, as compared to DMEM baseline, signify the released insulin is activating cellular recovery pathways following the starvation period. Also, viability of ND-insulin treated with NaOH indicates cellular recovery occurs in the presence of the released insulin and the subsequent NaOH-treated NDs which may or may not result in bare ND surfaces. Previous investigation implementing serum-starvation and insulin recovery on RAW 264.7 macrophages [40] is consistent with the acquired MTT data showing insulin-mediated recovery.

Insulin released by water and ND-insulin, in contrast, yielded low viability levels, implying little or no insulin release in the neutral environment. The ND-insulin complex seems to prevent the adsorbed insulin from affecting cellular pathways even with insulin exposed on the ND surface. Proteins are often known to undergo a conformational change when adsorbed to a surface [39] leading to altered physical properties, and a change in the structure of insulin on the ND surface may prevent activation of cellular pathways. Effective isolation of insulin from a soluble environment until mediation by alkalinity is key to targeted insulin delivery of this system.

Gene expression from RT-PCR closely correlated with results from MTT viability assays. FIG. 17 shows relative expression of genes Ins1 and Csf3/G-csf, which are upregulated by insulin stimulation of adipocyte cells [35]. Expression levels for samples containing insulin released by NaOH and ND-insulin treated with NaOH increased for each gene, demonstrating the effectiveness of insulin after desorption from the ND surface. Absence of active insulin does not increase expression levels as noted by the DMEM baseline. Similar to the MTT results, insulin released by water and ND-insulin show reduced expression levels for each gene, indicating insufficient response to or reduced insulin concentration so as to activate cellular pathways. This suggests protein activity is retained for insulin desorbed from NDs as determined by genetic expression attributed to insulin stimulation. Additionally, adsorbed insulin, despite being bound to the ND surface, does not increase cell viability or gene expression. In this manner the ND-insulin complex presents a unique approach for targeted insulin (or other protein) delivery in alkaline environments while remaining stable in neutral solutions.

These findings also indicate that insulin adsorption and elution from NDs is pH-dependent, an observation that can be scaled for therapeutic purposes. While the present invention is not limited to any particular mechanism and an understanding of the mechanism is not necessary to practice the present invention, insulin desorption is shown to increase in alkaline environments possibly by action of a change in surface charge of the protein, thereby decreasing the propensity of ND-to-insulin attraction. Exploiting this pH-mediated desorption mechanism may provide unique advantages for enhanced drug delivery methods. It is well understood that insulin accelerates wound healing by acting as a growth hormone [41-45]. Furthermore, previous investigations have confirmed an increase in alkalinity of wound tissue due to bacterial colonization, sometimes as high as pH 10.5 [46, 47]. Considering these two observations the ND-insulin complex may be used as a useful therapeutic drug delivery system for the treatment of wound healing. Administration of NDs with adsorbed insulin may be able to shorten the healing process and decrease the incidence of infection by releasing insulin in alkaline wound areas. Systemic activation of insulin would be limited as the release of insulin would occur at the site of injury. As such, the present invention provides for a targeted insulin-release mechanism directed at injury wounds as a regenerative therapy using NDs as an insulin vehicle.

Experiments conducted during development of embodiments of the present invention demonstrated the efficient, non-covalent adsorption of insulin to NDs by means of simple physical adsorption and has investigated the pH-dependency of protein desorption. Exposure of the ND-insulin complex to alkaline environments mediates the interaction between NDs and insulin resulting in protein release. Imaging methods and adsorption/desorption assays reveal effective binding of insulin to NDs and significant insulin release under alkaline conditions. MTT and RT-PCR analysis indicate preserved function following desorption, while adsorbed insulin remained largely inactive.

Example 3

Nanodiamond-Drug Binding Assays

Nanodiamond-drug binding assays were performed during development of embodiments of the present invention to confirm the potent interaction between a broad array of anthracycline and tetracycline compounds. The binding efficiency of therapeutics such as daunorubicin, idarubicin, and others were analyzed using UV-vis spectrophotometry, as well as centrifugation assays (SEE FIGS. 18-39). In all cases, nanodiamond-drug interactions were capable of comprehensively pelleting the therapeutics (SEE FIGS. 19, 22, 25, 28, 30, 33, 36, and 39), indicating potent adsorption which was further confirmed via spectrophotometric analysis SEE FIGS. 17-18, 20-21, 23-24, 26-27, 29, SEE FIGS. 17-18, 20-21, 23-24, 26-27, 29, 1-32, 34-35, and 37-38).

Example 4

Compositions and Methods for the Preparation and Characterization of Amine-Functionalized Parylene Substrate Preparation. Plain glass slides were sterilized in 70% ethanol and pre-treated with A-174 Silane (SCS COATINGS, Indianapolis, Ind.) adhesion promoter according to manufacturer's protocol. Approximately 20 grams of Parylene A (UNIGLOBE KISCO, White Plains, N.Y.) was loaded into a Parylene deposition system (PDS) 2010 LAB-COTER® 2 (SCS COATINGS.) The deposition took place under previously indicated conditions (Kramer et al. 1984, 22, 475, Yang et al. Journal of Crystal Growth 1998, 183, 385, herein incorporated by reference in their entireties). Application of drug to the base layer of Parylene A was accomplished via desiccation of 100 μg dexmnethasone (SIGMA ALDRICH, St Louis, Mo.), or 25 μg doxorubicin (U.S. PHARMACOPIA, Rockville, Md.) under a laminar flow hood. A second layer of 150 mg of Parylene A was deposited over the drug films to produce the eluting layer.

Cell Culture Conditions. Macrophage cell line RAW 264.7 (AICC Manassas, Va.) cells were grown in DMEM media (MEDIATECH Inc, Hemdon, Va.) supplemented with 10% FBS (AICC) and 1% Penicillin/Streptomycin (LONZA, Walkersville, Md.). Investigation of inflammation pathways utilized lipo-polysacchmide 5 ng/ml (SIGMA ALDRICH) and resultant expression of IL-6 and TNF-α genes. Analysis of cellular apoptosis was accomplished using agarose electrophoresis of DNA fragmentation.

Quantitative RT-PCR. RNA isolation was accomplished utilizing TRIZOL reagent (INVITROGEN Corporation, Carlsbad, Calif.) per manufacturer's guidelines. cDNA was synthesized using the ISCRIPT SELECT cDNA Synthesis Kit (BIO-RAD, Hercules, Calif.) PCR was done using SYBER Green detection reagents (QUANTA BIOSCIENCES, Gaithersburg, Md.) and appropriate primers for mIL-6, mTNF-α, and β-Actin (INTEGRATED DNA TECHNOLOGIES, Coralville, Iowa). Samples were amplified using a MYIQ real-time PCR detection system (BIO-RAD).

Electrophoretic Assay. Cells were washed with PBS wash and removed from the substrate. Cells were lysed using a cell lysis solution (10 mM Tris-HCL, pH 8.0, 10 mM EDTA, 1% Triton X-100) and incubated with RNase and Protinase K. DNA was extracted using a 2% isoamyl alcohol (25:24:1) solution and precipitated in isopropanol. Remaining pellet was washed in 70% ethanol and re-suspended in DEPC water. DNA fragmentation was characterized via a 0.8% agarose gel using sodium borate buffer and ethidium bromide staining.

Spectroscopy Analysis. Microscope glass slides were cut to size and coated with a primary base layer of Parylene A as described previously. 0.25 mg of doxombicin (US PHARMACOPIA) was desiccated onto the individual glass sections and a secondary eluting layer of Parylene A (150 mg) was deposited. Samples were placed in a 12 well plate immersed in 1.0 ml of PBS for 10 min, 20 min, 40 min, 1 hour, 4 hour, and 24 hour increments. After each time point the solution was removed and the drug eluting glass disks were transferred to a vacant well and replenished with 10 ml of PBS. Remaining solutions were analyzed in a DU Series 700 UV-Vis Scanning Spectrophotometer (BECKMAN COULTER, Fullerton, Calif.).

Example 5

Characterization of Drug Elution from the Parylene A Bi-Layer

Figure 41A:
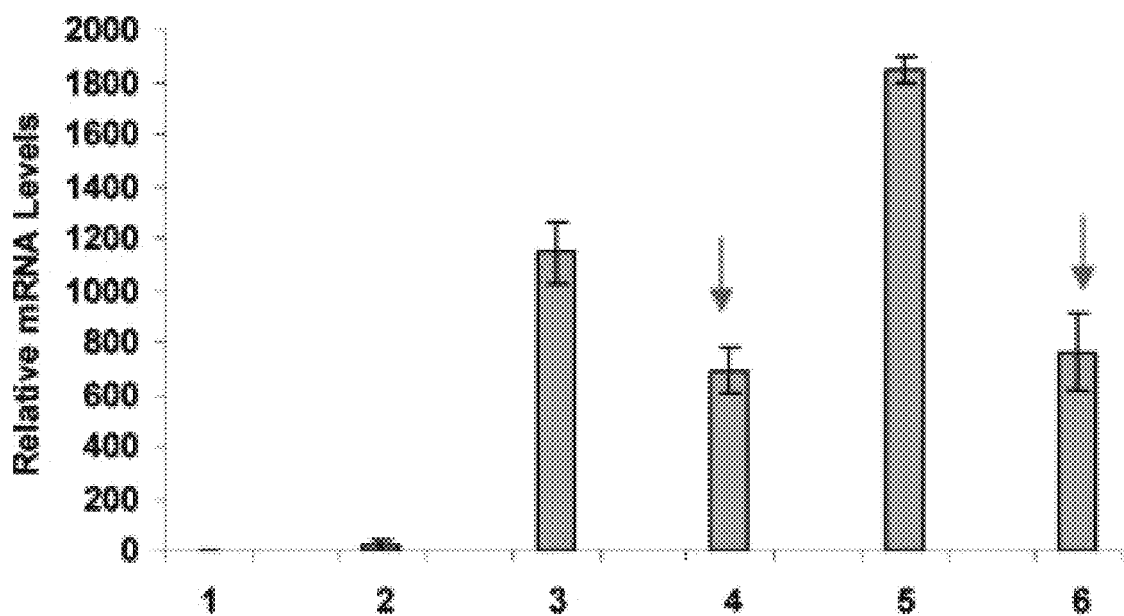
FIGS. 41A and 41B show graphs of gene expression of a) inflammatory cytokine Interleukin-6 (IL-6) and b) inflammatory cytokine Tumor Necrosis Factor-α (TNF-α). LPS stimulation of RAW 2647 macrophages occurred during the last 4 hours of a 24 hour incubation. 1) −LPS; cellular growth on a glass slide, 2) −LPS; comparable growth on Parylene A coated slide, 3)+LPS; cellular response on Parylene A substrate, 4)+LPS; resultant action of a DEX film upon Parylene A coating, 5)+LPS; Parylene A bi-layer, and 6)+LPS; Parylene A bi-layer incorporated with a DEX film. Arrows indicate DEX mediated decrease.
Figure 41B:
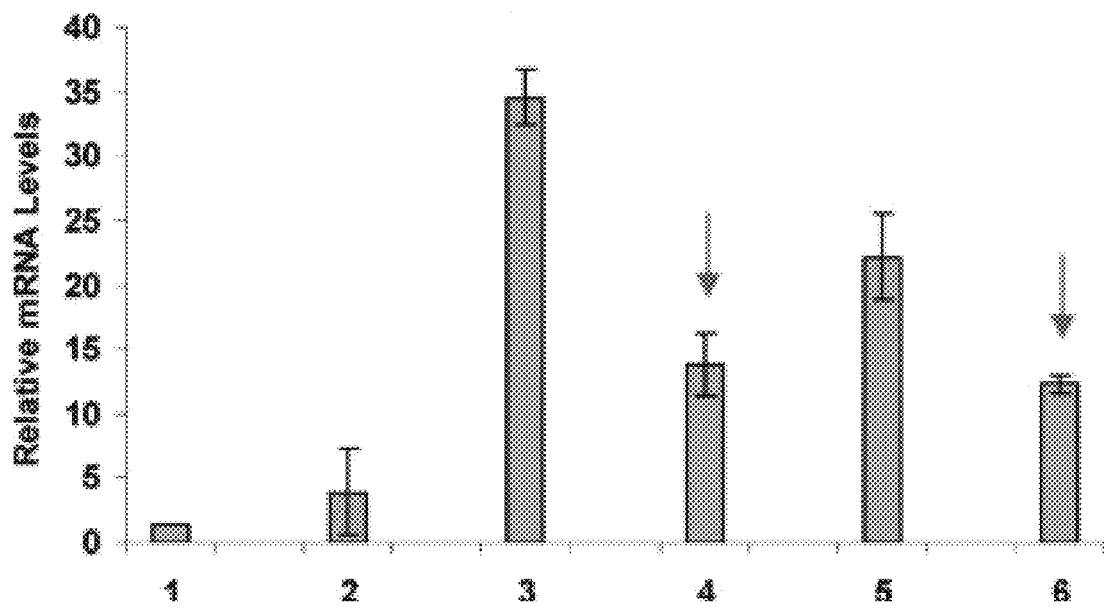
Figure 42:
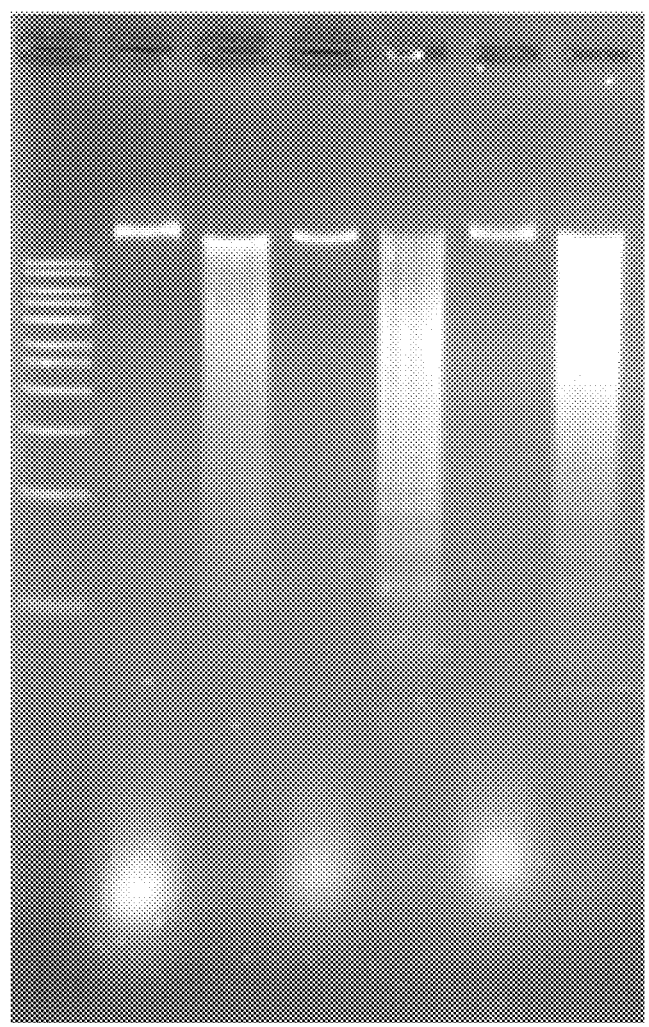
FIG. 42 shows an electrophoretic gel depicting doxorubicin induced DNA fragmentation of RAW 264.7 macrophages. 1) Cells grown upon plain glass slide. 2) Addition of aqueous doxorubicin to the previously indicated conditions showing fragmentation of DNA indicative of cells actively undergoing apoptosis. 3) Parylene A substrate showing no apoptotic response to the amine functionalized surface. 4) DOX film applied to previous sample revealing the ladder banding pattern of DNA fragmentation. 5) Parylene A bi-layer revealing no significant apoptotic response to the additional secondary eluting layer. 6) DOX loaded into the Parylene A bi-layer showing apoptotic fragmentation of DNA.

Characterization of drug elution from the Parylene A bi-layer was accomplished by comparing the activity of the eluted drug to the respective controls. In all tests, elution of the drug from controls and pinhole coated surfaces were equivalent as determined by the concentration and function of the released drug. This suggested that the secondary elution layer imposed no negative effect of upon drug function or elution. This was evident from the graphical representation of DEX mediated gene expression (SEE FIGS. 41A-B), and of DOX mediated apoptosis, demonstrated by the onset of DNA fragmentation (SEE FIG. 42). The application of DEX has been shown to mediate downstream cytokines IL-6 and TNF-α (Jeong et al. 2003, 144, 4080, Maeda et al. Hearing Research 2005, 202, 154, herein incorporated by reference in their entireties). Lipopolysaccharide activation of the inflammatory cytokines IL-6 and TNF-α were decreased through the presence of DEX (SEE FIGS. 41A-B).

Doxorubicin functions through the intercalation of DNA promoting cell mediated apoptosis (Jurisicova et al. Cell Death Differ, 2006, 13, 1466, Wang et al. Biochemical Journal 2002, 367, 729, Huang et al. Nano Letters 2007, 7, 3305, herein incorporated by reference in their entireties). Apoptotic behavior of RAW 264.7 cells was confirmed through the presence of laddering, indicative of cellular apoptosis, as noted in the electrophoretic separation of DNA (SEE FIG. 42). The amine functionalized surface had no negative effect on cell growth in regards to stimulating apoptotic pathways. The elimination of any detrimental growth effect can be asserted.

Figure 43A:
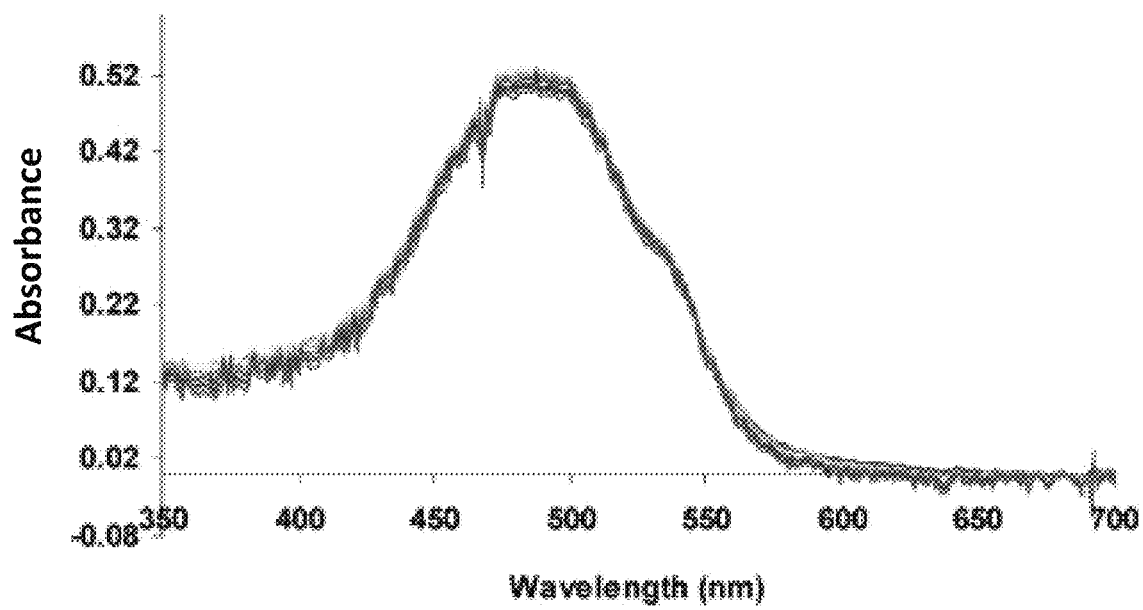
FIGS. 43A-C show (a) additive spectroscopic scans showing the complete release of DOX from control samples consisting of DOX applied to a base layer of Parylene A deposited on glass disks, (b) additive spectroscopic scans showing the gradual release of DOX from a pinhole sample consisting of DOX introduced between alternating amounts Parylene A deposited on glass disks, and (c) comparison of peak absorbance values (480 nm) of DOX elution in PBS over 4 hours.
Figure 43B:
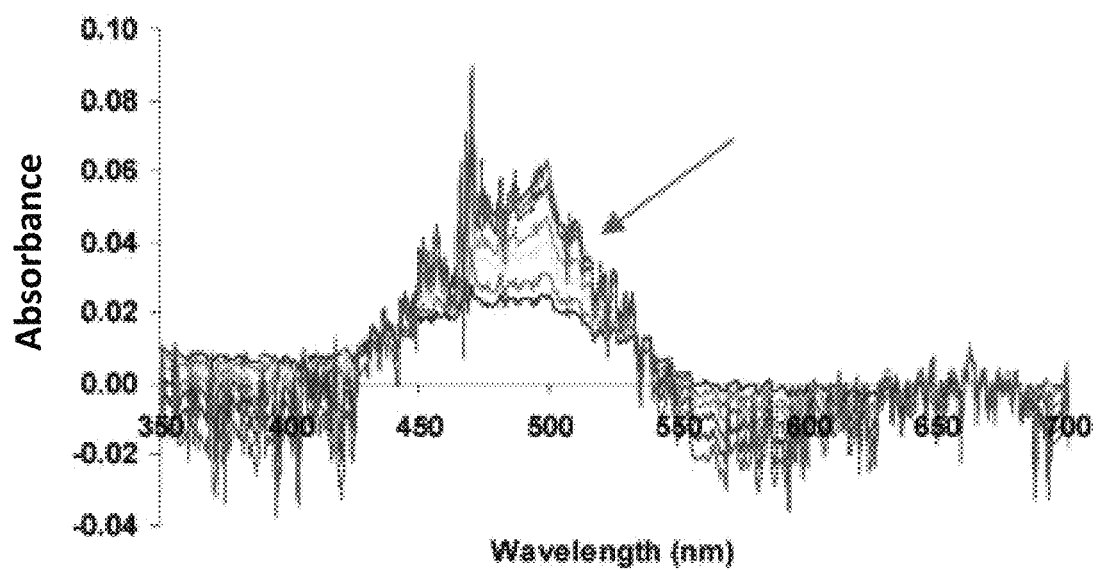
Figure 43C:
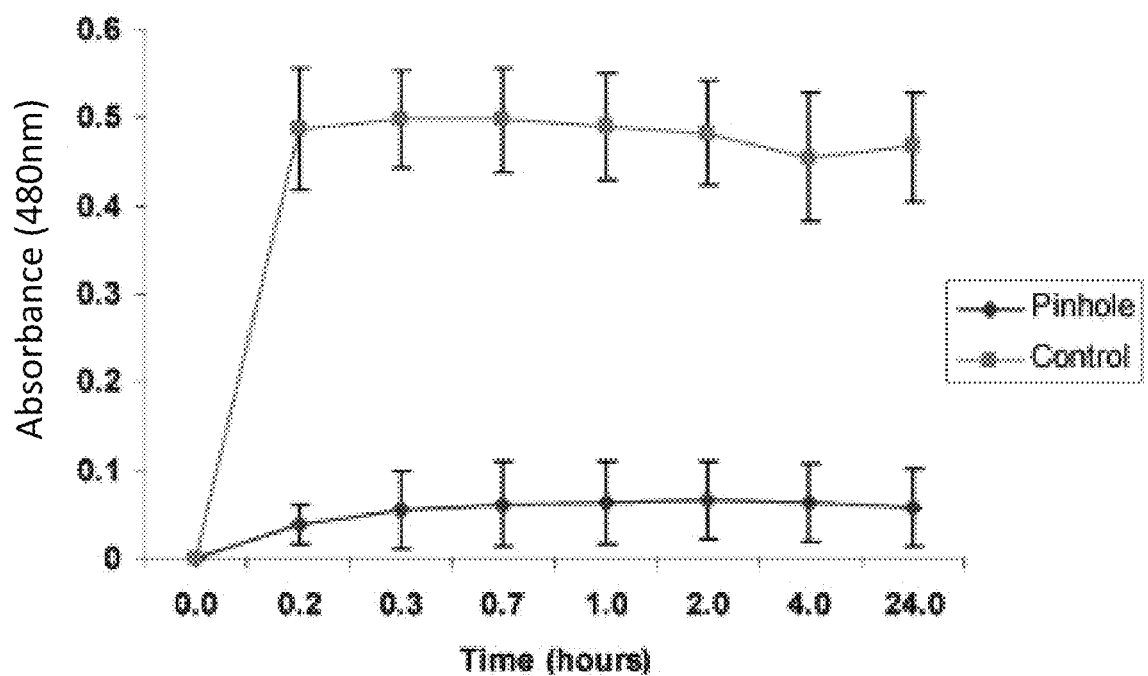

Spectroscopic analysis revealed the degree of DOX elution over time (SEE FIGS. 43A-C). Compared to the control (SEE FIG. 43A), the gradual elution of DOX from alternating layers of Parylene A (SEE FIG. 43B) is evident. Further analysis integrating each sample was taken at the maximum absorbance of DOX at 480 nm over time (SEE FIG. 43C). Contrasting absorbance values provide further evidence to the porous nature of micro to nanoscale depositions of Parylene A. The experiments conducted during the development of embodiments of the invention affirmed the presence of physical pores, present within the superficial Parylene A layer, due to incomplete polymerization of the substrate surface.

It has been contemplated that the deposition of the non-adherent drug film to the underlying primary surface could result in shearing off of the secondary elution layer under applied mechanical forces. However, the experiments conducted during the development of embodiments of the invention, most notably the spectroscopic analysis (SEE FIGS. 43A-C), support the notion of pinhole mediated release. Delamination of the secondary layer would have resulted in bi-layer elution rates comparable to that of the control, rather than the pinhole mediated release observed.

While the precise mechanism of pinhole formation has yet to be determined, it is clear that by introducing increasingly lower quantities of Parylene A into commercially available Parylene deposition systems results in the formation of porous films; although the present invention is not limited to any particular mechanism of action and an understanding of the mechanism of action is not necessary to practice the present invention. Experiments conducted during the development of embodiments of the invention were focused on porosity in regards to Parylene A. It is contemplated that deposition kinetics for other para-p-xylene derivatives may differ due to the range of functional groups and respective molecular masses.

Example 6

Compositions and Methods for the Fabrication and Characterization of Nanodiamond-Embedded Microfilm Devices ND suspension and functionalization with DOX. NDs were functionalized and dispersed. Upon ND ultrasonication (100 W, VWR 150D sonicator) for 30 minutes, DOX and ND solutions were centrifuged together at appropriate concentrations at a 4:1 ratio. Addition of NaCl helped facilitate the process.

Materials and Device Fabrication. A conformal 3 g base layer of Parylene C was deposited on pre-cut 2.5 cm×2.5 cm glass slides with a SPECIALTY COATING SYSTEMS (SCS) PDS 2010 LABCOATER (SCS, Indianapolis, Ind.). The Parylene layer was oxidized via oxygen plasma treatment in a HARRICK Plasma Cleaner/Sterilizer (Ithaca, N.Y.) at 100 W for one minute. A DOX-ND solution was then added to the base layer so that the final DOX-ND concentration in solution was 6.6 µg/ml. Subsequently, solvent evaporation occurred in isolation at room temperature. Following DOX-ND deposition, an ultra-thin 0.15 g palylene C layer was deposited as an elution-limiting and control element. The final layer of Parylene C was treated with oxygen plasma at 100 W for one minute. Parylene C was pyrolized into a gaseous monomer at 690° C., and deposited at room temperature under vacuum conditions for all depositions. The preceding parameters apply to devices fabricated for spectroscopy studies. The present invention is not limited to these parameters. The concentration of DOX-ND was adjusted for devices used in the DNA fragmentation assay so that the final DOX-ND concentration in solution was 33 µg/ml.

Atomic Force Microscopy (AFM) Characterization. ASYLUM MFP3D AFM (Santa Barbara, Calif.) images of the samples were taken to identify the structure and interaction between proteins. Image dimensions were 20 µm×20 µm. Contact mode imaging at line scan rates of 03 to 0.5 Hz were performed in at room temperature with OLMPUS TR800PSA 200 µm length silicon nitride cantilevers (Melville, N.Y.).

Spectroscopic Analysis. Samples were immersed in 2 mL of nanopure water in 6-well plates and placed in an incubator at 37° C. and 5% $CO_2$. At every 24-hour interval, samples were transferred to another well to avoid residue contamination while the remaining 2 mL of eluate was collected. A full wavelength scan from 350 nm-700 nn was performed on 100 µl of the eluate with a BECKMAN COULTER DU730 Life Science UVl Vis Spectrophotometer (Fullerton, Ca).

Contact Angle Measurements. Static contact angles were measured with 10 µl of DI water with a RAME-HART, Inc. Imaging System and Auto Pipetting System (Mountain Lakes, N.J.).

DNA Fragmentation Assay. RAW 264.7 murine macrophages (ATCC, Manassas, Va.) were cultured in Dulbecco's modification of Eagle's medium (CELLGRO, Hemdon, Va.) supplemented with 10% Fetal Bovine Serum (ATCC) and 1% penicillin/streptomycin (CAMBREX, East Rutherford, N.J.). Cells were grown in an incubator at 37° C. and 5% $CO_2$. The cells were plated on two sets of uncovered and covered devices at ~40% confluence, for 16 hours with one set and 20 hours with the other, to contrast progression of apoptosis over time as a result of DOX-ND elution from the native and porous devices. DOX (2.5 µg/mL) served as a positive control for apoptosis, and culture media as a negative control. Cell harvest comprised of a PBS wash and subsequent lysis in 500 µl lysis buffer (10 mM Iris-HCl, pH 8 . . . 0, 10 mM EDIA, 1% Triton X-100) for 15 minutes. 30-minute incubations with RNase A (313 µg/mL) and proteinase K (813 µg/mL) that occurred at 37° C. followed the buffer treatment, separately. The samples then underwent phenol chloroform extraction, followed by DNA isolation and precipitation in 2-propanol at −80° C. for at least 2 hours. After washing with 70% ethanol, the samples were resuspended in water and loaded onto a 0.8% agarose gel in sodium borate buffer, run, and stained with ethidium bromide (SHELTON SCIENTIFIC, Shelton, CI).

Example 7

Compositions and Methods for the Fabrication of Hybrid Parylene-ND Films

Figure 46A:
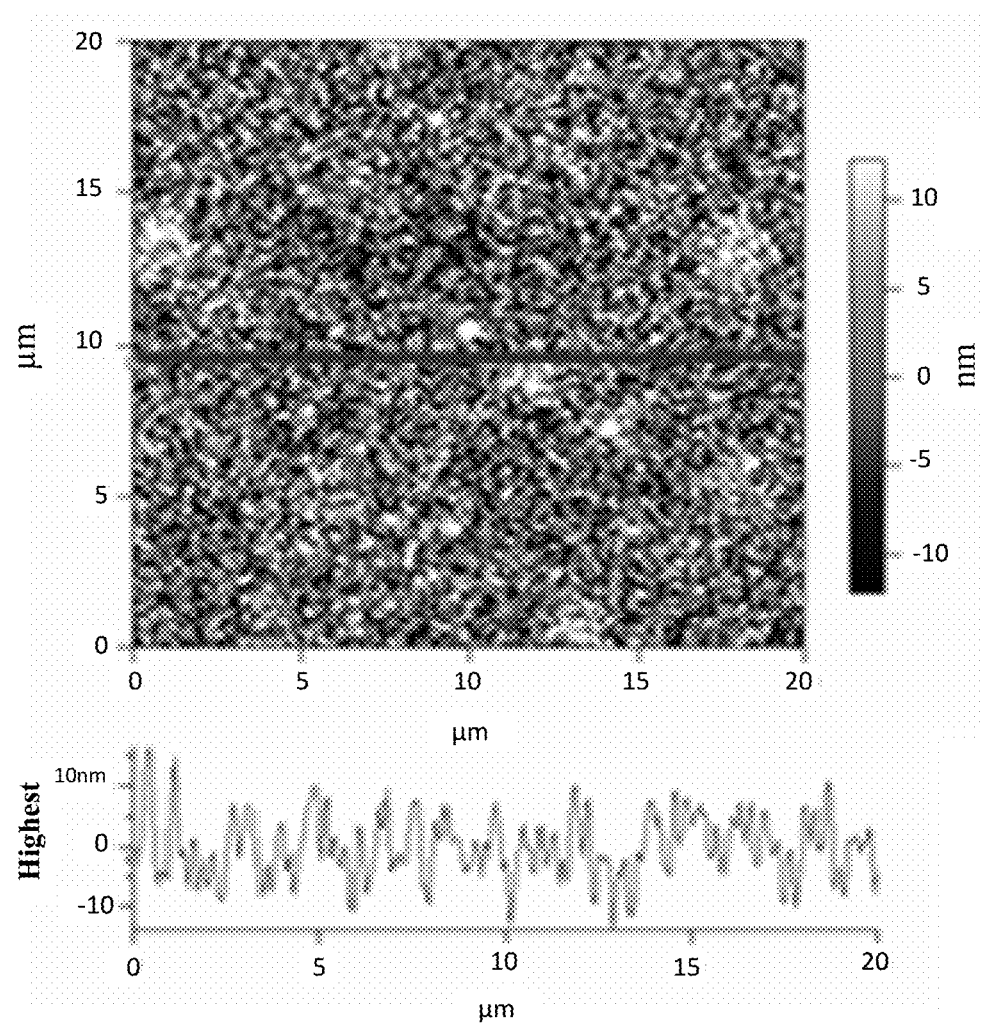
FIGS. 46A-D show atomic force microscopy (AFM) images of Parylene C: a) native Parylene C (roughness of 6.245 nm); b) plasma-treated Parylene C (roughness of 9.291 nm); c) DOX-NDs deposited on a plasma treated layer of Parylene C; d) DOX-NDs deposited on a plasma treated layer of Parylene C, and covered with an additional thin layer of Parylene C.
Figure 46B:
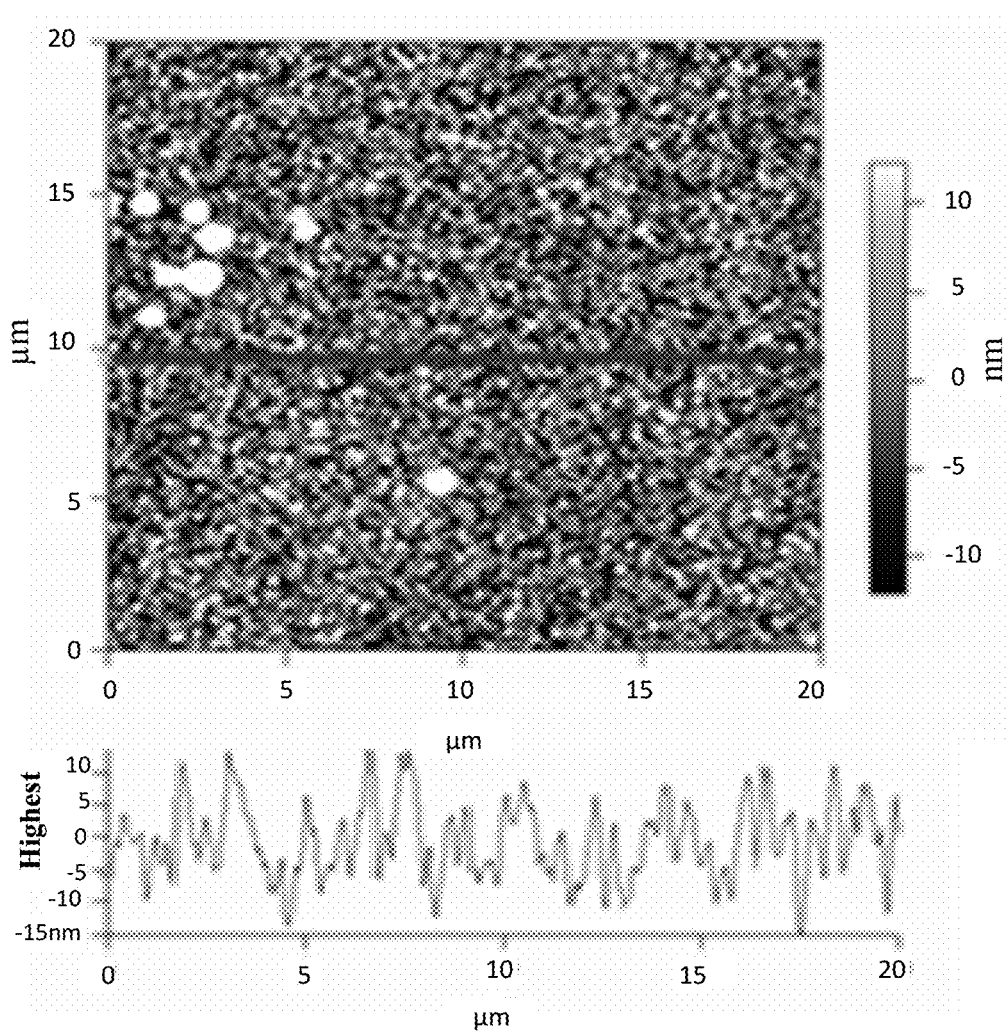
Figure 46C:
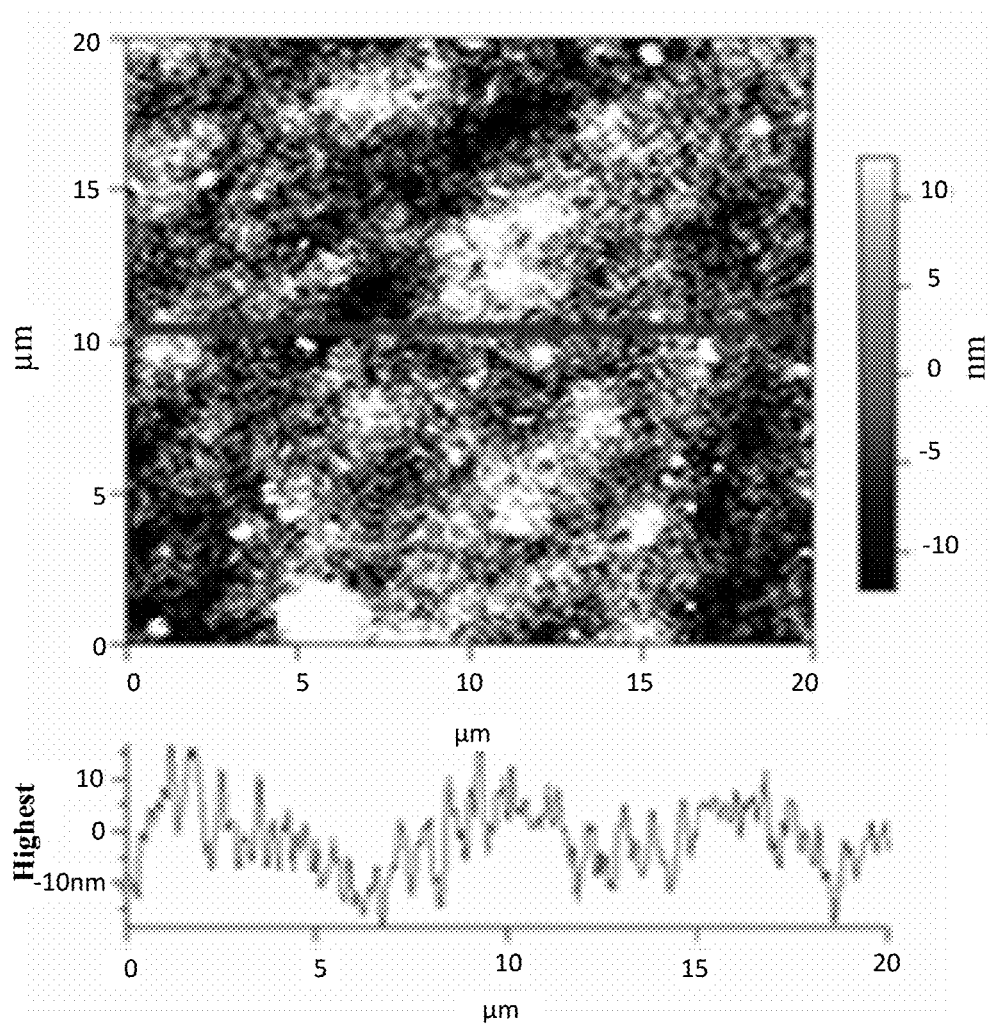
Figure 46D:
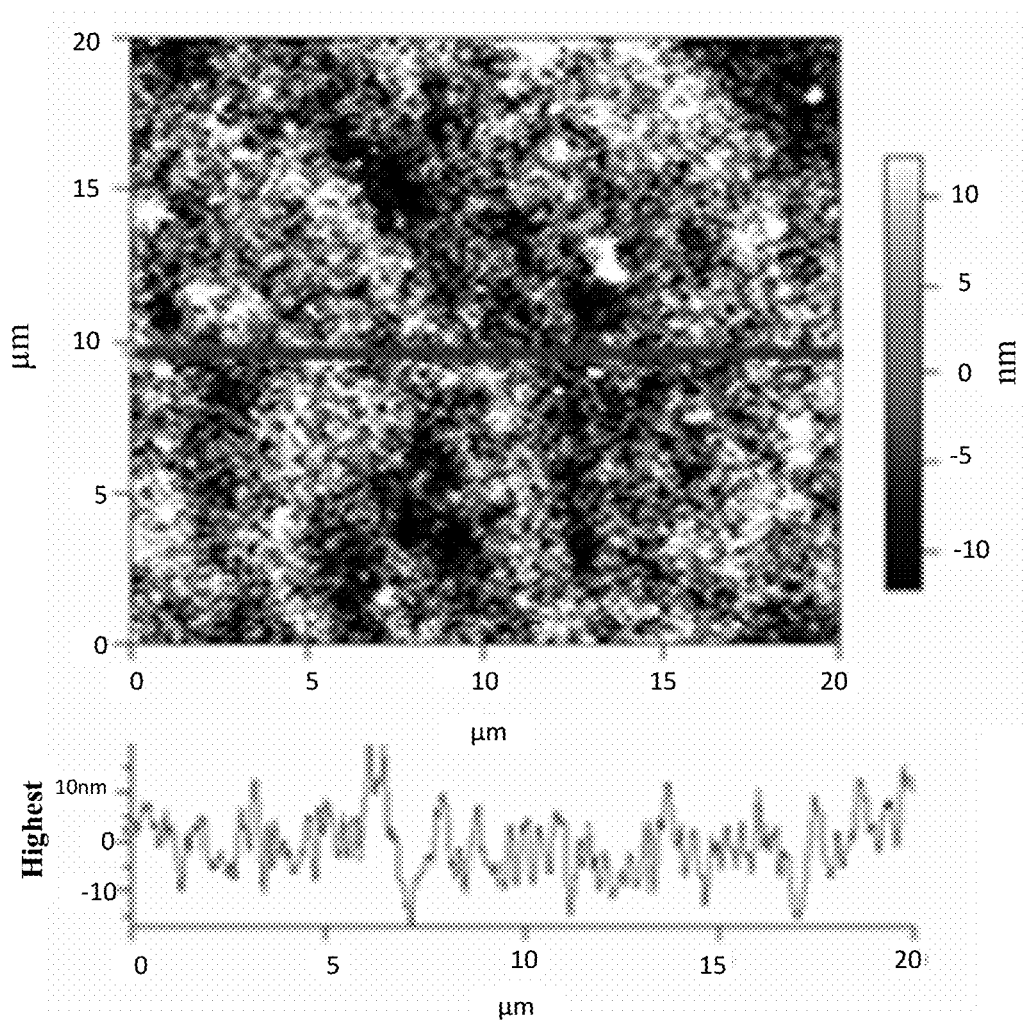

For elution and biological assay studies, a conformal and impenetrable base layer of Parylene C was deposited atop pre-cut glass slides. Within the Parylene deposition machine, the Parylene C dimmer (di-para-xylylene) is pyrolized into monomer form (para-xylylene) and then deposited at room temperature in a vacuum, conditions under which the monomers spontaneously formed polymers (Gorham. Journal of Polymer Science, 1966, 4, 3027, herein incorporated by reference in their entireties). The process was carried out under ambient conditions, hence, the functionality and structure of the DOX-ND conjugates were not harmed or inhibited. The base layer formed a flexible foundation upon which an implantable patch could be constructed, and simultaneously provided an impermeable and pinhole-free platform for unidirectional drug-elution. Newly deposited Parylene is hydrophobic (SEE FIG. 46A). Additional surface processing was performed to enhance drug deposition uniformity and elution. The Parylene layers were oxidized via oxygen plasma treatment, which has been shown to increase surface roughness while adding $CO_3^-$ and carbonyl (C=O) groups, effectively creating a hydrophilic surface (SEE FIG. 46B) (Lee. Journal of the Korean Physical Society, 2004, 44, 1177, herein incorporated by reference in its entirety). Oxidization of Parylene C surfaces have been shown to be stably hydrophilic after treatment, while increasing the level of cell adhesion (Chang et al. Langmuir, 2007, 23, 11718, herein incorporated by reference in its entirety). Appropriate amounts of a DOX-ND solution composed of a 4:1 ratio of NDs and DOX of concentrations 330 µg/mL and 66 µg/mL, respectively was then added to the base layers via solvent evaporation at room temperature to produce a final concentration of 6.6 ug/mL in solution (SEE FIG. 46C). A second ultra-thin Parylene C layer of patchy porosity was then deposited as an elution limiting element (SEE FIG. 46D). At diminutive Parylene dimer loads, film deposition could not be guaranteed to be conformal and pin-hole free (Spellman et al. Journal of Plastic Film and Sheeting, 1999, 15, 308, herein incorporated by reference in its entirety). With smaller dimer masses, the dimensions and amount of pinholes were increased, acting as an adjustable physical barrier for controlled drug release. Furthermore, this additional thin film provided a structural platform that simultaneously protected the underlying DOX-ND and acted as a base for additional device modifications. This base layer-drug-porous layer configuration has been applied towards studies involving dexamethasone and triblock copolymers in order to assuage inflammation. The final layer of Parylene C was also treated with oxygen plasma.

Example 8

Assessment of Slow-Release Characteristics of Hybrid Parylene-ND Films

Samples were immersed in nanopure water and placed in a 37° C. and 5% $CO_2$ incubator, to simulate physiological conditions. Upon incubation, the pH of nanopure water reduced to a value of pH 3-4. The decline in pH enabled a greater release of sequestered therapeutic than in standard room temperature, although the present invention is not limited to any particular mechanism of action and an understanding of the mechanism of action is not necessary to practice the present invention. Experiments were conducted during the development of embodiments of the invention to assess the slow release potential of the Parylene-ND based patches.

Figure 47:
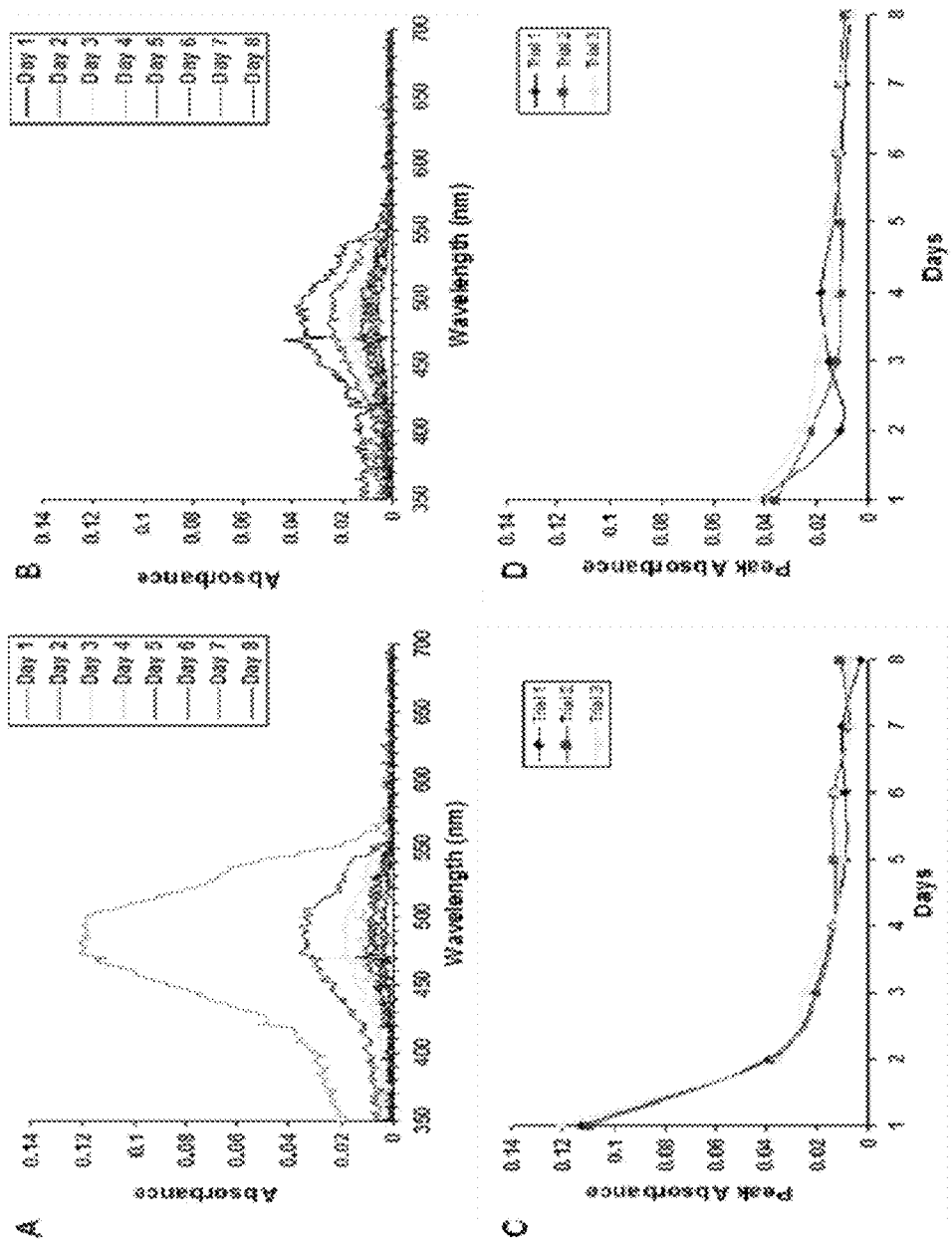
FIG. 47 shows DOX-ND release assessment data. a) Sample UV-vis spectra of eluate collected at 24 hour intervals for samples uncovered with top eluting Parylene element. b) 8 day trials performed for Parylene covered and uncovered samples (optical absorbance measured at 480 nm. c) a long term trial where eluate was collected at various time points and optical absorbance is measured at 480 nm. d) Spectroscopy data at 480 nm plotted against respective DOX concentration.

DOX solubilized in water generated an absorbance signal from approximately 375 to 575 nm, with a peak at approximately 480 nm (SEE FIG. 47A). Absorbance values under 350 nm were not recorded since Parylene C does not absorb strongly at lower wavelengths.

Films that lacked the deposited thin Parylene layer eluted the majority of the deposited drug in the first day, while films that contained the layer demonstrated a more controlled and constant release of therapeutic (SEE FIGS. 47B-C). Controlled and localized elution offered several advantages over conventional systemic drug administration, including the ability of maintaining a desired concentration over long periods of time with a single administration (Langer. Science, 1990, 249, 1527, herein incorporated by reference in its entirety). Moreover, it is contemplated that DOX has poor penetration into tumor tissues, due to low diffusion rates caused by small interstitial spaces and strong intracellular binding (Lankelma et al. Clinical Cancer Research, 1999, 5, 1703, herein incorporated by reference in its entirety). Due to this effect, steep DOX concentration gradients have been observed when injected in vivo, with the highest concentrations localized near microvessels. It is contemplated that a gentler concentration gradient can instead be created with continuous treatment. Drugs with poor penetration, like DOX, also have been shown to have low cell death thresholds, as they only affect cells located at the periphery. Maintained continuous treatment could alleviate this obstacle by eliminating additional layers of cells through lengthened time periods, without supplemental therapies (Tannock et al. Clinical Cancer Research, 2002, 8, 878, herein incorporated by reference in its entirety), although the present invention is not limited to any particular mechanism of action and an understanding of the mechanism of action is not necessary to practice the present invention. As an additional benefit, sustained release can prevent oncogenic regrowth between chemotherapy sessions.

Small dosages of drugs applied through continuous infusions have been demonstrated to provide a gradual increase in penetration while reducing additional toxicity effects. Large doses of DOX administration have led to nausea, vomiting, alopecia, myelosuppression and eventual congestive heart failure. With a continuous infusion of DOX, patients experienced lower cardiotoxicity and reduced occurrence and severity of side effects than normal, even at higher cumulative dosages with no noticeable effects upon drug efficacy (Legha et al. Annals of Internal Medicine, 1982, 96, 133, Legha et al. Cancer, 1982, 49, 1762, herein incorporated by reference in their entireties). It has been contemplated that cardiotoxicity might be related to peak plasma levels of drug instead of cumulative drug dosage.

In pursuit of the benefits attributed to slowed continuous release, the hybrid films were tested for their initial release profile over the first eight days (SEE FIG. 47B). Uncovered DOX-ND complexes eluted at least three times more DOX over the first day than films with the additional elution control layer, which released drug at a nearly constant rate after 24 hours. It is contemplated that the muted initial release of the covered films aids in reducing symptoms associated with spiked levels of drugs that result from direct drug administration. After eight days, there remained a great deal of DOX-ND complexes on both uncovered and covered patches upon visual inspection. It is contemplated that the residual DOX-ND was due to large aggregations of NDs surrounding an inaccessible DOX core or physical entrapment onto the uneven coarse oxidized Parylene surfaces.

In order to evaluate the long term performance of the patch, the experiment was repeated over a month-long period (SEE FIG. 47C). A similar initial trend comparable to the eight-day results was observed. The initial surge in elution of DOX-ND from the uncovered film affected drug preservation and dosage. The decreased ability of the uncovered film in sequestering drug was a direct cause for the increased elution over the first three days. Samples were allowed to elute for a period longer than 24 hours at specific times in order to determine extended dosage levels, namely at days 12-16 and 22-29 (SEE FIG. 47C). During the aforementioned periods, covered films eluted a greater total amount of drug than uncovered films, primarily due to the uncovered film's drug reservoir being exhausted at an early stage from its large initial release. Since equal amounts of DOX-ND were coated on both films, the increased elution from the last data point demonstrates the covered hybrid films will elute for a longer period of time than uncovered films.

The decreased drug preservation resulted in increased initial drug dosage, which is important during the nascent phases following implantation. An immediate release of drug following implantation has been shown to cause several negative side effects previously discussed. The ND-Parylene nanofilm device is envisioned to circumvent these effects because the initial elution of DOX from the hybrid film is gradual and tapered, rather than abrupt and rapidly depleted. The robustness and stability of the Parylene based patches were confirmed visually throughout experimentation.

Based on the linear relationship equating spectroscopy measurements with DOX concentrations in water (SEE FIG. 47D), the approximate dosage of the eluate was determined. Uncovered DOX-ND devices initially eluted nearly 90% of the DOX-ND complexes into 2 mL of nanopure water over the first 24 hours to a concentration of approximately 575 µg/mL, with a steep decline in elution to 400 ng/mL after a week. Conversely, samples with a thin Parylene coat maintained a more constant elution rate, ranging from 2 µg/mL to 450 ng/mL in the same time frame. It is contemplated that this continuous elution can alleviate drug loss through blood circulation, extravasation or other methods of excretion (Tannock, Cancer and Metastasis Reviews, 2001, 20, 123, herein incorporated by reference in its entirety).

Example 9

Assessment of Biological Performance of Hybrid Parylene-ND Films

Figure 48:
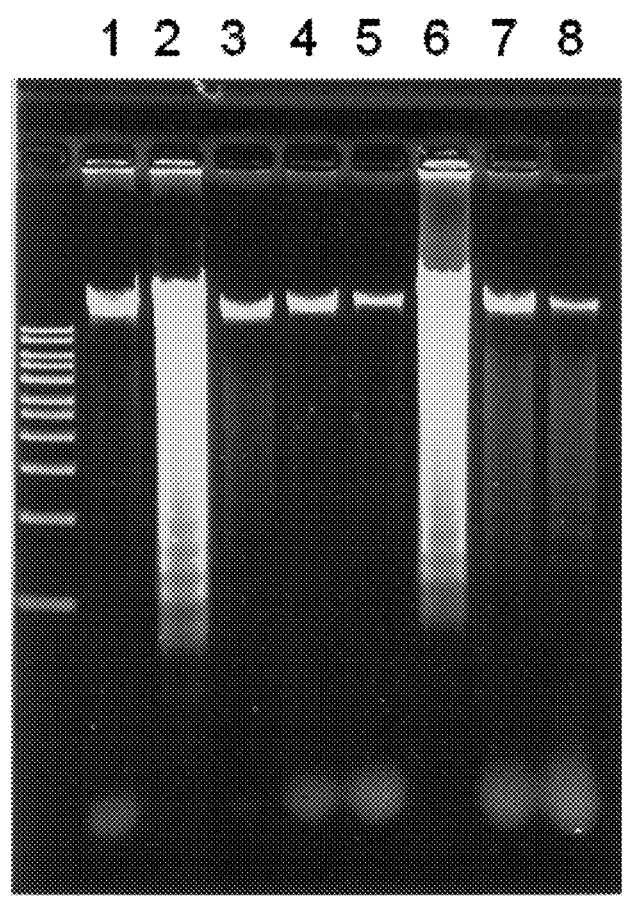
FIG. 48 shows gel electrophoresis assay of DNA from RAW 264.7 murine macrophages incubated for 16 hours (lanes 1-4) and 20 hours (lanes 5-8) on glass (lands 1, 5), DOX-ND on Parylene C (lanes 2, 6), DOX-ND sandwiched between a base layer and pinhole layer of Parylene C (lanes 3, 7), and Parylene with 2.5 μg DOX. Degrees of banding correlate to different stage of apoptosis induced by DOX incubation.
Figure 49:
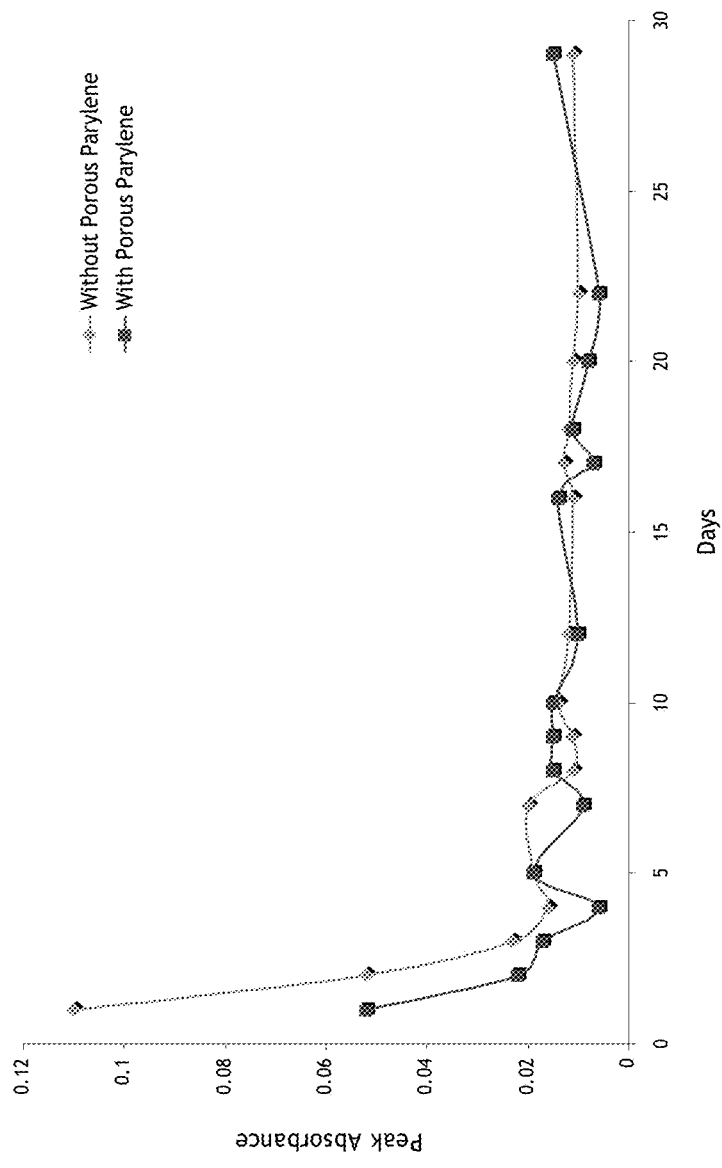
FIG. 49 shows ND-DOX elution from Parylene thin films over 28 days measured via peak absorbance.

Experiments were conducted during the development of embodiments of the invention to examine the biological efficacy and mechanisms of the nanofilm. DNA fragmentation assays monitoring the presence of apoptotic responses were conducted with RAW 264.7 murine macrophages in various culture conditions. RAW 264.7 murine macrophages were selected due to their natural recruitment to foreign bodies such as implants. The patterned degradation of DNA that is characteristic of apoptosis appeared as a result of exposure to DOX, and was observed in the gel for the positive control and all samples containing DOX-ND (SEE FIG. 48). Two sets of samples were harvested after 16 (lanes 1-4) and 20 hours (lanes 5-8) of growth. Lanes 1:5, 2:6, 3:7, and 4:8 correlated to the negative and positive controls, the uncovered device, and the covered porous device, respectively. The ability of DOX-ND complexes to naturally reduce DOX elution rates was seen when comparing lanes 3, 4, 7 and 8 to the 2.5 µg/mL positive controls. Whereas positive controls prompted rigorous DNA fragmentation, the DOX-ND devices displayed a more gradual and delayed onset of apoptosis, which can reduce the severe side effects that result from a sudden spike in DOX dosage. In addition, the DOX-ND devices were loaded with over 13 times the concentration of DOX compared to the positive control. Therefore, the assay additionally attests to the slow-elution effects that are native to the DOX-ND complex. Furthermore, the relative degrees of banding in the gel suggested the onset of apoptosis is dependent on DOX dosage. This interaction was most apparent when comparing uncovered and porous devices at lanes 3 and 4 (16 hours) with lanes 7 and 8 (20 hours). At 16 hours some fragmentation had occurred in the uncovered device as a result of greater DOX-ND elution and a higher concentration of DOX-ND in solution due to the lack of a porous Parylene layer, which further inhibited the onset of apoptosis. At 20 hours, some fragmentation had occurred in both uncovered and porous samples. The fragmentation assay correlated with the spectroscopy data, revealing the different relative rates of elution from porous and uncovered substrates, further demonstrating the sequestration abilities of the film, Moreover, the data demonstrated the ability of the device to deliver at least 13 times more drug to a localized spot. The combined effects of localized delivery and gradual therapeutic elution of a large reservoir of drug offered a safer, yet more enduring and potent drug delivery device.

Example 10

Compositions and Methods for Preparation of Hydrogel Carriers ND-Conjugated Therapeutics DOX-ND conjugates solutions were fabricated in accordance to protocols (H. Huang et al. Nano Letters, vol. 7, pp. 3305-3314, 2007, herein incorporated by reference in its entirety). Upon overnight ND ultrasonication (100 W, VWR 150D sonicator) and filtration (Millex-GN, 0.2 µm Nylon, Millipore, Billerica, Mass.) to remove large ND aggregates, ND and DOX solutions were mixed thoroughly in a 5:1 ratio of 12.5 mg/mL and 2.5 mg/mL concentrations for NDs and DOX, respectively in an aqueous 2.3 µM NaOH solution.

A 200 µL precursor PEGDA (Sigma) solution consisting of PEGDA, the photoinitiator 2,2-dimethoxy-2-phenylacetophenone (DMPA) dissolved in methanol, and nanopure water was mixed with 100 µL of nanopure water, 2.5 mg/mL DOX or the aforementioned DOX-ND conjugate solution for negative control, DOX:PEGDA and DOX-ND:PEGDA hydrogels, respectively. The resulting solution consisted of 50% PEGDA, 1% DMPA and drug or drug-ND conjugates solubilized in water. These solutions were then mixed thoroughly and photopolymerized for 2 minutes with a handheld UV lamp (UVP UVGL-58, Cambridge, UK) at 365 nm exposure. The resulting hydrogels were 5 mm and 16 mm in thickness and diameter, respectively.

Figure 50:
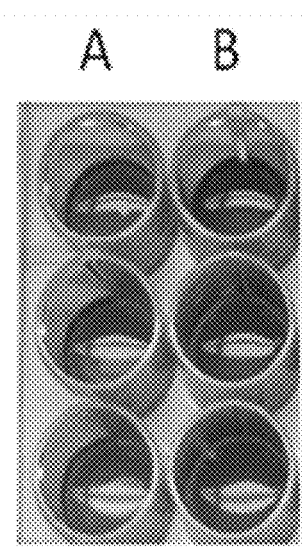
FIG. 50 shows triplicate trials of ND deficient (A) and ND embedded (B) 50% PEGDA hydrogels. Hydrogels contained 250 μg/mL of DOX in solution prior to submersion.

Upon fabrication, hydrogels were incubated in 1 mL of either nanopure water or PBS in 24 well plates (BD Falcon) and repeated in triplicate within physiological conditions (37° C. and 5% CO2) (SEE FIG. 50). At 24 hour intervals, the eluate was collected, refilled and analyzed via UV-vis spectroscopy. Release characterization was straightforward as solubilized DOX generates an absorbance signal which peaks at 480 nm.

Characterization was performed with a FEI Quanta 600F Sfeg Environmental Scanning Electron Microscope (ESEM) in low vacuum mode (1.20 Torr) at an accelerated voltage of 20 kV. ESEM is well suited for characterization of hydrogels since samples do not have to be coated with an electrically conductive material. In addition, since ESEMs operate relatively higher chamber pressures, hydrogels can remain hydrated during imaging (Zheng. Advanced Functional Materials, vol. 11, pp. 37-40, 2001, herein incorporated by reference in its entirety).

Example 11

Hydrogel Carriers and ND-Conjugated Therapeutics, Methods of Use

Figure 51:
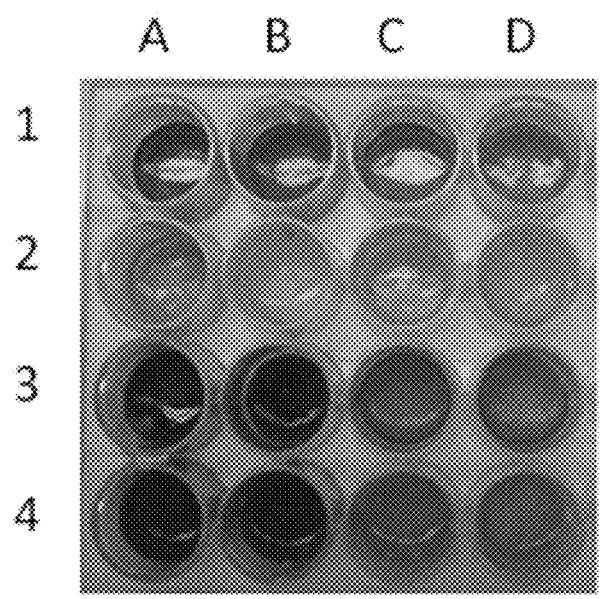
FIG. 51 shows sample hydrogels: rows 1, 2: DOX-PEGDA hydrogels before and after 24 hour incubation in pure water, rows 3, 4: DOX-ND:PEGDA hydrogels before and after 10 day incubation, column A: 50% PEGDA with 250 μg/mL of DOX, column B: 25% PEGDA with 250 μg/mL DOX, column C: 50% PEGDA with 125 μg/mL DOX, column D: 25% PEGDA with 125 μg/mL DOX.

Experiments conducted during development of embodiments of the present invention demonstrating the sequestering abilities of ND-PEGDA hydrogels were visually analyzed (SEE FIG. 51). Hydrogels that lacked NDs (SEE FIG. 51, Rows 1, 2) rapidly released the majority of the drug after 24 hours. In comparison, hydrogels encapsulating NDs (SEE FIG. 51, Rows 3, 4) exhibited no significant visual evidence of drug release even after 10 days of incubation. The results were consistent across varying PEG compositions.

Figure 52:
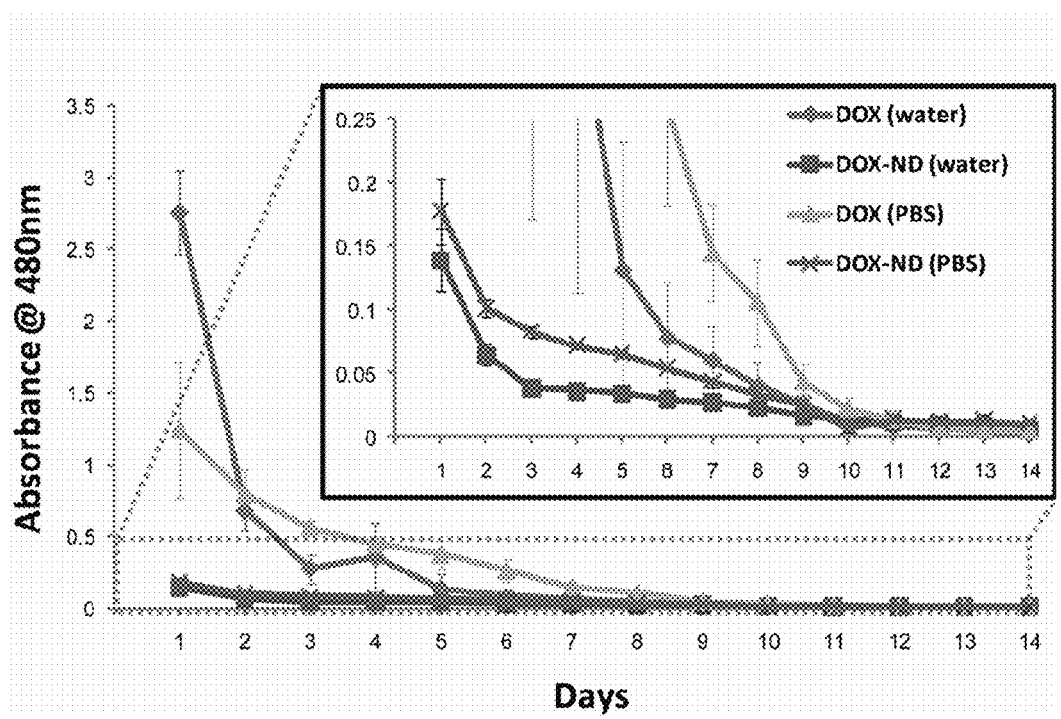
FIG. 52 shows UV-vis spectra of eluate collected every 24 hours from hydrogels of indicated drug and ND composition in nanopure water or PBS.

Elution results demonstrated that DOX-ND:PEGDA matrices released diminutive quantities of drug as compared to DOX:PEGDA samples (SEE FIG. 52). Within standard DOX:PEGDA hydrogels, the majority of the reservoir of drug eluted after a few days while ND:PEGDA hydrogels retained the majority of DOX for at least two weeks. PEGDA hydrogels lacking NDs incubated in PBS released the majority of the drug within the first week as compared to the first few days as with hydrogels incubated in nanopure water. DOX is less soluble in PBS (Pierstorff et al. Nanotechnology, p. 445104, 2008, herein incorporated by reference in its entirety). This effect is evident within the few days of incubation, as ND lacking hydrogels initially release about 20× more drug than ND:PEGDA samples in nanopure water.

There are several advantages to avoiding the 'burst release' common to many hydrogels (Huang & Brazel. Journal of Controlled Release, vol. 73, pp. 121-136, 2001, herein incorporated by reference in its entirety). These include, but are not limited to: reducing drug concentrations to under toxic levels, maintaining and extending lifetimes of drug release devices, prevention of any wasted therapeutic and avoiding unpredictable initial therapeutic release profiles. Although, methods have been developed to limit burst release, they require additional complex steps or major PEG compositional changes (Catellani et al. in Migliaresi, C., Et Al., 1988, pp. 169-174, Lee. Polymer, vol. 25, pp. 973-978, 1984, Wheatley et al. Journal of Applied Polymer Science, vol. 43, pp. 2123-2135, December 1991, Lu et al. Aiche Journal, vol. 44, pp. 1689-1696, July 1998, herein incorporated by reference in their entireties). In some embodiments, the present invention provides a reservoir of drug that can avoid burst release without the addition of complex processing steps towards hydrogel fabrication.

Hydrogels containing NDs exhibited more uniform and constant release across two weeks. The majority of drug eluted from the ND lacking hydrogels in a seemingly diffusion-based manner (Gayet & Fortier. Journal of Controlled Release, vol. 38, pp. 177-184, 1996, Sawhney et al.

Macromolecules, vol. 26, pp. 581-587, February 1993, herein incorporated by reference in its entirety). Comparatively, hydrogels containing NDs released small amounts of drug at a near constant rate after the first 24 hours. Within standard hydrogels, release profiles are initially governed through diffusion. As diffusion effects wear off, hydrogel degradation mechanisms reliant on hydrogel composition dominates, eventually becoming the central factor responsible for the majority of therapeutic release (West & Hubbell. Reactive Polymers, vol. 25, pp. 139-147, 1995, herein incorporated by reference in its entirety). Since ND:PEGDA hydrogels sequester drug extremely well and avoid diffusion-based release, the small amounts of drug are hypothesized to be mainly due PEG degradation. It has been noted that if mesh sizes are decreased, then slow-released can be enhanced, but at the expense of increased brittleness (Scott & Peppas. Biomaterials, vol. 20, pp. 1371-1380, 1999, herein incorporated by reference in its entirety). By dispersing NDs within the matrix, the flexibility of the hydrogel can stay intact while simultaneously providing slow-release.

Figure 53:
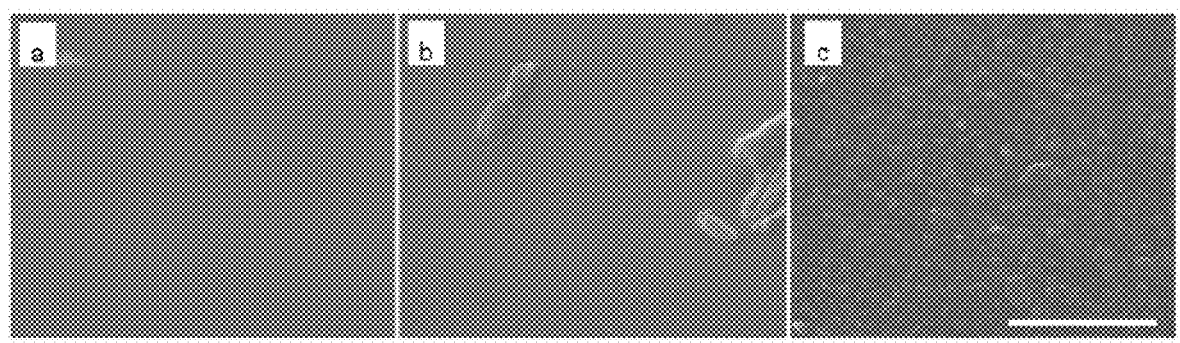
FIG. 53 shows ESEM images of (a) PEGDA, (b) DOX:PEGDA and DOX-ND:PEGDA hydrogels at 1000× magnification and 1.20 Torr; scale bars=50 μm.

A uniform dispersion of NDs was observed due to the in situ incorporation within the PEGDA precursor solution. ESEM topographical images compare PEGDA, DOX:PEGDA and DOX-ND:PEGDA (SEE FIG. 53). The dispersion of NDs within the hydrogel matrix is easily observed (SEE FIG. 53C). This method of mixing the agent within the precursor solution prior to photopolymerization has been utilized in hydrogels to generate uniform dispersions of bioactive materials within the polymer matrix (West & Hubbell. Reactive Polymers, vol. 25, pp. 139-147, 1995, herein incorporated by reference in its entirety). Photopolymerization has several advantageous attributes, namely suitable and simple processing ambient conditions, limited byproduct formation, and elimination of a need for toxic catalysts (Zheng. Advanced Functional Materials, vol. 11, pp. 37-40, 2001, herein incorporated by reference in its entirety). Photopolymerized hydrogels have been accredited towards being a promising material for tissue implantation, replacement and engineering applications (Anseth et al. Journal of Controlled Release, vol. 78, pp. 199-209, 2002, Xin et al. Engineering in Medicine and Biology Society, 2006. EMBS '06. 28th Annual International Conference of the IEEE, 2006, pp. 2091-2093, Bryant & Anseth. Journal of Biomedical Materials Research Part A, vol. 64A, pp. 70-79, January 2003, herein incorporated by reference in their entireties). As hydrogels can be formed via photopolymerization in situ, hydrogels can adapt, be molded into complex shapes and adhere strongly through attachment of microtextures within the tissue complex. Experiments conducted during development of the present invention indicate that ND encapsulated hydrogels provide a localized source of slow drug release for biomedical applications (e.g. adjuvant therapy helping to localize and slow release therapeutic on the surface of tumors or damaged blood vessels and tissue). In some embodiments, smaller doses provided by the present invention may aid in minimizing side and toxicity effects of particular therapeutics.

REFERENCES

References from Part I. (Soluble Nanodiamond-Drug Complexes) and Example 1

1. Goga, A.; Yang, D.; Tward, A. D.; Morgan, D. O., Bishop, J. M Inhibition of Cdk1 as a Potential Therapy for Tumors Over-Expressing MYC. *Nat. Med.* 2007, 13, 820-827.
2. Pantazis, P. Preclinical Studies of Water-Insoluble Camptothecin Congeners: Cytotoxicity, Development of Resistance, and Combination Treatments. *Clin. Canc. Res.* 1995, 1, 1235-1244.
3. Villerbu, N.; Gaben, A. M.; Redeuilh, G.; Mester, J. Cellular effects of purvalanol A: A specific inhibitor of cyclin-dependent kinase activities. *Int. J. Canc.* 2002, 97, 761-769.
4. May, F. E., Westley, B. R. Effects of Tamoxifen and 4-hydroxytamoxifen on the pNR-1 and pNR-2 Estrogen-Regulated RNAs in Human Breast Cancer Cells. *J. Biol. Chem.* 1987, 262, 15894-15899.
5. Rouanet, P.; Linares-Cruz, G.; Dravet, F.; Poujol, S.; Gourgou, S.; Simony-Lafontaine, J.; Grenier, J.; Kramar, A.; Girault, J.; Le Nestour, E.; Maudelonde, T. Neoadjuvant Percutaneous 4-Hydroxytamoxifen Decreases Breast Tumoral Cell Proliferation: A Prospective Controlled Randomized Study Comparing Three Doses of 4-Hydroxytamoxifen Gel to Oral Tamoxifen. *J. Clin. Onco.* 2005, 23, 2980-2987.
6. Kim, Y.; Dalhaimer, P.; Christian, D. A.; Discher, D. Polymeric Worm Micelles as Nano-Carriers for Drug Delivery. *Nanotechnology* 2005, 16, S484-S491.
7. Zhang, L.; Chan, J. M.; Gu, F. X.; Rhee, J.-W.; Wang, A. Z.; Radovic-Moreno, A. F.; Alexis, F.; Langer, R. S.; Farokhzad, O. C. Self-Assembled Lipid-Polymer Hybrid Nanoparticles: A Robust Drug Delivery Platform. *ACS Nano* 2008, 2, 1696-1702.
8. Zhang, L.; Radovic-Moreno, A. F.; Alexis, F.; Gu, F. X.; Basto, P. A.; Bagalkot, V.; Sangyong, J.; Langer, R. S.; Farokhzad, O. C. Co-Delivery of Hydrophobic and Hydrophilic Drugs from Nanoparticle-Aptamer Bioconjugates. *Chem Med Chem* 2007, 2, 1268-1271.
9. Sheihet, L.; Dubin, R. A.; Devore, D.; Kohn, J. Hydrophobic Drug Delivery by Self-Assembling Triblock Copolymer-Derived Nanospheres. *Biomacromol.* 2005, 6, 2726-2731.
10. Deming, T. J. Methodologies for Preparation of Synthetic Block Copolypeptides: Materials with Future Promise in Drug Delivery. *Adv. Drug Deliv. Rev.,* 2002, 54, 1145-1155.
11. Lacerda, L.; Bianco, A.; Prato, M.; Kostarelos, K. Carbon Nanotubes as Nanomedicines: From Toxicology to Pharmacology. *Adv. Drug Deliv. Rev.,* 2006, 58, 1460-1470.
12. Langer, R. New Methods of Drug Delivery. *Science,* 1990, 249, 1527-1533.
13. Peer, D.; Karp, J. M.; Hong, S.; Farokhzad, O. C.; Margalit, R.; Langer, R. Nanocarriers as an Emerging Platform for Cancer Therapy. *Nat. Nanotechnol.,* 2007, 2, 751-760.
14. Kam N. W. S.; O'Connell, M.; Wisdom, J. A.; Dai, H. Carbon Nanotubes as Multifunctional Biological Transporters and Near-Infrared Agents for Selective Cancer Cell Destruction. *Proc. Nat. Acad. Sci.-USA* 2005, 102, 11600-11605.
15. Liu, Z.; Robinson, J. T.; Sun, X.; Dai, H. PEGylated Nanographene Oxide for Delivery of Water-Insoluble Cancer Drugs. *J. Am. Chem. Soc.* 2008, 130, 10876-10877.
16. Gruen, D. M. Nanocrystalline Diamond Films. *Annu. Rev. Mater. Sci.,* 1999, 29, 211-259.
17. Petrov, I. L.; Shenderova, I. L. Ultra Nanocrystalline Diamond: Synthesis, Properties and Applications; Shenderova, O. A.; Gruen, D. M., Eds.; William Andrew Publishing: New York, 2006; pp 529-550.

18. Yeap, W. S.; Tan, Y. Y.; Loh, K. P. Using Detonation Nanodiamond for the Specific Capture of Glycoproteins. *Anal. Chem.,* 2008, 80, 4659-4665.
19. Krüger, A. Hard and Soft: Biofunctionalized Diamond. *Angew. Chem. Int. Ed.,* 2006, 45, 6426-6427.
20. Huang, L.-C. L.; Chang, H.-C. Adsorption and Immobilization of Cytochrome c on Nanodiamonds. *Langmuir,* 2004, 20, 5879-5884.
21. Ushizawa, K.; Sato, Y.; Mitsumori, T.; Machinami, T.; Ueda, T.; Ando, T. Covalent Immobilization of DNA on Diamond and its Verification by Diffuse Reflectance Infrared Spectroscopy. *Chem. Phys. Lett.,* 2002, 351, 105-108.
22. Krüger, A.; Kataoka, F.; Ozawa, M.; Fujino, T.; Suzuki, Y.; Aleksenskii, A. E.; Vul, A. Y.; Ōzawa, E. Unusually Tight Aggregation in Detonation Nanodiamond: Identification and Disintegration. *Carbon,* 2005, 43, 1722-1730.
23. Bondar, V. S.; Puzyr, A. P. Nanodiamonds for Biological Investigations. *Phys. Solid State,* 2004, 46, 716-719.
24. Ozawa, M.; Inaguma, M.; Takahashi, M.; Kataoka, F.; Kruger, A.; Ōsawa, E. Preparation and Behavior of Brownish, Clear Nanodiamond Colloids. *Adv. Mater.,* 2007, 19, 1201-1206.
25. Kossovsky, N.; Gelman, A.; Hnatyszyn, H. J.; Rajguru, S.; Garrell, R. L.; Torbati, S.; Freitas, S. S. F.; Chow, G.-M. Surface-Modified Diamond Nanoparticles as Antigen Delivery Vehicles. *Bioconjugate. Chem.,* 1995, 6, 507-511.
26. Huang, H.; Pierstorff, E.; Ōsawa, E.; Ho, D. Active Nanodiamond Hydrogels for Chemotherapeutic Delivery. *Nano Lett.,* 2007, 7, 3305-3314.
27. Huang, H.; Pierstorff, E.; Ōsawa, E.; Ho, D. Protein-Mediated Assembly of Nanodiamond Hydrogels into a Biocompatible and Biofunctional Multilayer Nanofilm. *ACS Nano,* 2008, 2, 203-212.
28. Lam, R.; Chen, M.; Pierstorff, E.; Huang, H.; Osawa, E.; Ho, D. Nanodiamond-Embedded Microfilm Devices for Localized Chemotherapeutic Elution. *ACS Nano* 2008, 2, 2095-2102.
29. Huang, H.; Chen, M.; Bruno, P.; Lam, R.; Robinson, E.; Gruen, D.; Ho, D. Ultrananocrystalline Diamond Thin Films Functionalized with Therapeutically Active Collagen Networks. *J. Phys. Chem. B* 2009, 113, 2966-2971.
30. Dolmatov, V. Y. Detonation Synthesis Ultradispersed Diamonds: Properties and Applications. *Russ. Chem. Rev.,* 2001, 70, 607-626.
31. Schrand, A. M.; Huang, H.; Carlson, C.; Schlager, J. J.; Ōsawa, E.; Hussain, S. M.; Dai, L. Are Diamond Nanoparticles Cytotoxic? *J. Phys. Chem. B,* 2007, 111, 2-7.
32. Liu, K.-K.; Cheng, C.-L.; Chang, C.-C.; Chao, J.-I. Biocompatible and Detectable Carboxylated Nanodiamond on Human Cell. *Nanotechnology,* 2007, 18, 325102.
33. Yu, S.-J.; Kang, M.-W.; Chang, H.-C.; Chen, K.-M.; Yu, Y.-C. Bright Fluorescent Nanodiamonds: No Photobleaching and Low Cytotoxicity. *J. Am. Chem. Soc.,* 2005, 127, 17604-17605.
34. Härtl, A.; Schmich, E.; Garrido, J. A.; Hernando, J.; Catharino, S. C. R.; Walter, S.; Feulner, P.; Kromka, A.; Steinmüller, D.; Stutzmann, M. Protein-Modified Nanocrystalline Diamond Thin Films for Biosensor Applications. *Nat. Mater.,* 2004, 3, 736-742.
35. Yang, W.; Auciello, O.; Butler, J. E.; Cai, W.; Carlisle, J. A.; Gerbi, J. E.; Gruen, D. M.; Knickerbocker, T.; Lasseter, T. L.; Russell, Jr., et al. DNA-Modified Nanocrystalline Diamond Thin-Films as Stable, Biologically Active Substrates. *Nat. Mater.,* 2002, 1, 253-257.
36. Neugart, F.; Zappe, A.; Jelezko, F.; Tietz, C.; Boudou, J. P.; Krueger, A.; Wrachtrup, J. Dynamics of Diamond Nanoparticles in Solution and Cells. *Nano Lett.* 2007, 7, 3588-3591.
37. Fisher, B.; Costantino, J. P.; Wickerham, D. L.; Redmond, C. K.; Kavanah, M.; Cronin, W. M; et al. Tamoxifen for Prevention of Breast Cancer: Report of the National Surgical Adjuvant Breast and Bowel Project P-1 Study. *J. Natl. Cancer Inst.* 1998, 90, 1371-1388.
38. Fisher, B.; Dignam, J.; Wolmark, N.; Wickerham, D. L.; Fisher, E. R.; Mamounas, E. et al. Tamoxifen in Treatment of Intraductal Breast Cancer: National Surgical Adjuvant Breast and Bowel Project B-24 Randomised Controlled Trial. *Lancet* 1999, 353, 1993-2000.
39. Taylor, C. M.; Blanchard, B.; Zava, D. T. Estrogen Receptor-mediated and Cytotoxic Effects of the Antiestrogens Tamoxifen and 4-Hydroxytamoxifen. *Cancer Res.* 1984, 44, 1409-1414.
40. Gauduchon, J.; Gouilleux, F.; Maillard, S.; Marsaud, V.; Renoir, J.-M.; Sola, B.—Hydroxytamoxifen Inhibits Proliferation of Multiple Myeloma Cells In vitro through Down-Regulation of c-Myc, Up-Regulation of $p27^{Kip1}$, and Modulation of Bcl-2 Family Members. *Clin. Canc. Res.* 2005, 11, 2345-2354.
41. Kircheis, R.; Wightman, L.; Wagner, E. Design and Gene Delivery Activity of Modified Polyethylenimines. *Advanced Drug Delivery Reviews* 2001, 53, 341-358.
42. Bettinger, T.; Remy, J-S.; Erbacher, P. Size Reduction of Galactosylated PEI/DNA Complexes Improves Lectin-Mediated Gene Transfer into Hepatocytes. *Bioconjugate Chem.* 1999, 10, 558-561.

References for Part III. (Alkaline-Sensitive Nanodiamond-Protein Complexes) and Example 2

1. Mochalin V N, Gogotsi Y. Wet Chemistry Route to Hydrophobic Blue Fluorescent Nanodiamond. J Am Chem Soc 2009; 131(13):4594-5.
2. Chang Y-R, Lee H-Y, Chen K, Chang C-C, Tsai D-S, Fu C-C, Lim T-S, Tzeng Y-K, Fang C-Y, Han C-C, Chang H-C, Fann W. Mass production and dynamic imaging of fluorescent nanodiamonds. Nat Nanotechnol 2008; 3(5): 284-8.
3. Fu C-C, Lee H-Y, Chen K, Lim T-S, Wu H-Y, Lin P-K, Wei P-K, Tsao P-H, Chang H-C, Fann W. Characterization and application of single fluorescent nanodiamonds as cellular biomarkers. Proc Nat Acad Sci USA 2007; 104(3):727-32.
4. Deming T J. Methodologies for preparation of synthetic block copolypeptides: materials with future promise in drug delivery. Adv Drug Deliv Rev 2002; 54(8):1145-55.
5. Zhang L, Chan J M, Gu F X, Rhee J-W, Wang A Z, Radovic-Moreno A F, Alexis F, Langer R, Farokhzad O C. Self-assembled lipid-polymer hybrid nanoparticles: a robust drug delivery platform. ACS Nano 2008; 2(8): 1696-702.
6. Farokhzad O C, Langer R. Impact of Nanotechnology on Drug Delivery. ACS Nano 2009; 3(1):16-20.
7. Xu P, Gullotti E, Tong L, Highley C B, Errabelli D R, Hasan T, Cheng J-X, Kohane D S, Yeo Y. Intracellular drug delivery by poly(lactic-co-glycolic acid) nanoparticles, revisited. Mol Pharm 2009; 6(1):190-201.
8. Huang H, Pierstorff E, Osawa E, Ho D. Active Nanodiamond Hydrogels for Chemotherapeutic Delivery. Nano Lett 2007; 7(11):3305-14.
9. Lam R, Chen M, Pierstorff E, Huang H, Osawa E, Ho D. Nanodiamond-Embedded Microfilm Devices for Localized Chemotherapeutic Elution. ACS Nano 2008; 2(10): 2095-102.

10. Pathak P, Meziani M J, Desai T, Foster C, Diaz J A, Sun Y P. Supercritical fluid processing of drug nanoparticles in stable suspension. J Nanosci Nanotechnol 2007; 7(7): 2542-5.
11. Cheong S-J, Lee C-M, Kim S-L, Jeong H-J, Kim E-M, Park E-H, Kim D W, Lim S T, Sohn M-H. Superparamagnetic iron oxide nanoparticles-loaded chitosan-linoleic acid nanoparticles as an effective hepatocyte-targeted gene delivery system. Int J Pharm 2009; 372(1-2):169-76.
12. Dobson J. Gene therapy progress and prospects: magnetic nanoparticle-based gene delivery. Gene Ther 2006; 13(4):283-7.
13. Panyam J, Labhasetwar V. Biodegradable nanoparticles for drug and gene delivery to cells and tissue. Adv Drug Deliv Rev 2003; 55(3):329-47.
14. Allen T M, Cullis P R. Drug Delivery Systems: Entering the Mainstream. Science 2004; 303(5665):1818-22.
15. Gwinn M R, Vallyathan V. Nanoparticles: Health Effects—Pros and Cons. Environ Health Perspect 2006; 114(12):1818-25.
16. Niemeyer C M. Nanoparticles, proteins, and nucleic acids: biotechnology meets material science. Angew Chem Int Ed 2001; 40(22):4128-58.
17. Gelperina S, Kisich K, Iseman M D, Heifets L. The Potential Advantages of Nanoparticle Drug Delivery Systems in Chemotherapy of Tuberculosis. Am J Resp Crit Care 2005; 172(12):1487-90.
18. Hilder T A, Hill J M. Carbon nanotubes as drug delivery nanocapsules. Curr Appl Phys 2007; 8(3-4):258-61.
19. Ajima K, Yudasaka M, Murakami T, Maigné A, Shiba K, Iijima S. Carbon Nanohorns as Anticancer Drug Carriers. Mol Pharm 2005; 2(6):475-80.
20. Cevc G, Richardsen H. Lipid vesicles and membrane fusion. Adv Drug Deliv Rev 1999; 38(3):207-32.
21. Mirsa R D K. Magnetic nanoparticle carrier for targeted drug delivery: perspective, outlook and design. J Mater Sci Technol 2008; 24(9):1011-9.
22. Huang H, Chen M, Bruno P, Lam R, Robinson E, Gruen D, Ho D. Ultrananocrystalline Diamond Thin Films Functionalized with Therapeutically Active Collagen Networks. J Phys Chem B 2009; 113(10):2966-71.
23. Behler K D, Stravato A, Mochalin V, Komeva G, Yushin G, Gogotsi Y. Nanodiamond-Polymer Composite Fibers and Coatings. ACS Nano 2009; 3(2):363-9.
24. Hanson J A, Chang C B, Graves S M, Li Z, Mason T G, Deming T J. Nanoscale double emulsions by single-component block copolypeptides. Nature 2008; 455 (7209):85-8.
25. Auguste D T, Furman K, Wong A, Fuller J, Armes S P, Deming T J, Langer R. Triggered release of siRNA from poly(ethylene glycol)-protected, pH-dependent liposomes. J Control Release 2008; 130(3):266-74.
26. Yeo Y, Ito T, Bellas E, Highley C B, Marini R, Kohane D S. In Situ Cross-linkable Hyaluronan Hydrogels Containing Polymeric Nanoparticles for Preventing Postsurgical Adhesions. Ann Surg 2007; 245(5):819-24.
27. Pathak P, Meziani M J, Desai T, Sun Y P. Nanosizing drug particles in supercritical fluid processing. J Am Chem Soc 2004; 126(35):10842-3.
28. Huang H, Pierstorff E, Osawa E, Ho D. Protein-Mediated Assembly of Nanodiamond Hydrogels into a Biocompatible and Biofunctional Multilayer Nanofilm. ACS Nano 2008; 2(2):203-12.
29. Yeap W S, Chen S, Loh K P. Detonation Nanodiamond: An Organic Platform for the Suzuki Coupling of Organic Molecules. Langmuir 2009; 25(1):185-91.
30. Panessa-Warren B J, Warren J B, Wong S S, Misewich J A. Biological cellular response to carbon nanoparticle toxicity. J Phys: Condens Matter 2006; 18(33):S2185-S201.
31. Puzyr A P, Baron A V, Purtov K V, Bortnikov E V, Skobelev N N, Mogilnaya O A, Bondar V S. Nanodiamonds with novel properties: A biological study. Diamond Relat Mater 2007; 16(12):2124-8.
32. Schrand A M, Huang H, Carlson C, Schlager J J, Osawa E, Hussain S M, Dai L. Are Diamond Nanoparticles Cytotoxic? J Phys Chem B 2007; 111(1):2-7.
33. Zhao W, Xu J-J, Qiu Q-Q, Chen H-Y. Nanocrystalline diamond modified gold electrode for glucose biosensing. Biosens Bioelectron 2006; 22(5):649-55.
34. Huang L C L, Chang H-C. Adsorption and Immobilization of Cytochrome c on Nanodiamonds. Langmuir 2004; 20(14):5879-84.
35. Cao H, Urban J F, Anderson R A. Insulin Increases Tristetraprolin and Decreases VEGF Gene Expression in Mouse 3T3-L1 Adipocytes. Obesity 2008; 16(6):1208-18.
36. Adochio R, Leitner J W, Hedlund R, Draznin B. Rescuing 3T3-L1 Adipocytes from Insulin Resistance Induced by Stimulation of Aid-Mammalian Target of Rapamycin/p70 S6 Kinase (S6K1) Pathway and Serine Phosphorylation of Insulin Receptor Substrate-1: Effect of Reduced Expression of p85α Subunit of Phosphatidylinositol 3-Kinase and S6K1 Kinase. Endocrinology 2009; 150(3):1165-73.
37. Speller C V, Meot-Ner M. The ionic hydrogen bond and ion solvation. 3. Bonds involving cyanides. Correlations with proton affinities. J Phys Chem 1985; 89(24):5217-22.
38. Farías R N, Viñals A E L, Posse E, Morero R D. Relationship between isoelectric point of native and chemically modified insulin and liposomal fusion. Biochem J 1989; 264(1):285-7.
39. Feng L, Andrade J D. Protein adsorption of low-temperature isotropic carbon: I. Protein conformational change probed by differential scanning calorimetry. J Biomed Mater Res 1994; 28(6):735-43.
40. Iida K T, Suzuki H, Sone H, Shimano H, Toyoshima H, Yatoh S, Asano T, Okuda Y, Yamada N. Insulin Inhibits Apoptosis of Macrophage Cell Like, THP-1 Cells, via Phosphatidylinositol-3-Kinas-Dependent Pathway. Arterioscler Thromb Vasc Biol 2002; 22(3):380-6.
41. Greenway S E, Filler L E, Greenway F L. Topical insulin in wound healing: a randomised, double-blind, placebo-controlled trial. J Wound Care 1999; 8(10):526-8.
42. Liu Y, Petreaca M, Yao M, Martins-Green M. Cell and molecular mechanisms of keratinocyte function stimulated by insulin during wound healing. BMC Cell Biol 2009; 10(1).
43. Pierre E J, Barrow R E, Hawkins H K, Nguyen T T, Sakurai Y, Desai M, Wolfe R R, Herndon D N. Effects of insulin on wound healing. J Trauma 1998; 44(2):342-5.
44. Liu Y, Zhang X, Zhang Z, Fang P Y, Xu W S. Effects of topical application of insulin on the wound healing in scalded rats. Chinese J Burns 2004; 20(2):98-101.
45. Zhang X J, Wu X, Wolf S E, Hawkins H K, Chinkes D L, Wolfe R R. Local insulin-zinc injection accelerates skin donor site wound healing. J Surg Res 2007; 142(1):90-6.
46. Schneider L A, Korber A, Grabbe S, Dissemond J. Influence of pH on wound-healing: a new perspective for wound-therapy? Arch Dermatol Res 2007; 298(9):413-20.
47. Osti E. Skin pH variations from the acute phase to re-epithelialization in burn patients treated with new materials (Burnshield, semipermeable adhesive film, Dermasilk, and Hyalomatrix). Non-invasive preliminary experimental clinical trial. Ann Burns and Fire Disasters 2007; 21(2):73-7.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:
1. A composition consisting essentially of:
  a) purified water;
  b) a plurality of doxorubicin molecules; and
  c) a plurality of nanodiamond particles suspended in said purified water, wherein said plurality doxorubicin molecules are adsorbed to at least a portion of said plurality of nanodiamond particles, and wherein each of said nanodiamond particles has a diameter of approximately 2-8 nm.

* * * * *

SEQUENCE LISTING

```
<160> NUMBER OF SEQ ID NOS: 6

<210> SEQ ID NO 1
<211> LENGTH: 17
<212> TYPE: DNA
<213> ORGANISM: Artificial Sequence
<220> FEATURE:
<223> OTHER INFORMATION: Synthetic DNA Primer

<400> SEQUENCE: 1
aggtggcccg gcagaag                                                   17

<210> SEQ ID NO 2
<211> LENGTH: 26
<212> TYPE: DNA
<213> ORGANISM: Artificial Sequence
<220> FEATURE:
<223> OTHER INFORMATION: Synthetic DNA Primer

<400> SEQUENCE: 2
gccttagttg cagtagttct ccagct                                         26

<210> SEQ ID NO 3
<211> LENGTH: 21
<212> TYPE: DNA
<213> ORGANISM: Artificial Sequence
<220> FEATURE:
<223> OTHER INFORMATION: Synthetic DNA Primer

<400> SEQUENCE: 3
ccagaggcgc atgaagctaa t                                              21

<210> SEQ ID NO 4
<211> LENGTH: 20
<212> TYPE: DNA
<213> ORGANISM: Artificial Sequence
<220> FEATURE:
<223> OTHER INFORMATION: Synthetic DNA Primer

<400> SEQUENCE: 4
cggcctctcg tcctgaccat                                                20

<210> SEQ ID NO 5
<211> LENGTH: 22
<212> TYPE: DNA
<213> ORGANISM: Artificial Sequence
<220> FEATURE:
<223> OTHER INFORMATION: Synthetic DNA Primer

<400> SEQUENCE: 5
aaccgaaaag ccattgtaga aa                                             22

<210> SEQ ID NO 6
<211> LENGTH: 17
<212> TYPE: DNA
<213> ORGANISM: Artificial Sequence
<220> FEATURE:
```

| | |
|---|---|
| <223> OTHER INFORMATION: Synthetic DNA Primer | |
| <400> SEQUENCE: 6 | |
| cctggcgttg ggattgg | 17 |